US006251586B1

(12) United States Patent
Mulshine et al.

(10) Patent No.: US 6,251,586 B1
(45) Date of Patent: Jun. 26, 2001

(54) EPITHELIAL PROTEIN AND DNA THEREOF FOR USE IN EARLY CANCER DETECTION

(75) Inventors: James L. Mulshine, Bethesda; Melvin S. Tockman, Baltimore, both of MD (US)

(73) Assignees: The United States of America as represented by the Department of Health and Human Services, Washington, DC (US); The Johns Hopkins University, Baltimore, MD (US)

( * ) Notice: Subject to any disclaimer, the term of this patent is extended or adjusted under 35 U.S.C. 154(b) by 0 days.

(21) Appl. No.: 08/725,027

(22) Filed: Oct. 2, 1996

Related U.S. Application Data

(63) Continuation-in-part of application No. 08/538,711, filed on Oct. 2, 1995, now Pat. No. 5,994,062.

(51) Int. Cl.[7] .............................. C12Q 1/68; C07H 21/04; G01N 33/53

(52) U.S. Cl. ................................ 435/6; 435/7.1; 436/164; 436/172; 536/23.5; 536/24.31

(58) Field of Search ............................ 435/6, 455, 252.3, 435/320.1, 7.1; 536/23.5, 24.31, 24.33; 436/164, 172

(56) References Cited

U.S. PATENT DOCUMENTS

| | | | |
|---|---|---|---|
| 4,569,788 | 2/1986 | Mulshine et al. | 260/112 R |
| 4,683,195 | 7/1987 | Mullis et al. | 435/6 |
| 4,683,202 | 7/1987 | Mullis | 435/91 |
| 5,194,599 | 3/1993 | Froehler | 536/26.72 |
| 5,256,775 | 10/1993 | Froehler | 536/25.6 |
| 5,264,562 | 11/1993 | Matteucci | 536/23.1 |
| 5,455,159 | 10/1995 | Mulshine et al. | 435/7.23 |

OTHER PUBLICATIONS

Zhou et al, "Purification and Characterization of a Protein That Permits Early Detection of Lung Cancer", *The Journal of Biological Chemistry*, vol. 271, No. 18, pp. 10760–10766, 1996.

(List continued on next page.)

*Primary Examiner*—Carla J. Myers
(74) *Attorney, Agent, or Firm*—McAndrews, Held & Malloy, Ltd.; Donald J. Pochopien, Esq.; Mary L. Kelly

(57) ABSTRACT

The present invention is a purified and isolated epithelial protein, peptide and variants thereof whose increased presence in an epithelial cell is indicative of precancer. One epithelial protein which is an early detection marked for lung cancer was purified from two human lung cancer cell lines, NCI-H720 and NCI-H157. Using a six-step procedure, the epithelial protein was purified using a Western blot detection system under both non-reducing and reducing conditions. Purification steps included anion exchange chromatography, preparative isoelectric focusing, polymer-based $C_{18}$ HPLC and analytic $C_4$ HPLC. After an approximately 25,000 fold purification the immunostaining protein was >90% pure as judged by coomassie blue staining after reducing SDS-PAGE. The primary epithelial protein share some sequence homology with the heterogeneous nuclear ribonucleoprotein (hnRNP) A2. A minor co-purifying epithelial protein shares some sequence homology with the splice variant hnRNP-B1. Molecular analysis of primary normal bronchial epithelial cell cultures demonstrated a low level the epithelial protein expression, consistent with immunohistochemical staining of clinical samples, and an increased level of expression in most lung cancer cells. The epithelial protein is a marker of epithelial transformation in lung, breast, bone, ovary, prostate, kidney, melanoma and myeloma and may be casual in the process of carcinogenesis. Methods are provided for monitoring the expression of the epithelial protein, peptides and variants using molecular and immunological techniques as a screen for precancer and cancer in mammals. A method of computerized diagnoses of cancer and precancer is provided which detects levels of hnRNP messenger RNA.

35 Claims, 22 Drawing Sheets

DUAL-WAVELENGTH IMAGE DENSITOMETRY

OTHER PUBLICATIONS

Mulshine et al, "Monoclonal Antibodies That Distinguish Non–Small Cell From Small Cell Lung Cancer", *The Journal of Immunology*, vol. 131, No. 1, pp. 497–502, Jul. 1983.

Tockman et al, "Considerations in Bringing a Cancer Biomarker to Clinical Application", *Cancer Research* (Suppl.), 52, 2711s–2718s, May 1992.

Kumar et al, Purification and Domain Structure of Core hnRNP Proteins A1 and A2 and Their Relationship to Single–stranded DNA–binding Proteins, *The Journal of Biological Chemistry*, vol. 261, No. 24, Aug. 25, 1986, pp. 11266–11273.

Boffa et al, Distribution of $N^G$, $N^G$–Dimethylarginine in Nuclear Protein Fractions, *Biochemical and Biophysical Research Communications*, vol. 74, No. 3, 1977, pp. 969–976.

Williams et al, Amino acid sequence of the UP1 calf thymus helix–destabilizing protein and its homology to an analogous protein from mouse myeloma, *Proc. Natl. Acad. Sci. USA*, vol. 82, Sep. 1985, pp. 5666–5670.

Merrill et al, High Pressure Liquid Chromatography Purification of UP1 and UP2, Two Related Single stranded Nucleic Acid–binding Proteins from Calf Thymus, *The Journal of Biological Chemistry*, vol. 261, No. 2, Jan. 15, 1986, pp. 878–883.

Medzihradszky et al, Characterization of Protein N–Glycosylation by Reversed–Phase Microbore Liquid Chromatography/Electrospray Mass Spectrometry, Complementary Mobile Phases, and Sequential Exoglycosidase Digestion, *J Am Soc Mass Spectrom*, 1994, 5, pp. 350–358.

Karn et al, Characterization of the Non–histone Nuclear Proteins Associated with Rapidly Labeled Heterogeneous Nuclear RNA, *The Journal of Biological Chemistry*, vol. 252, No. 20, Oct. 1977, pp. 7307–7322.

Mayeda et al, Function of conserved domains of hnRNP A1 and other hnRNP A/B proteins, *The EMBO Journal*, vol. 13, No. 22, pp. 5483–5495, 1994.

Anderson et al, A two–dimensinal gel database of rat liver proteins useful in gene regulation and drug effects studies, *Electrophoresis*, 1991, 12, pp. 907–930.

Burd et al, Conserved Structures and Diversity of Functions of RNA–Binding Proteins, *Science*, vol. 265, Jul. 29, 1994, pp. 615–621.

Martinez et al, Non–radioactive Localization of Nucelic Acids by Direct In Situ PCR and In Situ RT–PCR in Paraffin–embedded Sections, *The Journal of Histochemistry and Cytochemistry*, vol. 43, No. 8, pp. 739–747, 1995.

Tockman et al, Sensitive and Specific Monoclonal Antibody Recognition of Human Lung Cancer Antigen on Preserved Sputum Cells: A New Approach to Early Lung Cancer Detection, *Journal of Clinical Oncology*, vol. 6, No. 11, Nov. 1988, pp. 1685–1693.

Tockman et al, The Early Detection of Second Primary Lung Cancers by Sputum Immunostaining, *Chest*, vol. 106, No. 6, Dec. 1994, pp. 385S–390S.

Scott et al, Prospective Trial Evaluating Immunocytochemical–based Sputum Techniques for Early Lung Cancer Detection: Assays for Promotion Factors in the Bronchila Lavage, *Journal of Cellular Biochemistry*, Supplement 17F:175–183 (1993).

Mulshine et al, Monoclonal Antibodies That Distinguish Non–Small Cell From Small–Cell Lung Cancer, *The Journal of Immunology*, vol. 131, No. 1, Jul. 1983, pp. 497–502.

Mulshine et al, Molecular Markers in Early Cancer Detection, *Chest*, vol. 107, No. 6, Jun. 1995 Supplement, pp. 280S–286S.

Wulf et al, Improvement of Fluorescence In Situ Hybridization (RNA–FISH) on Human Paraffin Sections by Propidium Iodide Counterstaining, *BioTechniques*, vol. 19, No. 3, Sep. 1995.

Saccomanno et al, Cytology of the lung in reference to irritant, individual sensitivity and healing, *Acta Cytol*, 14:377–380, 1970.

Saccomanno et al, Development of carcinoma of the lung as reflected in exfoliated cells, *Cancer*, 33:256–270, 1974.

Naisell et al, Cytological studies in man and animals on development of bronchogenic carcinoma. In: Lung Carcinomas, E. McDowell (eds), pp. 207–242, New York: Churchill Livingstone, 1987.

Jensen et al, Clara cell 10KD protein mRNA in normal and atypical regions of human respriatory epithelium. *Int. J. Cancer*, 58: 629–637, 1994.

Sozzi et al, Cytogenetic abnormalities and overexpression of receptors for growth factor in normal bronchial epithelium and tumor samples of lung cancer patients, *Cancer Res.*, 51: 400–404, 1991.

Carter et al, Relationship of morphology of clinical presentation in ten cases of early squamous carcinoma of the lung, *Cancer*, 37: 1389–1396, 1976.

Shaw et al, Individualized chemotherapy for patients with non–small cell lung cancer determined by prospective identification of neuroendocrine markers and in vitro drug sensitivity testing, *Cancer Research* 53:5180–5187, 1993.

Burd, C.G. et al, Primary structures of the heterogeneous nuclear ribonucleoprotein A2, B1, and C2 proteins: A diversity of RNA binding proteins is generated by small peptide inserts, *Proc. Nat'l Sci. USA* 86, 9788–9792 (1989).

Dreyfuss et al, hnRNP Proteins and the Biogenesis of mRNA, *Ann. Res Biochem.*, vol. 62, pp. 289–321, 1993.

Biamonti, G. et al, Two homologous genes, originated by duplication, encode the human hnRNP proteins A2 and A1, *Nucleic Acid Res.*, Jun. 1994, vol. 22(11):1996–2002.

Biamonti, Human hnRNP Protein A1 Gene Expression, *J. Mol. Biol.*, vol. 230, pp. 77–89, 1993.

Ishikawa, F. et al, Nuclear Proteins That Bind the Pre–m-RNA 3' Splice Site Sequence r(UUAG/G) and the Human Telemeric DNA Sequence d$(TTAGGG)_n$, *Mol. Cell. Biol.* vol. 13, 4301–4310, 1993.

McKay, S.J. et al, hnRNP A2/B1 binds specifically to single stranded vertebrate telemeric repeat $TTAGGG_n$, *Nucleic Acids Res.*, vol. 20:6461–64, 1992.

Padmapriya et al, Synthesis of Oligodeoxynucleoside Methylphosphonothioates, *Bio Org. & Med. Chem. Lett.*, 3, 761–764 (1993).

Temsamani et al, Capped Oligodeoxynucleotide Phosphorothioates, *Ann. N.Y. Acad. Sci.*, vol. 660, pp. 318–320, (1992).

Tang et al, Self–stabilized antisense oligodeoxynucleotide phosphorothioates: properties and anti–HIV activity, *Nucleic Acids Res.*, vol. 21, No. 11, pp. 2729–2735, 1993.

Krajewski, Investigation of the subcellular distribution of the bcl–2 oncoprotein: Residence in the Nuclear Envelope, Endoplasmic Reticulum, and Outer Mitrochondrial Membranes, *Cancer Res.*, 53:4701–4714, 1993.

Spector, D.L., Nuclear organization of pre–mRNA processing, *Curr. Opin. Cell. Biol.* 5, 442–447, 1993.
Katz, D. et al, AU–A, an RNA–binding activity distinct from hnRNP A1, is selective for AUUUA repeats and shuttles between the nucleus and the cytoplasm, *Nucleic Acid Res.*, Vo. 22, No. 2, pp. 238–246, 1994.
Pinol–Roma et al, Shuttling of pre–mRNA binding proteins between nucleus and cytoplasm, *Nature* 355, 730–732, 1992.
Risio, M.J., Cell Proliferation in Colorectal Tumor Progession: An Immunohistochemical Approach to Intermediate Biomarkers, *J. Cell. Biochem.* Suppl. 16G, 79–87, 1992.
Ganju, R.K., CD 10/NEP in Non–small Cell Lung Carcinomas, *J. Clin. Invest.* vol. 94, 1784–1791, 1994.
Saccone, S. et al, Assignment of the Human Heterogeneous Nuclear Ribonucleoprotein A1 Gene (HNRPA1) to Chromosome 12q13.1 by cDNA Competitive in Situ Hybridization, *Genomics* Jan:12(1):171–174, 1992.

Tockman et al, Cytometric Validation of Immunocytochemical Observations in Developing Lung Cancer, *Diagnostic Cytopathology*, vol. 9, No. 6, pp. 615–622, 1993.

Tockman et al, Sensitive and Specific Monoclonal Antibody Recognition of Human Lung Cancer on Preserved Sputum Cells: A New Approach to Early Lung Cancer Detection, *Journal of Clinicla Oncoloyg*, vol. 6, No. 11, pp. 1685–1693, Nov. 1988.

Tockman et al, The Early Detection of Second Primary Lung Cancers by Sputum Immunostaining, *Chest*, vol. 106, No. 6, pp. 385S–390S, 1994.

Martinez et al, "Expression of Peptidyl–Glycine α–Admidating Mono–Oxygenase (PAM) Enzymes in Morphological Abnormalities Adjacent to Pulmonary Tumors", *American Journal of Pathology*, vol. 149, No. 2, pp. 707–716, Aug. 1996.

```
1    ATGTCTAAGTCAGAGTCTCCTAAAGAGCCCGAACAGCTGA   A1-cds (SEQ. ID. NO. 9)
1    ATG---------GAG------AGAGAAAAGGAACAGTTCC   A2 cds (SEQ. ID. NO. 10)

41   GGAAGCTCTTCATTGGAGGGTTGAGCTTTGAAACAACTGA   A1-cds
26   GTAAGCTCTTTATTGGTGGCTTAAGCTTTGAAACCACAGA   A2 cds

81   TGAGAGCCTGAGGAGCCATTTTGAGCAATGGGGAACGCTC   A1-cds
66   AGAAAGTTTGAGGAACTACTACGAACAATGGGGAAAGCTT   A2 cds

121  ACGGACTGTGTGGTAATGAGAGATCCAAACACCAAGCGCT   A1-cds
106  ACAGACTGTGTGGTAATGAGGGATCCTGCAAGCAAAAGAT   A2 cds

161  CTAGGGGCTTTGGGTTTGTCACATATGCCACTGTGGAGGA   A1-cds
146  CAAGAGGATTTGGTTTTGTAACTTTTTCATCCATGGCTGA   A2 cds

201  GGTGGATGCAGCTATGAATGCAAGGCCACACAAGGTGGAT   A1-cds
186  GGTTGATGCTGCCATGGCTGCAAGACCTCATTCAATTGAT   A2 cds

241  GGAAGAGTTGTGGAACCAAAGAGAGCTGTCTCCAGAGAAG   A1-cds
226  GGGAGAGTAGTTGAGCCAAAACGTGCTGTAGCAAGAGAGG   A2 cds

281  ATTCTCAAAGACCAGGTGCCCACTTAACTGTGAAAAAGAT   A1-cds
266  AATCTGGAAAACCAGGGGCTCATGTAACTGTGAAGAAGCT   A2 cds

321  ATTTGTTGGTGGCATTAAAGAAGACACTGAAGAACATCAC   A1-cds
306  GTTTGTTGGCGGAATTAAAGAAGATACTGAGGAACATCAC   A2 cds

361  CTAAGAGATTATTTTGAACAGTTTGGAAAAATTGAAGTGA   A1-cds
346  CTTAGAGATTACTTTGAGGAATATGGAAAAATTGATACCA   A2 cds

401  TTGAAATCATGACTGACCGAGGCAGTGGCAAGAAAAAGGG   A1-cds
386  TTGAGATAATTACTGATAGGCAGTCTGGAAAGAAAAGAGG   A2 cds

441  CTTTGCCTTTGTAACCTTTGACGACCATGACTCCGTGGAT   A1-cds
426  CTTTGGCTTTGTTACTTTTGATGACCATGATCCTGTGGAT   A2-cds

481  AAGATTGTCATTCAGAAATACCATACTGTGAATGGCCACA   A1-cds
466  AAAATCGTATTGCAGAAATACCATACCATCAATGGTCATA   A2 cds

521  ACTGTGAAGTTAGAAAAGCCCTGTCAAAGCAAGAGATGGC   A1-cds
506  ATGCAGAAGTAAGAAAGGCTTTGTCTAGACAAGAAATGCA   A2 cds

561  TAGTGCTTCATCCAGCCAAAGAGGTCGAAGTGGTTCTGGA   A1-cds
546  GGAAGTTCAG---AGTTCTAGGAGTGGAAGAGGA---GGC   A2 cds

601  AACTTTGGTGGTGGTCGTGGAGGTGGTTTCGGTGGGAATG   A1-cds
580  AACTTTGGCTTTGGGGATTCACGTGGTGGCGGTGGAAATT   A2 cds

641  ACAACTTCGGTCGTGGAGGAAACTTCAGTGGTCGTGGTGG   A1-cds
620  TCGGACCAGGACCAGGAAGTAACTTTAGAGGA------GG   A2 cds

681  CTTTGGTGGCAGCCGTGGTGGTGGTGGATATGGTGGCAGT   A1-cds
654  ATCTGATGGATATGGCAGTGGACGTGGAT---------TT   A2 cds

721  GGGGATGGCTATAATGGATTTGGCAA------TGATGGAA   A1-cds
685  GGGGATGGCTATAATGGGTATGGAGGAGGACCTGGAGGTG   A2 cds

755  GCAATTTTGGAGGTG-------------------------   A1-cds
725  GCAATTTTGGAGGTAGCCCCGGTTATGGAGGAGGAAGAGG   A2 cds
```

FIG. 1

Human hnRNP A2

```
cgg gtc ccg tgc gga ggt gct cct cgc aga gtt gtt     36
tct cga gca gcg gca gtt ctc act aca gcg cca gga     72
cga gtc cgg ttc gtg ttc gtc cgc gga gat ctc tct    108
cat ctc gct cgg ctg cgg gaa atc ggg ctg aag cga    144
ctg agt ccg cga tgg aga gag aaa agg aac agt tcc    180
gta acg tct tta ttg gtg gct taa gct ttg aaa cca    216
cag aag aaa gtt tga gga act act acg aac aat ggg    252
gaa agc tta cag act gtg tgg taa tga ggg atc ctg    288
caa gca aaa gat caa gag gat ttg gtt ttg taa ctt    324
ttt cat cca tgg ctg agg ttg atg ctg cca tgg ctg    360
caa gac ctc att caa ttg atg gga gag tag ttg agc    396
caa aac gtg ctg tag caa gag agg aat ctg gaa aac    432
cag ggg ctc atg taa ctg tga aga agc tgt ttg ttg    468
gcg gaa tta aag aag ata ctg agg aac atc acc tta    504
gag att act ttg agg aat atg gaa aaa ttg ata cca    540
ttg aga taa tta ctg ata ggc agt ctg gaa aga aaa    576
gag gct ttg gct ttg tta ctt ttg atg acc atg atc    612
ctg tgg ata aaa tcg tat tgc aga aat acc ata cca    648
tca atg gtc ata atg cag aag taa gaa agg ctt tgt    684
cta gac aag aaa tgc agg aag ttc aga gtt cta gga    720
gtg gaa gag gag gca act ttg gct ttg ggg att cac    756
gtg gtg gcg gtg gaa att tcg gac cag gac cag gaa    792
gta act tta gag gag gat ctg atg gat atg gca gtg    828
gac gtg gat ttg ggg atg gct ata atg ggt atg gag    864
gag gac ctg gag gtg gca att ttg gag gta gcc ccg    900
gtt atg gag gag gaa gag gag gat atg gtg gtg gag    936
gac ctg gat atg gca acc agg gtg ggg gct acg gag    972
gtg gtt atg aca act atg gag gag gaa att atg gaa   1008
gtg gaa att aca atg att ttg gaa att ata acc agc   1044
aac ctt cta act acg gtc caa tga aga gtg gaa act   1080
ttg gtg gta gca gga aca tgg ggg gac cat atg gtg   1116
gag gaa act atg gtc cag gag gca gtg gag gaa gtg   1152
ggg gtt atg gtg gga gga gcc gat act gag ctt ctt   1188
cct att tgc cat ggg ctt cac tgt ata aat agg aga   1224
gga tga gag ccc aga ggt aac aga aca gct tca ggt   1260
```

FIG. 2A

```
tat cga aat aca aat gtg aag gaa act ctt atc tca       1296
gtc atg cat aaa tat gca gtg ata tgg cag aag aca       1332
cca gag cag atg cag aga gcc att ttg tga atg gat       1368
tgg att att taa taa cat tac ctt act gtg gag gaa       1404
gga ttg taa aaa aaa atc cct ttg aga cag ttt ctt       1440
agc ttt tta att gtt gtt tct ttc tag tgg tct ttg       1476
taa gag tgt aga agc att cct tct ttg ata atg tta       1512
aat ttg taa gtt tca ggt gac atg tga aac ctt ttt       1548
taa gat ttt tct caa agt ttt gaa aag cta tta gcc       1584
agg atc atg gtg taa taa gac ata acg ttt ttc ctt       1620
taa aaa aat tta agt gcg tgt gta gag tta aga agc       1656
tgt tgt aca ttt atg att taa taa aat aat tct aaa       1692
gga aaa aa                                            1700
```

FIG. 2B

Human hnRNP-B1

```
ccg tgc gga ggt gct cct cgc aga gtt gtt tct cga      36
gca gcg gca gtt ctc act aca gcg cca gga cga gtc      72
cgg ttc gtg ttc gtc cgc gga gat ctc tcc cat ctc     108
gct cgg ctg cgg gaa atc ggg ctg aag cga ctg agt     144
ccg cga tgg aga aaa ctt tag aaa ctg ttc ctt tgg     180
aga gga aaa aga gag aaa agg aac agt tcc gta agc     216
tct tta ttg gtg gct taa gct ttg aaa cca cag aag     252
aaa gtt tga gga act act acg aac aat ggg gaa agc     288
tta cag act gtg tgg taa tga ggg atc ctg caa gca     324
aaa gat caa gag gat ttg gtt ttg taa ctt ttt cat     360
cca tgg ctg agg ttg atg ctg cca tgg ctg caa gac     396
ctc att caa ttg atg gga gag tag ttg agc caa aac     432
gtg ctg tag caa gag agg aat ctg gaa aac cag ggg     468
ctc atg taa ctg tga aga agc tgt ttg ttg gcg gaa     504
tta aag aag ata ctg agg aac atc acc tta gag att     540
act ttg agg aat atg gaa aaa ttg ata cca ttg aga     576
taa tta ctg ata ggc agt ctg gaa aga aaa gag gct     612
ttg gct ttg tta ctt ttg atg acc atg atc ctg tgg     648
ata aaa tcg tat tgc aga aat acc ata cca tca atg     684
gtc ata atg cag aag taa gaa agg ctt tgt cta gac     720
aag aaa tgc agg aag ttc aga gtt cta gga gtg gaa     756
gag gag gca act ttg gct ttg ggg att cac gtg gtg     792
gcg gtg gaa att tcg gac cag gac cag gaa gta act     828
tta gag gag gat ctg atg gat atg gca gtg gac gtg     864
gat ttg ggg atg gct ata atg ggt atg gag gag gac     900
ctg gag gtg gca att ttg gag gta gcc ccg gtt atg     936
gag gag gaa gag gag gat atg gtg gtg gag gac ctg     972
gat atg gca acc agg gtg ggg gct acg gag gtg gtt    1008
atg aca act atg gag gag gaa att atg gaa gtg gaa    1044
att aca atg att ttg gaa att ata acc agc aac ctt    1080
cta act acg gtc caa tga aga gtg gaa act ttg gtg    1116
gta gca gga aca tgg ggg gac cat atg gtg gag gaa    1152
act atg gtc cag gag gca gtg gag gaa gtg ggg gtt    1188
atg gtg gga gga gcc gat act gag ctt ctt cct att    1224
```

FIG. 3A

```
tgc cat ggg ctt cac tgt ata aat agg aga gga tga          1260
gag ccc aga ggt aac aga aca gct tca ggt tat cga          1296
aat aac aat gtt aag gaa act ctt atc tca gtc atg          1332
cat aaa tat gca gtg ata tgg cag aag aca cca gag          1368
cag atg cag aga gcc att ttg tga atg gat tgg att          1404
att taa taa cat tac ctt act gtg gag gaa gga ttg          1440
taa aaa aaa atg cct ttg aga cag ttt ctt agc ttt          1476
tta att gtt gtt tct ttc tag tgg tct ttg taa gag          1512
tgt aga agc att cct tct ttg ata atg tta aat ttg          1548
taa gtt tca ggt gac atg tga aac ctt ttt taa gat          1584
ttt tct caa agt ttt gaa aag cta tta gcc agg atc          1620
atg gtg taa taa gac ata acg ttt ttc ctt taa aaa          1656
aat tta agt gcg tgt gta gag tta aga agc tgt tgt          1692
aca ttt atg att taa taa aat aat tct aaa gga aaa          1728
aaa aaa aaa aaa aaa aaa aaa aaa aaa aaa aa               1760
```

FIG. 3B

1 MEktletvplerkkREKEQFRKLFIGGLSFETTEESLRNYYEQWGKLTDCVVMRDPASKR
•E------------REKEQFRKLFI * (4kDa)

61 SRGFGFVTFSSMAEVDAAMAARPHSIDGRVVEPKRAVAREESGKPGAHVTVKKLFVGGIK
* •AARPHSIDGRVV (27,13kDa)

121 EDTEEHHLRDYFEEYGKIDTIEIITDRQSGKKRGFGFVTFDDHDPVDKIVLQKYHTINGH

181 NAEVRKALSRQEMQEVQSSRSGRGGNFGFGDSRGGGGNFGPGPGSNFRGGSDGYGSGRGF
•QEVQSSRSGRGG (15kDa)

241 GDGYNGYGGGPGGGNFGGSPGYGGGRGGYGGGGPGYGNQGGGYGGGYDNYGGGNYGSGNY

301 NDFGNYNQQPSNYGPMKSGNFGGSRNMGGPYGGGNYGPGGSGGSGGYGGRSRY
* *

FIG. 4

FIG. 5A
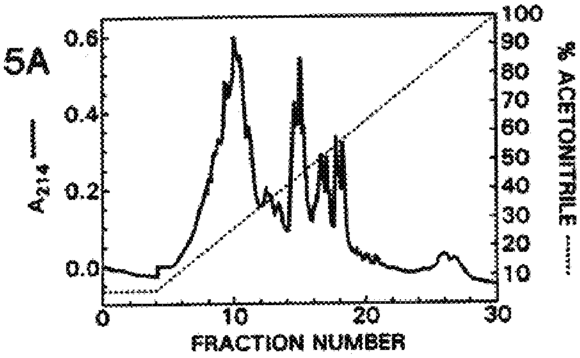
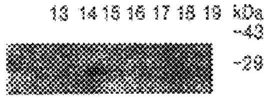
FIG. 5B
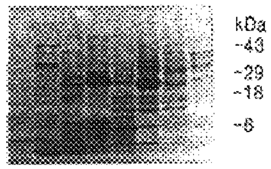
FIG. 5C
FIG. 5D
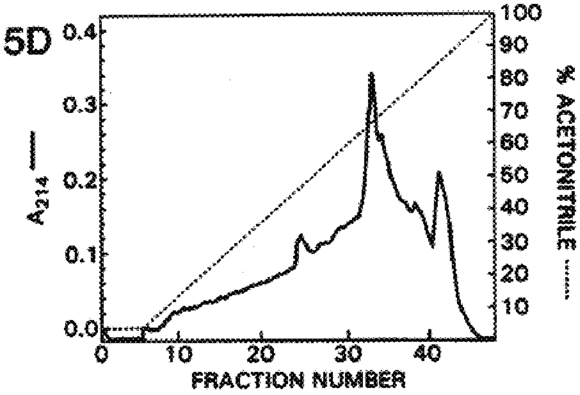
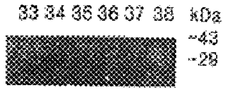
FIG. 5E
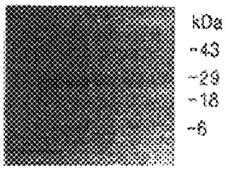
FIG. 5F FIG. 6A
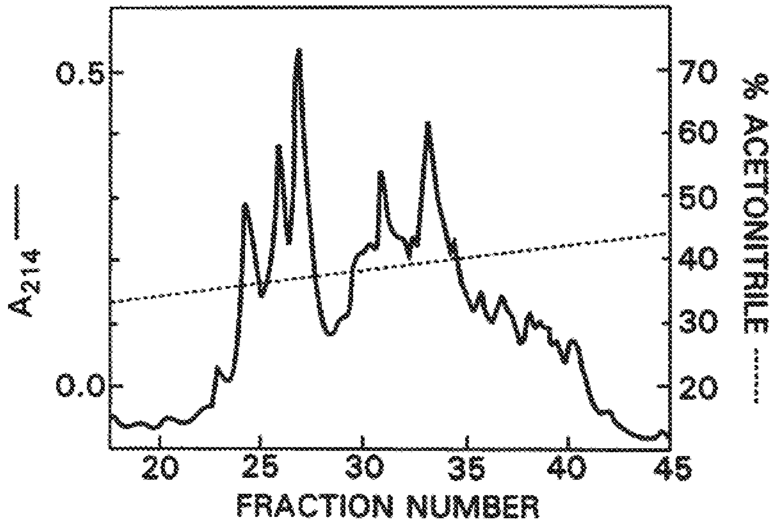
FIG. 6B
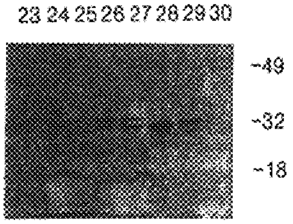
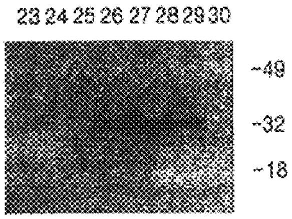
FIG. 6C

FIG. 7A

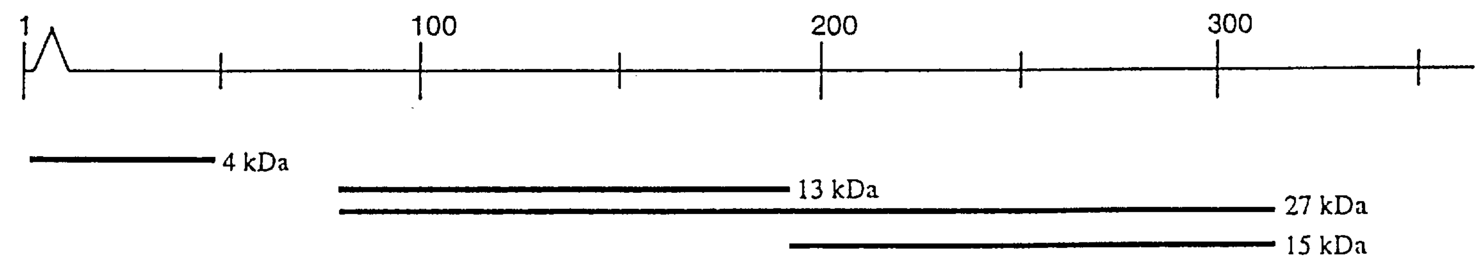

```
  1  MEktletvplerkkREKEQFRKLFIGGLSFETTEESLRNYYEQWGKLTDCVVMRDPASKR
     •E------------REKEQFRKLFI (4 kDa)                            *

 61  SRGFGFVTFSSMAEVDAAMAARPHSIDGRVVEPKRAVAREESGKPGAHVTVKKLFVGGIK
           *      •AARPHSIDGRVV (13 kDa, 27 kDa)

121  EDTEEHHLRDYFEEYGKIDTIEIITDRQSGKKRGFGFVTFDDHDPVDKIVLQKYHTINGH

181  NAEVRKALSRQEMQEVQSSRSGRGGNFGFGDSRGGGGNFGPGPGSNFRGGSDGYGSGRGF
                 •QEVQSSRSGRGG (15 kDa)

241  GDGYNGYGGGPGGGNFGGSPGYGGGRGGYGGGGPGYGNQGGGYGGGYDNYGGGNYGSGNY

301  NDFGNYNQQPSNYGPMKSGNFGGSRNMGGPYGGGNYGPGGSGGSGGYGGRSRY
                   *          *
```

Expression of hnRNP A2 mRNA/protein in Sputum Cells

Control Mixture:Calu-3 + Normal Sputum in Situ Hybridization

Expression of hnRNP A2 mRNA/protein in Sputum Cells

Clinical Sputum Specimens

Immunocytochemistry in Situ Hybridization Antisense

A

Positive Case

B

C

Negative Case

D

Expression of hnRNP in developing mouse lung

EPITHELIAL PROTEIN AND DNA THEREOF FOR USE IN EARLY CANCER DETECTION

This is a continuation-in-part of pending U.S. Ser. No. 08/538,711 filed Oct. 2, 1995 now U.S. Pat. No. 5,994,062.

This invention was made with government support under Lung Cancer SPORE Grant NIH/NCI 1P50 CA58184-01. The government has certain rights in the invention.

FIELD OF THE INVENTION

The present invention relates to the area of cancer diagnostics and therapeutics. More specifically, the invention relates to the isolation and purification of an early cancer detection marker protein of epithelial cells and the cloning of the DNA sequence encoding the protein. The invention further relates to the protein and DNA sequence for detecting and diagnosing individuals predisposed to cancer. The present inventin relates to a computerized method for generating a discriminant function predictive of cancer. The present invention also relates to therapeutic intervention to, regulate the expression of the gene product.

BACKGROUND OF THE INVENTION

Lung cancer is the most frequent cause of cancer death of both males and females in the United States, accounting for one in three cancer deaths[(1)]. In the last thirty years, cancer-related survival of this disease has improved only minimally. Successful treatment of this disease by surgical resection and drug chemotherapy is strongly dependent on identification of early-stage tumors. A conceptually attractive early detection approach is to establish the presence of a cancer by evaluation of shed bronchial epithelial cells. In the late 1960's Saccomanno et al. proposed the use of sputum cytology to evaluate cytomorphologic changes in the exfoliated bronchial epithelium as a technique to enhance the early detection of lung cancer[(2)]. However, clinical trials using combination chest X-ray and sputum cytology have not shown any decrease in cancer-related mortality[(3)].

In 1988, Tockman et al. reported a sensitive method for early lung cancer detection by immunostaining cells contained within sputum samples with two lung cancer-associated monoclonal antibodies[(4)]. The basis for this approach was to identify early pre-neoplastic changes in cells shed from bronchial epithelium. The antibodies used in that study were mouse monoclonal IgG's designated 703D4, disclosed in U.S. Pat. No. 4,569,788, and 624H12. In an analysis of the contribution of the individual monoclonal antibodies to early detection of lung cancer, 703D4 alone identified 20 of the 21 detected true positive cases (4; U.S. Ser. No. 08/152,881 which issues to U.S. Pat. No. 5,455,159 on Oct. 3, 1995). 624H12 has been shown to detect an oncofetal antigen which is the Lewis$^x$-related portion of a cell-surface glycoprotein (Mulshine/Magnani). The antigen for 703D4 was unknown.

703D4 was developed by immunization using a whole tumor cell extract, coupled to keyhole limpet hemocyanin, and selection was based on discrimination amongst subtypes of lung cancer histological subtypes. Preliminary studies showed the 703D4 antibody recognized a protein expressed by most non-small cell lung cancer cells[(5)]. Immunoprecipitation defined a protein of Mr>31 kDa. Since 703D4 demonstrated the ability to selectively detect changes related to the development of cancer in shed bronchial epithelium from the proximal airways, the antigen recognized by 703D4 was purified in the present invention to determine its identity and explore its relationship to early lung cancer detection. The present invention uses a biochemical approach for identification of the epithelial protein from non-small cell lung tumor cells.

With cigarette smoking the entire human respiratory tract is exposed to potential carcinogens and is at increased risk for cancer development. This phenomenon has been called "field cancerization" (8). A variety of epithelial changes have been observed throughout the respiratory tract of both smokers and lung cancer patients (8,9), which may be part of the "field" effect. Saccomanno et al. (6) have demonstrated that centrally located squamous carcinomas of the lung develop through a series of identifiable stages, namely squamous metaplasia, squamous metaplasia with atypia (mild, moderate, marked), carcinoma in situ, and invasive carcinoma (6). These findings were confirmed by later animal and human studies (7). This cytomorphologic classification is useful in defining preneoplastic changes in the proximal region of the lung cancer "field". However, comparable events preceding the other major lung cancer histologies, especially those arising in the peripheral lung (terminal and respiratory bronchioles, alveolar epithelium) are not well defined.

The expression of an epithelial protein in both neoplastic and non-neoplastic regions of distal human lung was investigated.

SUMMARY OF THE INVENTION

The present invention describes the isolation and identification of an epithelial protein which is an early marker for cancer. It is an object of the present invention to provide an isolated and purified epithelial protein, peptide, or variants thereof which are an early marker for lung cancer.

It is an object of the present invention to provide an isolated, purified DNA molecule or portion thereof comprising the coding sequence for an epithelial protein, peptide or variant thereof which is an early marker for cancer.

It is another object of the invention to utilize the isolated DNA, or RNA molecule or portion thereof encoding the epithelial protein which is an early marker for cancer to detect and diagnose the gene and alterations thereof in tissues and cells.

It is another object of the invention to provide nucleic acid probes for the detection of the gene or protein thereof encoding an epithelial protein which is an early marker for cancer.

It is still another object of the invention to provide a method for diagnosing human preneoplastic and neoplastic cells and tissues. In accordance with the invention, the method comprises isolating cells, tissues or extracts thereof from a human and detecting the gene or portion thereof encoding an epithelial protein which is an early marker for cancer or their expression products from the cells, tissue or extracts thereof, wherein detection of a quantitative increase in the gene or expression products indicates preneoplasia and neoplasia.

Another object of the invention is a method for detecting mutations of a gene encoding the epithelial protein which is an early marker for cancer, contained within clones expressing the gene recovered from cancer cells.

Another method for diagnosing human preneoplastic and neoplastic cells and tissues is by detecting post-translational modifications of the epithelial protein in the preneoplastic and neoplastic cells and tissue by immunoassays such as Western blot or immunoelectrophoresis using an antibody that is reactive with the epithelial protein, by two-dimensional electrophoresis or by reverse-phase HPLC.

It is yet another object of the invention to provide a method for monitoring the efficacy of a therapeutic intervention to arrest cancer progression.

It is a further object of the invention to provide a kit comprising oligonucleotides comprising a nucleic acid sequence from DNA, RNA or portion thereof encoding the epithelial protein which is an early marker for cancer, for use in the methods of diagnosis of cancer and early cancer and for use in methods of monitoring the efficacy of cancer treatment.

Still another object of the invention is to provide the epithelial protein, peptides or variants thereof which one substantially homologous to a portion of at least one heterogenous nuclear ribonucleotide protein for use in diagnostic and detection assays, in particular for immunoassays.

One object of the invention is an inhibitory protein analog of the epithelial protein which is capable of binding to the same binding site recognized by the epithelial protein on RNA. Such an analog is capable of competitively inhibiting the function of the epithelial protein, peptide or variant thereof in vitro and in vivo.

It is yet another object of the invention to provide a method for detecting susceptibility to cancer and for diagnosing early-onset tumorigenesis in mammalian cells and tissue. In accordance with the invention, the method comprises isolating a mammalian biological sample and detecting a nucleic acid sequence encoding an epithelial protein or portion thereof which is an early marker for cancer.

The present invention also provides a method of computer-assisted determination of cancer and precancer in a mammal and an algorithm useful for same.

Another aspect of the invention is a method of computerized detection of hnRNP mRNA in a biological sample.

It is yet another aspect of the invention to provide a method of computerized diagnosis of cancer and precancer in a mammal.

Another aspect of the invention is a method of computer-assisted prediction of cancer in a mammal based on image analysis.

A further aspect of the invention is a method for generating a discriminant function useful in identifying atypical cells and in predicting cancer based on computerized image analysis.

A further aspect of the invention is a method of computerized diagnosis of cancer and precancer in a mammal comprising dual-wavelength image densitometry.

Another aspect of the invention is a system for determining an atypical cell from a normal or typical cell in which the system comprises an optical image generator, a device for acquiring an optical image, a processor for analyzing the optical image for cellular parameters unique to an atypical cell and a program for determining a discriminant function. The discriminant function discriminants between atypical or abnormal cells and typical or normal cells. The system is particularly useful in predicting the development of cancer in an individual.

Yet another object of the invention is to provide a method of altering or downregulating the expression of the gene or portion thereof encoding an epithelial protein or portion thereof which is an early marker for cancer of epithelial cells which comprises introduction of antisense oligonucleotides which are substantially complementary to the gene in the epithelial cell. The antisense oligonucleotide allows for non-neoplastic growth of the epithelial cell.

Another object of the invention is to provide a method for screening for chemotherapeutic drugs and for monitoring the efficacy of a chemotherapeutic and intervention drugs.

It is a further object of the invention to provide a transgenic animal which has incorporated into its genome one or more copies of a nucleic acid sequence which encodes an epithelial protein which is an early marker for cancer. The incorporation of the nucleic acid sequence results in over-expression or expression of multiple forms or variants of the epithelial protein. The resulting transgenic animal is more prone to develop cancer and may develop cancer at an accelerated rate at one or more locations in the body. Such transgenic animals are useful for screening therapeutic drugs useful for treating or inhibiting cancer.

It is yet another object of the invention to provide an antibody reactive to an epithelial protein, peptide or variant thereof. Such antibodies are useful in diagnosis and treatment of cancer.

BRIEF DESCRIPTION OF DRAWINGS

These and other objects, features, and many of the advantages of the invention will be better understood upon a reading of the following detailed description when considered in connection with the accompanying drawings wherein:

FIG. 3 shows the full DNA sequence of human hnRNPB1 disclosed by Burd, C. G. et al *Proc. Nat'l Acad. Sci. USA* 86:9788–9792 (1989).

FIG. 4 shows the amino acid sequence of peptides sequenced from CNBr digest of purified 703D4 antigen, aligned with hnRNP-A2/B1. Alignment of CNBr-generated fragments of purified 703D4 antigen with predicted sequence of the hnRNP-A2/B1 (numbering for hnRNP-B1). Lower case letters (amino acids 3–14) denote the alternately-spliced exon missing in hnRNP-A2. Methionines subject to CNBr cleavage are denoted by • or *. Peptides commencing after a * methionine would be too small for visualization by Tricine SDS-PAGE (<2 kDa). Identical data were obtained from three separate purifications of 703D4 antigen. In each case two bands yielded the sequence AARPIISIDGRVV (SEQ ID NO: 1), and several variable minor bands were seen, suggesting partial CNBr cleavage possibly due to oxidized methionines.

FIGS. 5*a* through 5*f* show polymeric reversed phase HPLC purification of 703D4 antigen. 10 mm×10 cm Poros perfusion polymeric $C_{18}$ column was equilibrated with 5% acetonitrile/0.1% TFA (5*a*) and 5% methanol/1.1% HFBA (5*d*). Protein was eluted with a gradient of 5–100% acetonitrile (5A) and 5–100% methanol (5*d*) at a flow rate of 10 ml/min. Fractions were run on two identical SDS-PAGE gels and one stained with Coomassie blue (5*c*, 5*f*), the other transferred to PVDF for reaction with 703D4 antibody (5*b*, 5*e*). Positions of protein standards are shown on the right (43, 29, 18 and 6 kDa). In the a panels, note the separation of ampholytes, urea and the major protein from the protein of interest (fraction 15, 16 in 5*b* and fraction 34, 35 in 5*e*). Immunoreactivity positive fractions were pooled for additional purification.

FIGS. 6*a* through 6*c* show $C_4$ reversed phase HPLC purification of 703D4 antigen. 6*a*, c4 column, eluted with a gradient of 33–48% acetonitrile in 0.1% TFA. 6*b* and 6*c* shown Western blot and Coomassie blue analysis of eluted fractions, respectively (49, 32 and 18 kDa protein standards are on the right).

FIG. 7*a* shows the amino acid alignment of the peptides of the present invention with heterogeneous nuclear ribonucleoprotein B2 (hnRNP-A2 is denoted by Λ skipped area) •, * methionines; * peptides produced by CNBr at this Met too small for Tricine SDS-PAGE.

DETAILED DESCRIPTION OF THE INVENTION

Figure 7B:
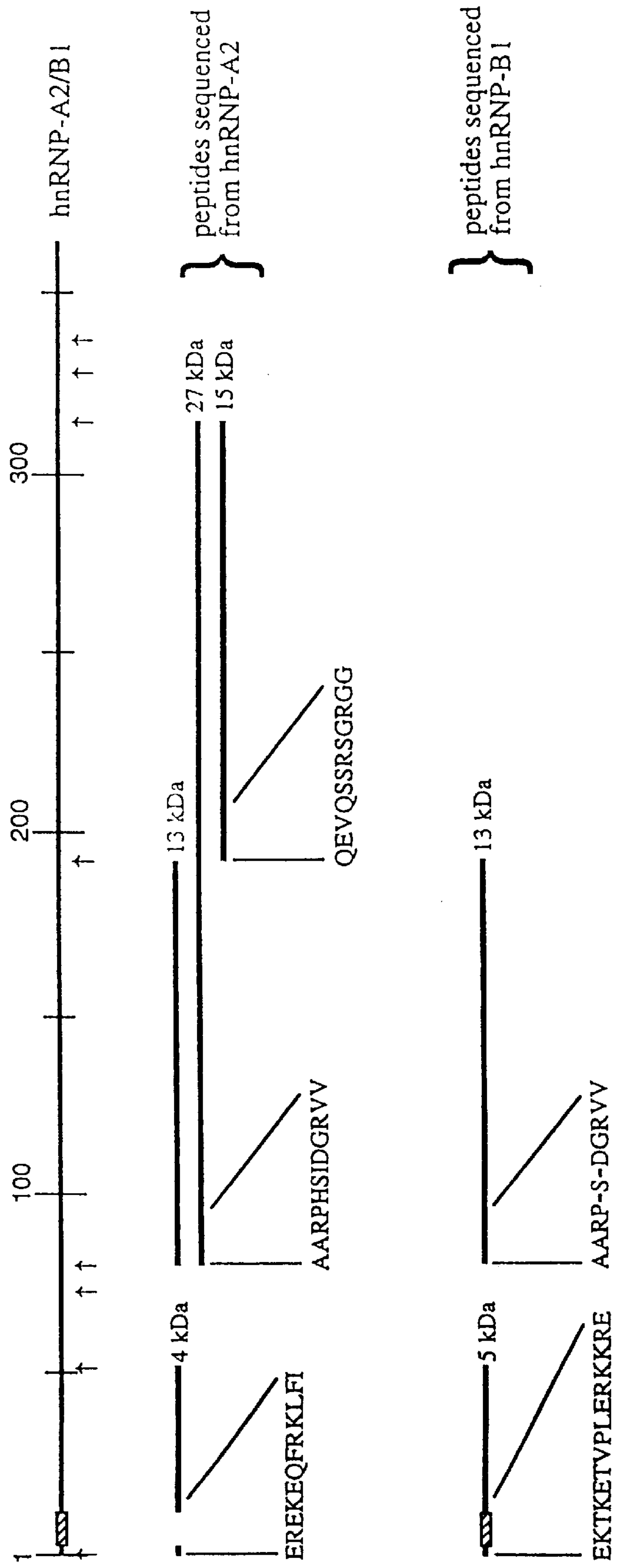
FIG. 7*b* shows the N-terminal amino acid sequences and approximate Mr of CNBr cleavage fragments of the purified 703D4 major (hnRNP-A2) and minor (hn-RNP-B1) antigens. Arrows indicate the positions of methionines within the protein, and the carrot indicates the site of alternately spliced exon differentiating hnRNP-A2 from B1. The exact methionine at which the 15 kDa and 27 kDa peptides terminates could not be determined from the SDS-PAGE analysis. All peptides which were not recovered are too small to be resolved from the migration front of the Tricine SDS-PAGE gel (<2.5 kDa).

The present invention is an isolated and purified protein, peptide and derivatives thereof as well as variants thereof which is an early detection marker for cancer. The protein, peptides and variants thereof are characteristically present in low levels from normal cells and are present in high levels from pre-cancer and most cancer cells. As used herein, variants include altered proteins that arise from DNA mutations, alternate exon splicing and post translational modifications. Expression of such variant proteins correlates with transformation of normal cells to a precancer or cancer cell.

Of particular interest is an 31 protein having a molecular weight of about 31 KDa to about 35 KDa and peptides and variants thereof isolated and purified from pre-neoplastic and neoplastic cells of the lung, colon, kidney, bone, breast, prostate, melanoma, myeloma and the like. The protein and peptides and variants thereof of the present invention are markers for epithelial cells which are committed to a pathway of transformation leading to development of lung cancer. A preferred protein and variant thereof is isolated from human lung cancer cells, in particular, non-small cell cancer cells.

The isolated and purified protein and variants thereof of the present invention comprises at least one of the following amino acid sequences, preferably more than one of the sequences:

```
AARPHSIDGRVV        (SEQ ID. NO.: 1);
QEVQSSRSGRGG        (SEQ ID. NO.: 2);
REKEQFRKLFI         (SEQ ID. NO.: 3);
EKTKETVPLERKKRE     (SEQ ID. NO.: 4);
AARPSDGRVV          (SEQ ID. NO.: 5);
EREKEQFRKLFI        (SEQ ID. NO.: 6).
```

In one embodiment, the protein, peptide and variants thereof are characterized by a molecular weight of about 4 kDa and comprises the amino acid sequence according to sequence I.D. No.: 3. In another embodiment the protein, peptide and variants thereof are characterized by a molecular weight of about 27 kDa and comprises the amino acid sequence according to sequence I.D. No.: 1. In yet another embodiment the protein, peptide and variants thereof are characterized by a molecular weight of about 13 kDa and comprises the amino acid sequence according to sequence I.D. No.: 1. In still another embodiment of the invention the protein, peptide and variants thereof are characterized by a molecular weight of 15 kDa and comprises amino acid sequence I.D. No.: 2.

In one embodiment, the protein, peptides and variants thereof, share partial amino acid sequence homology with at least one or more heterogenous nuclear ribonucleotide proteins (hn-RNP). The protein peptides and variants of the present invention may share partial amino acid sequence homology with one or more of the hn-RNP selected from the group consisting of hn-RNPA1, hn-RNPA2, hn-RNP-B1, hn-RNPB2, hn-RNPC1, hn-RNPC2 and hn-RNPC3. In a particular embodiment, the protein shares partial amino acid sequence homology with hn-RNP A2. In another embodiment, the protein shares partial amino acid sequence homology with hn-RNP B1. In a preferred embodiment of the present invention, the protein shares partial amino acid sequence homology with hn-RNP A2 and hn-RNP B1. By partial amino acid sequence homology is meant a protein, peptide or variant thereof having at least 70% sequence homology with at least one hn-RNP, preferably at least about 90% sequence homology, more preferably at least about 95% sequence homology with at least one or more hn-RNP.

In one embodiment the protein, peptide or variant shares sequence homology with the following amino acid sequence or portion thereof:

1 MEktletvplerkkREKEQFRKLFIG-GLSFETTEESLRNYYEQWGKLTDCVVMRDPASKR
61 SRGFGFVTFSSMAEVDAAMAAR-PHSIDGRVVEPKRAVAREESGKPGAH-VTVKKLFVGGIK
121 EDTEEHHLRDYFEEYGKWTIEIITDRQS-GKKRGFGFVTFDDHDPVDKIVLQKYRTINGH
181 NAEVRKALSRQEMQEVQSSRSGRGGNFG-FGDSRGGGGNFGPGPGSNFRGGSDGYGSGRGF
241 GDGYNGYGGGPGGGNFGGSPGYGGGRG-GYGGGGPGYGNQGGGYGGGYD-NYGGGNYGSGNY
301 NDFGNYNQQPSNYGPMKSGNFGGSRNMGGP YGGGNYGPGGSGGSGGYGGRSRY(SEQ ID NO. 7)

In another embodiment, the protein peptide or variant thereof shares sequence homology with the following amino acid sequence or portion thereof:

1 MEREKEQFRKLFIGGLSFETTEESL-RNYYEQWGKLTDCVVMRDPASKR
49 SRGFGFVTFSSMAEVDAAMAAR-PHSIDGRVVEPKRAVAREFSGKPGAH-VTVKKLFVGGIK
109 EDTEEHHLRDYFEEYGKIDTIEUTDRQS-GKKRGFGFVTFDDHDPVDKIVLQKYHTINGH
169 NAEVRKALSRQEMQEVQSSRSGRGGNFG-FGDSRGGGGNFGPGPGSNFRGGSDGYGSGRGF
229 GDGYNGYGGGPGGGNFGGSPGYGGGRG-GYGGGGPGYGNQGGGYGGGYD-NYGGGNYGSGNY
289 NDFGNYNQQPSNYGPMKSGNFGGSRNMGGPY GGGNYGPGGSGGSGGYGGRSRY(SEQ ID NO. 8)

Variants include but are not limited to proteins and peptides that vary in amino acid sequence by one or more than one amino acid, preferably do not vary by more than 10 amino acids, preferably not more than 5 amino acids, more preferably not more than 1–3 amino acids. The amino acid change may be conservative substitutions, deletions and the like. Examples of these amino acid changes include but are not limited to alteration of aromatic amino acid to alter DNA/RNA binding sites; methylation of arginine, lysine or histidine including $N^G$, $N^G$-dimethyl-arginine near the COOH terminus; phosphoserines or phosphothreonine, blocked N-terminus glycosylation, and the like. Variants also encompass alternate mRNA splice forms of the protein or peptides.

Also included as variants are proteins and peptides having one or more post-translational modifications of amino acids. Examples of post-translational modifications include but are not limited to glycosylation, phosphorylation, methylation, ADP ribosylation and the like. In one embodiment, the variant has a post-translational modification of a methylation on the N-terminal amino acid or phosphorylations of serines and threonines. In another embodiment, the variant has a post-translational modification of C-terminal glycines for affecting protein binding.

Also encompassed by the term variant, are derivatives of the proteins, peptides and post-translational modified proteins and peptides that may have other constituents attached thereto such as radiolabels, biotin, fluorescein and chemiluminescent labels and the like.

Inhibitory protein or peptide analogs are also encompassed in the invention. Such inhibitory protein or peptide analogs are capable of competitively inhibiting the binding of the epithelial protein to its binding site on RNA.

The identification of the 703D4 early lung cancer detection antigen as sharing amino acid sequence homology with hnRNP A2/B1 is provocative in light of the emerging knowledge about the hnRNP group of proteins (Burd and Dreyfuss, *Science,* Vol. 265 (July 29) pp. 615–621, 1994). The family of hnRNP have roles in RNA processing, including pre-mRNA exon splicing and splice site choice, and also in transcription, DNA replication, and recombination (reviewed in Dreyfuss et al., *Ann Rev Biochem.,* Vol. 62, pp 289–321, year 1993. Some hnRNPs are involved in shuttling mRNA from the nucleus to the cytosol, which is consistent with both our immunohistochemical localization reported previously and subcellular fractionation. A variety of post-translational modifications have been reported for members of the hnRNP family.

Post-translational modifications of the epithelial protein, peptide or variants thereof of the present invention are identified by methods known in the art such as two dimensional electrophoresis, reverse-phase APLC (Karn, J. et al. *J. Biol. Chem.* 252, No. 20, pp 7307–7322, 1977; Anderson, N. L. *Electrophroesis* 12, pp. 907–930, 1991; Boffa, L. C. et al. *Biochemical and Biophys. Res. Commun.,* 74, No. 3, 1977; Williams, K. R. et al. *Proc. Natl. Acad. Sci USA,* vol. 82, pp. 5666–5670, 1985; Kumar, A. et al. *J. Biol. Chem.,* vol. 261, No. 24, pp. 11266–11273, 1986; Medzihradsky, K. P. et al. *Am. Soc. Mass. Spectrom,* vol. 5, pp. 350–358, 1994). One method uses two dimensional gels analysis. A purified epithelial protein peptide or variant with and without enzymatic treatment is electrophoresed in the first dimension. The second dimension is conducted under a pH gradient of about pH 8 to about 9.5 (Anderson *Electrophoresis* 12:907, 1991). The protein peptide or variant may be detected by methods known in the art such as protein staining, radiolabelled metabolic labels, antibody and the like. The shift in migration pattern is indicative of a post-translation modification.

Post-translational modifications are also determined using specific enzymes such as phosphatase, glucosidase and the like to treat samples separated by two dimensional gel electrophoresis or by electrospray API-mass spectroscopy (Medzihradsky, *Am. Soc. Mass. Spec.,* 5:350, 1994) and the molecular weight of the treated samples compared with non-treated samples.

Figure 10:
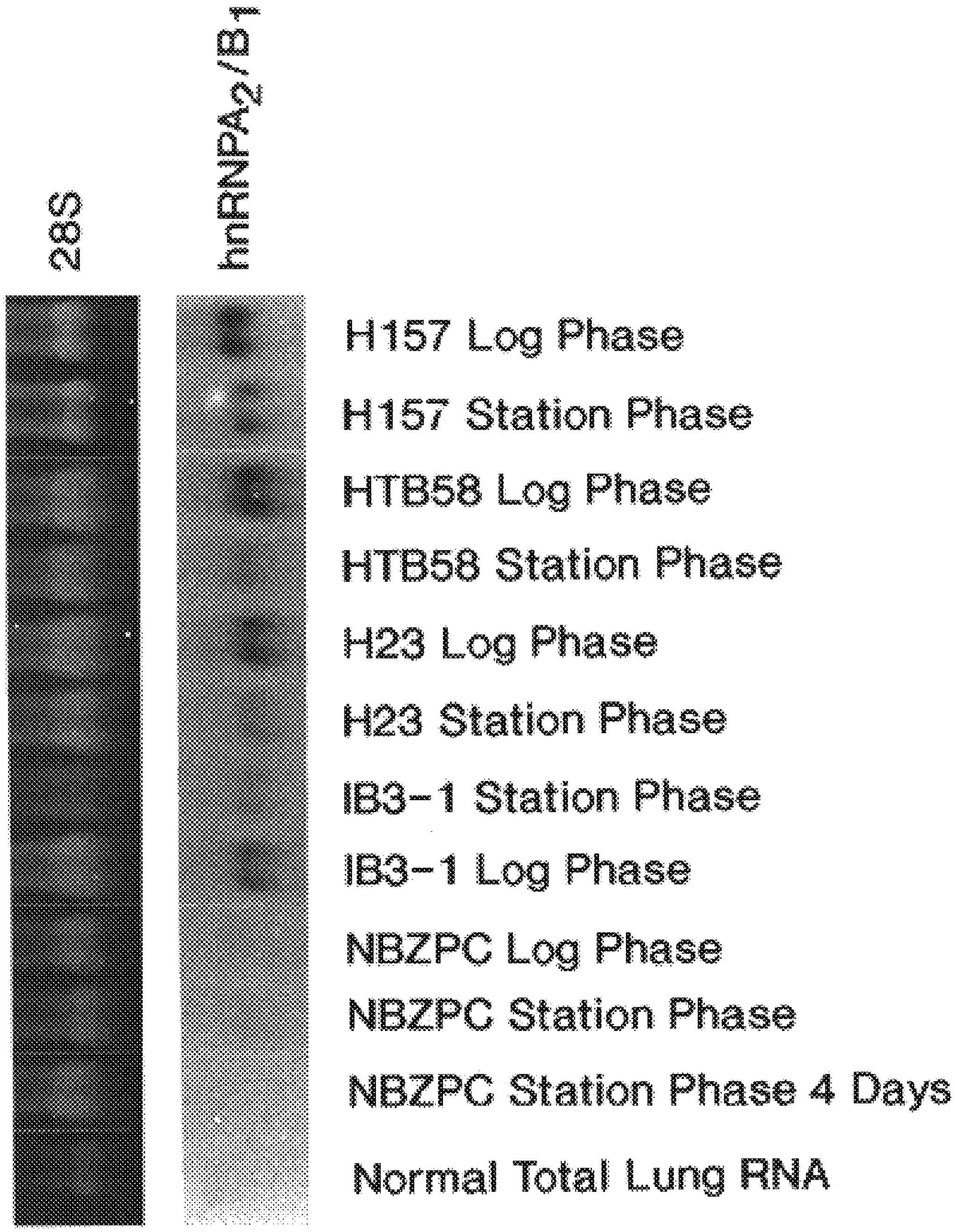
FIG. 10 shows proliferation-dependent control of hnRNP-A2/B1 expression. Northern blot hybridization with probes specific for hnRNP A2/B1 to 10 μg of total RNA from NSCLC (H157, HTB58 H23); a transformed bronchial epithelium cell line (IB3-1) and normal bronchial epithelium primary culture (NBEPC) log phase and station phase. Quantification of the loaded RNA was obtained by ethidium bromide staining of 28s rRNA (EtBr).

In one embodiment, the invention demonstrates deregulation and overexpression of the an early lung cancer epithelial protein in cancer cell lines and in transformed bronchial epithelial cells compared to short term, normal primary bronchial epithelial cultures. This data parallels previous work on the closely related molecule hnRNP-Al which showed deregulation of expression in transformed cells including fibroblast cells (Biamonti, *J. Mol. Biol.,* Vol. 230, pp 77–89, 1993). In transformed cell lines including tumor cell lines, high level of hnRNP-A1 expression is maintained in cultures which have reached stationary phase, whereas normal primary fibroblast cultures express hnRNP-A1 only during the logarithmic phase of cell growth (FIG. 10).

The protein and variants thereof may be isolated from natural sources or may be chemically synthesized or recombinantly produced by techniques known in the art. Technique for chemical synthesis are described in J. M. Steward and J. D Young, "Solid Phase Peptide Synthesis", W. H. Freeman & Co., San Francisco, 1969; M. Bodansky, et al. "Peptide Synthesis", John Wiley & Sons, Second Edition, 1976 and J. Meienhofer, "Hormonal Proteins and Peptides" Vol. 2, p.46, Academic Press, New York, 1983 and E. Schroder and K. Kubke, "The Peptides", Vol. 1, Academic Press, New York, 1965.

The protein, peptides and variant thereof is at least about 90% pure, preferably at least about 95% pure, more preferably greater than 95% pure.

The present invention also encompasses compositions comprising the epithelial protein, peptides, and variants thereof which are early markers for precancer and cancer each as separate molecular species or in the form of complexes. The composition comprises one or more proteins, peptides and variants thereof have at least one amino acid sequence defined by SEQ ID NOS: 1–6 or portions thereof. In one embodiment, the composition comprises one or more proteins, peptides and variants thereof that share amino acid sequence homology with at least one heterogeneous nuclear ribonucleoprotein. In the case of complexes, the complex of protein, peptides and variants thereof may be held together by covalent or noncovalent bands. One or more protein and variants thereof may form the complex. In one embodiment of the complex comprises at least one protein, peptide or variant thereof that shares amino acid sequence homology with hnRNP A2. In another embodiment the complex comprises at least one protein, peptide or variant thereof that shares amino acid sequence homology with hnRNP B1. In yet another embodiment, the complex comprises a protein, peptide or variant thereof that shares amino acid sequence homology with hnRNP A2 and a second protein, peptide or variant thereof that shares amino acid sequence homology with hnRNP B1.

The present invention provides methods of purifying an epithelial cancer protein, peptides and variants thereof, which are early markers for cancer, that achieves high levels of purification. The methods described herein achieve at least 20,000 fold purification, preferably 25,000 fold purification, more preferably greater than 25,000 fold purification compared to the source material.

The method of purification takes steps to prevent or inhibit degradation of the protein, peptide or variant thereof during the purification process. For successful purification of the epithelial protein, peptide or variant a large amount of starting material is preferred. In one embodiment, the purification was made possible by the use of enormous numbers of p31 expressing tumor cells approximately greater than about $2.5\times10^{11}$ cells.

The protein, peptides and variants thereof may be used in diagnostic methods and in in vitro assays to detect the presence of a similar protein, peptide and variants thereof present in a biological sample. The assays allow for early detection of pre-neoplastic and neoplastic cells and in defining the process of carcinogenesis.

In one embodiment, the isolated and purified protein, peptide or variant thereof is useful in immunoassays for the detection of the corresponding protein or variant thereof. The immunoassays are qualitative and quantitative. The immunoassays are useful in detection of precancer and cancer cells in which an increase in the quantity of the epithelial protein, peptide or variant thereof is indicative of precancer and cancer. Conversely, the immunoassays are useful in monitoring the efficacy of cancer treatment or intervention in which the absence or decrease in the quantity of the epithelial protein, peptide or variant thereof recovered from a patient undergoing treatment or intervention is an indication of an efficacious treatment.

Immunoassays of the present invention may be a radioimmunoassay, Western blot assay, immunofluorescent assay, enzyme immunoassay, chemiluminescent assay, immunohistochemical assay and the like and may be performed in vitro, in vivo or in situ. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, *J. Clin. Chem. Clin. Biochem.,* 22:895–904. Biological samples appropriate for such detection assays include, but are not limited to, cells, tissue biopsy extracts, whole blood, plasma, serum, sputum, cerebrospinal fluid, pleural fluid, urine and the like.

In one embodiment for detection using a competitive immunoassay, test sample suspected of containing the epithelial protein, peptide or variant thereof is reacted in fluid phase with an antibody known to be reactive with the protein, peptide or variant thereof to form an antigen-antibody complex. This fluid phase is then placed on a solid phase reagent having surface bound protein, peptide or variant of the invention. Any antibody which is not in the form of a complex is free to bind to the surface bound protein, peptide or variant thereof. The amount of antibody bound to the surface is determined by methods known in the art. The solid surface reagent can be prepared by known techniques for attaching protein to solid support material. These attachment methods include but are not limited to non-specific adsorption of the protein or variant to the support or covalent attachment of the protein or variant to the solid support. In one embodiment, the antibody is 703D4 disclosed in U.S. Pat. No. 4,569,788.

The label may be an enzyme which is detected by incubating the solid support in the presence of a suitable fluorimetric or colorimetric reagent. Other detectable labels may be used, such as radiolabels or colloidal gold and the like.

The protein, peptide and variants thereof may be prepared in the form of a kit, alone, or in combination with other reagents such as antibodies, for use in the immunoassay.

The protein, peptide and variants thereof may be used to elicit specific antibodies and antigen binding fragments thereof that are immunoreactive with the epithelial protein, peptide or variant thereof. Of particular importance are antibodies or antigen binding fragment thereof that recognize an epitope which is associated with transformation of a normal cell to a pre-cancer cell. The epitope is not present or is present in low amounts in normal cells and is highly expressed in precancer and cancer cells. In one embodiment the antibody or antigen binding fragment thereof reacts with an epithelial protein, peptide or variant thereof having a post-translational modification, wherein said post-translational modification is indicative of a precancer or cancer cell. The antibodies may be produced by methods disclosed in U.S. Pat. No. 4,569,788 or by other methods known in the art. Such antibodies are useful in immunoassays to detect the epithelial protein and to detect post-translational modifications of the protein. The antibodies or antigen binding fragment thereof are useful as intermediate end-point markers in determining the efficacy of a cancer treatment or intervention.

The invention provides a purified and isolated DNA molecule comprising all or part of the nucleic acid sequence that encodes an epithelial protein, peptide or variant thereof, whose expression or overexpression is indicative of a pre-cancer or cancer cell.

Amplifications were done with gene libraries from 3 sources including two lung cancer cell lines, NCI-H157 and NCI-H720, which were the two cell lines used to purify the antigen, p31. As a control, the gene from a short term culture of normal bronchial epithelial cells was also amplified (Clonetics NHBE 2129 cells, San Diego, Calif.). These genes were then inserted into a pCR II vector and grown up in *E. coli* using the original TA Cloning® Kit, Cat. No. C2020-03 Lot No. 411208 from Invitrogen Corp., San Diego, Calif. The *E. coli* transformation cultures from the three different sources of hnRNP genes A2/B1 with plasmids containing the hnRNP genes were deposited under conditions of the Treaty of Budapest at the American Type Culture Collection, 12301 Parklawn Dr., Rockville, Md. on Oct. 2, 1995 under Accession Numbers ATCC 69906 (*E. coli* NBER NP1c, normal), ATCC 69907 (*E. coli* 157RNPc 1B), and ATCC 69908 (*E. coli* 720RNPc1A). The sequence for the primers used to amplify the entire hnRNP genes was as follows:

CTA CAG CGC CAG GAC GAG T (SENSE)

CCC ATG GCA AAT AGG AAG AA (ANTI SENSE)

These primers allowed for the amplification of the full length of both the A2/B1 genes.

Figure 11A:
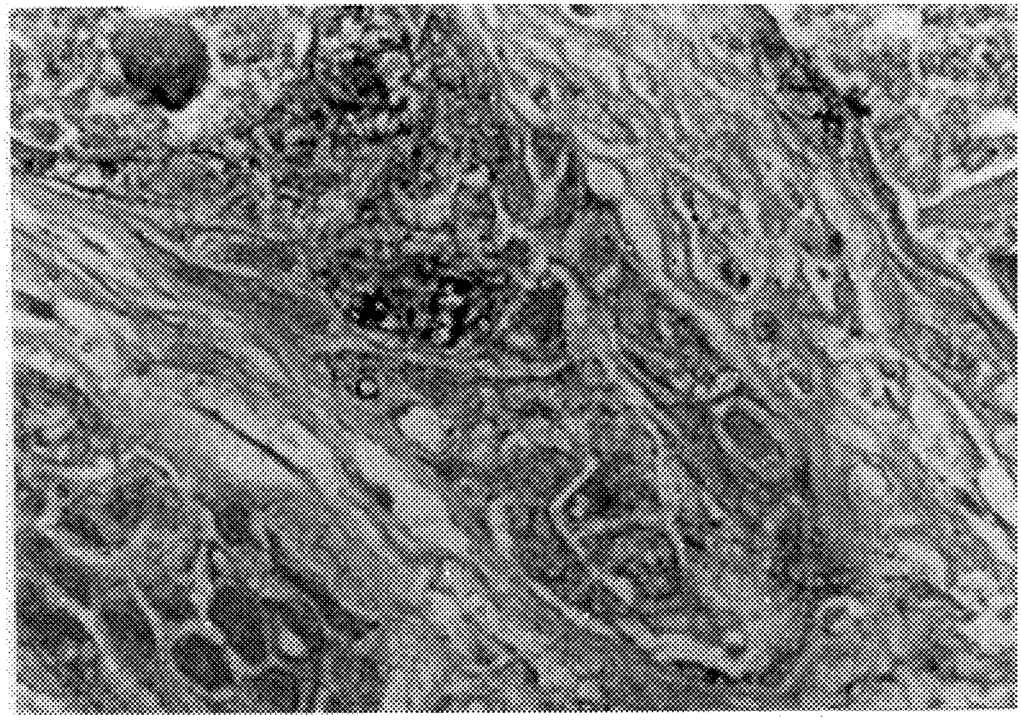
FIGS. 11A through 11C shows P31 expression pattern in primary NSCLC 6A) Focal cytoplasmic p31 staining in squamous cell carcinoma (Immunohistochemical staining, X360). WP) Diffuse p31 expression with granular staining in an adjacent area at pulmonary adenocarcinoma. Note perinuclear staining pattern, inset. (Immunoperoxidase, X360). 11C) Pulmonary adenocarcinoma with membranous expression pattern (Immunoperoxidase, X270).
Figures 1, 11B:
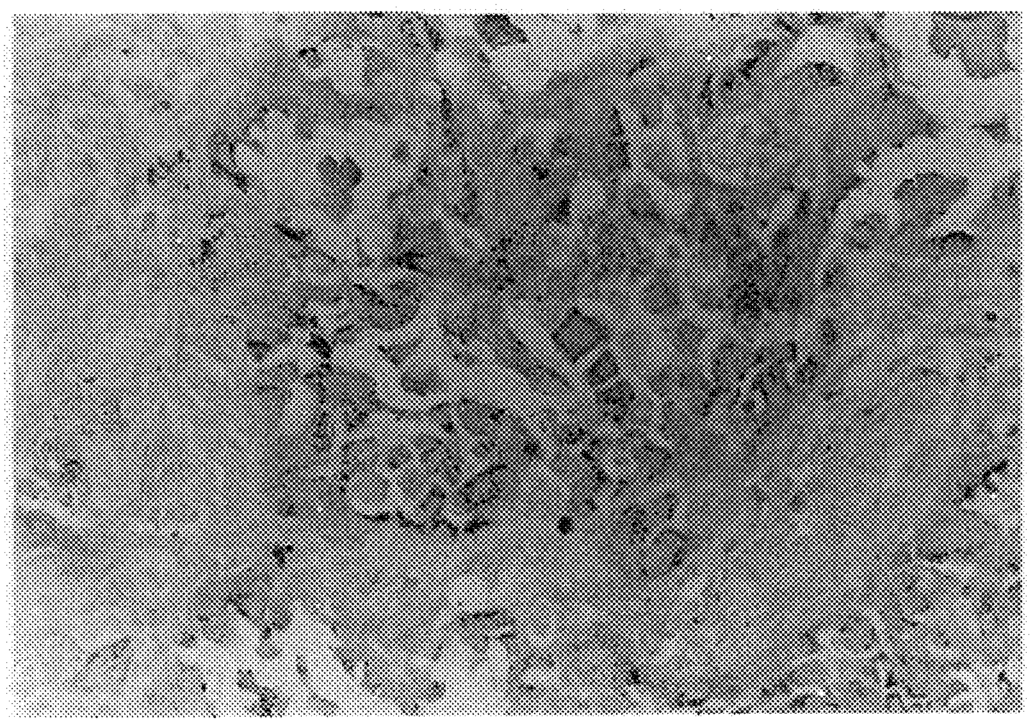
FIG. 1 shows the DNA coding sequence of heterogenous ribonucleoprotein Al (hnRNP) and hnRNP A2.
Figures 2, 11B:
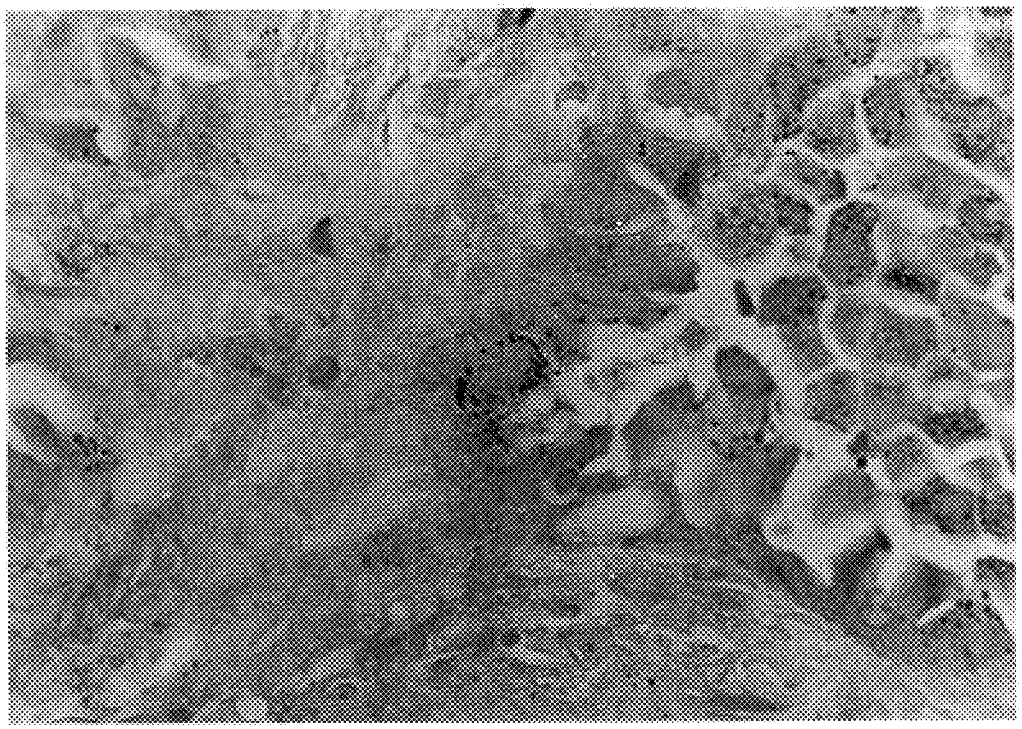
FIG. 2 shows the full DNA sequence of human hnRNPA2 disclosed by Burd, C. G. et al *Proc. Nat'l Acad. Sci. USA* 86, 9788–9792 (1989).

In one embodiment the isolated DNA or portion thereof encoding the epithelial protein is substantially homologous to portions of the sequences disclosed in FIGS. 1–3. It is anticipated that the nucleic acid sequence of the present invention varies to a certain extent from that depicted on FIGS. 1–3. The sequences on FIGS. 1–3 were derived from a cDNA clone from a malignant human osteosarcoma cell line. The present invention encompasses the DNA or portion thereof isolated from normal cells and premalignant cells.

Due to the degeneracy of the genetic code, it is to be understood that numerous choices of nucleotides may be made which will lead to a DNA sequence capable of directing the production of the instant epithelial protein, peptide and variants thereof. As such, DNA sequences which are functionally equivalent to the sequence set forth herein or which are functionally equivalent to sequences which would direct the production of analogs of the epithelial protein are intended to be encompassed within the present invention.

The present invention also provides a recombinant DNA molecule and a vector capable of being propagated and expressed in a prokaryotic or a eukaryotic host cell. Expression vectors suitable for use in the invention comprise at least one expression control element operationally linked to the nucleic acid sequence or part thereof. Expression control elements are inserted in the vector to control and regulate the expression of the nucleic acid sequence. Examples of expression control elements include, but are not limited to, the lac system, operator and promoter regions of phage lambda, yeast promoters, and promoters derived from vaccinia virus, adenovirus, retrovirus, or SV40. Other operational codons, polyadenylation signals, and other sequences required for the appropriate transcription and subsequent translation of the nucleic acid sequence in a given host system are present. In addition, it is understood that the expression vector contains any additional elements necessary for the transfer and subsequent replication of the nucleic acid containing expression vector in the host system. Examples of such elements include, but are not limited to, origins of replication and selectable markers. Such expression vectors are commercially available or are readily constructed using methods known to those in the art (eg. F. Ausubel et al, 1987 in: "Current Protocols in Molecular Biology", John Wiley & Sons, New York, N.Y.). Examples include, but are not limited to vaccinia virus vectors, adenovirus vectors, herpes virus vectors and baculovirus vectors. The recombinant expression vector containing all or part of the nucleic acid sequence encoding the epithelial protein, peptide or variant thereof is transformed, transfected or otherwise inserted into a host organism or cell. The host cells transformed with the nucleic acid sequence encoding the epithelial protein of the invention include eukaryotic cells such as animal, plant, insect, algae, and yeast cells, and prokaryotic cells such as *E. coli, B. subtilus* and the like. Preferred eukaryotic host cells include but are not limited to, COS cells, CHO cells, insect cells, bronchial epithelial cells, especially eukaryotic cells that allow for post-translational modifications of the expressed epithelial protein, peptide or variants thereof. The means by which the vector carrying the nucleic acid sequence may be introduced into a cell include, but is not limited to, microinjection, electroporation, transduction or transfection using DEAE-dextran, lipofection, calcium phosphate or other procedures known to the use skilled in the art (Sambrook et al, 1989, in: Molecular Cloning. A Laboratory Manual", Cold Springs Harbor Press, Plainview, New York).

The expressed recombinant epithelial protein, peptides or variants thereof may be detected by methods known in the art, including but not limited to, Coomassie blue staining, silver staining and Western blot analysis using antibodies specific for the epithelial protein, peptides or variants thereof as described herein.

The recombinant epithelial protein, peptides and variants thereof of the present invention may be isolated and purified using the protocol described herein including anion exchange chromatography, preparative isoelectric focusing, polymer-based $C_{18}$ HPLC and analytic $C_4$ HPLC.

The genes or gene products of epithelial protein, peptides or variants thereof can be detected in mammalian biological samples such as blood, serum, stool, urine, amniotic fluid, sputum, bone tissue biopsy specimens and the like. Of particular interest is the detection of an epithelial protein, peptide or variant thereof having sequence homology with at least one hnRNP gene or gene product. By screening body samples, early detection of precancer cells may be achieved and in turn early treatment may be provided to the mammal to inhibit or prevent transformation of the precancer cells to a cancer cells. In addition, the efficacy of chemotherapy and/or radiotherapy can be monitored by testing of body samples for the altered expression or overexpression of the genes or gene products.

A predisposition to cancer may be ascertained by testing mammalian biological samples for altered expression and/or overexpression of a gene encoding the epithelial protein, peptide or variants thereof. This predisposition can be determined by testing DNA or RNA from cells removed from any tissue or fluid from the mammal to detect overexpression and/or variant expression products of the epithelial protein, peptide or variants thereof. The method of diagnosis of the present invention is applicable to any cancer in which the epithelial protein, peptide or variants thereof have a role in tumorigenesis. Of particular interest is lung cancer, bone cancer, renal cancer, breast cancer, uterus, prostate, colon, melanoma, myeloma, head cancer, neck cancer and the like.

In the method of diagnosing a genomic nucleic acid sequence isolated from a biological sample taken from a mammal is contacted with the nucleic acid sequence or portion thereof encoding an epithelial protein which is an early marker for cancer, under conditions that allow hybridization between the sequences and detecting the hybridized sequences. The presence of a genomic nucleic acid sequence or the presence of an altered genomic nucleic acid sequence as compared to a normal nucleic acid sequence is indicative of precancer or cancer in the mammal. The increased presence of the DNA, mRNA and/or alternate splice forms of the mRNA in the biological sample is indicative of precancer and cancer in the mammal.

The oligonucleotides of the present invention are useful in detection of the gene and detection of alterations or mutations in the gene encoding the epithelial protein. The oligonucleotides may also be used to monitor the response of epithelial cells to cancer treatment and intervention and as such are important intermediate endpoint markers.

In another aspect of the invention, oligonucleotide primers are useful for the synthesis of all or a portion of the gene encoding the epithelial protein, peptide or variants thereof using the polymerase chain reaction. A pair of single stranded DNA primers can be annealed to sequences within or surrounding a gene in order to amplify DNA synthesis of the gene. The polymerase chain reaction is known in the art as described by Saiki et al., 1988 *Science* 239:487–491; U.S. Pat. No. 4,683,202 and U.S. Pat. No. 4,683,195 and *Methods in Enzymology,* 155:335–350, 1987. Specific primers which can be used to amplify the gene include but are not limited to:

```
5'GAGTCCGGTTCGTGTTCGTC3'        (SEQ ID NO.: 11);
5'TGGGCTCTCATCCTCTCCTATTA3'     (SEQ ID NO.: 12);
5'CTACAGCGCCAGGACGAGT3'         (SEQ ID NO.: 13);
5'CCCATGGCAATAGGAACAA3'         (SEQ ID NO.: 14);
TGTTCTGTFACCTCTGGGCTCTCA        (SEQ ID NO.: 15)
```

and the like.

Specific pairs of primers may be used to clone the cDNA encoding the epithelial protein, peptide and variants of the present invention. Examples of primer pair that may be used to clone the cDNA using PCR include but are not limited to SEQ ID Nos: 11 and 12; SEQ ID Nos: 13 and 14; SEQ ID Nos: 11 and 15, and the like.

The gene for hnRNP A2 as well as for the gene for B1 have been recovered from a PCR reaction with a library of genes created from the cell line NCI-H157, NCI-H720 as well and a short term culture of bronchial epithelial cells. These genes have been inserted into a vector (pCRII) and expressed in *E. coli.* The presence of the appropriate gene product has been confirmed by PCR with a set of conserved hnRNP primers (used a Sense primer 5'-3', GCTCGGCTGCGGGAAATC (SEQ ID NO: 23) and anti sense primer, TAAGCTTTCCCCATTGTTCGTAGT (SEQ ID NO: 20) with an expected 146 bp PCR product). The plasmids containing these genes are on deposit at ATCC under the conditions of the Treaty of Budapest. The differences in the gene sequences from the cancer cell lines relative to the gene obtained from normal bronchial cells were determined. It was found that the gene from all sources were highly homologous.

In addition, the protein product may be expressed of the hnRNP A2/B1 gene from the cancer cell line NCI-H157 and NCI-H720 in an expression system that has the metabolic machinery to process the post translational changes in the gene product. The final protein is compared with the product of the hnRNP A2/B1 gene product from the normal bronchial cell line. The protein is purified from those different cell sources, cyanogen bromide digestion performed and then the products analyzed using one or two dimensional gel electrophoresis or mass spectrometry. Any difference in the gene product from NCI-H157 or H720 compared to the normal source of the hnRNP could be due to a critical mutation.

Also, combinations of oligonucleotide pairs based on the nucleic acid sequence encoding the epithelial protein or portion thereof may be used as PCR primers to detect mRNA in a biological sample using the reverse transcriptase polymerase chain reaction (RT-PCR) process for amplifying selected RNA nucleic acid sequences as detailed herein as well as in Ausubel et al, 1987 In: "Current Protocols In Molecular Biology" Chapter 15, John Wiley & Sons, New York, N.Y. The oligonucleotides can be synthesized by automated instruments sold by a variety of manufacturers.

The present invention also encompasses in situ PCR and in situ RT-PCR for detection of DNA and RNA encoding the epithelial protein, peptides and variants thereof. The technique is preferred when the copy number of a target nucleic acid is very low, or when different forms of nucleic acids must be distinguished. The method is especially important in detecting and differentiating precancer and cancer cells from normal cells. The method is also useful in detecting subsets of epithelial cells destined to become cancer cells. Confirmation of in situ PCR product identity is accomplished by in situ hybridization with a nested $^{32}$P-labeled probe or by examining the products using Southern blot analysis to corroborate predicted base pair size. Coordinate transcriptional/translational expression is demonstrated by sequential in situ RT-PCR/immunohistochemical analysis on serial tissue sections.

Several sets of probes have been used for expression analysis of hnRNP in tissues and cells and shown similar results for all of the antisense vs. sense probes regardless of how the hnRNP probes were generated. The first set of probes were constructed by inserting the hnRNP A2-PCR product (generated from the lung cancer cell line NCI-H720) into a pCR II vector (Invitrogen). To generate the antisense probes, an EcoRV digestion was performed yielding a 1.1 kb product driven from a Sp6 promoter. For the sense probe, the same construct was used but was digested with Kpn1 and generated a 1.1 kb product driven by a T7 product.

Additional constructs were generated by digesting the full length hnRNP A2 constructs with Dra III to generate a 0.8 kb sense probe driven by a T7 promoter. The antisense probe was generated digesting the full length hnRNP A2 antisense construct with Nde I, yielding a 0.7 kb driven by a T7 promoter.

Another set of probes using the PCR sequence derived for the lung cancer cell line was generated using a Dra III digestion. This yielded two nucleotides products (1.2 kb T7 and 3.8 kb Sp6) which were gel purified, then in vitro transcribed in an in vivo transcription system (DIG RNA labeling kit, Boehringer Mannheim) to yield a 0.7 kb sense probe driven by T7 promoter. The other gel product was also transcribed and yielded a 0.4 kb anti sense probe driven by a Sp6 promoter.

For another set of probes, the full length hnRNP A2 insert referenced in GenBank was used. This full length hnRNP A2 gene sequence was inserted into a pcDNA 3 vector (Invitrogen). For the sense probe, the construct was digested with EcoRV to yield a 1.8 kb product driven by a 17 promoter. For the antisense probe the same construct was digested with BamH1, yielding a 1.6 kb product driven by Sp6 promoter.

All of the probes are useful for detecting hnRNP mRNA in cells, tissues and extracts in assays such as in situ hybridization and the like.

The present invention encompasses a computerized method for generating a discriminant function which is predictive of the development of cancer. The method utilizes image analysis to identify one or more parameters unique to an atypical or abnormal cell such as a cancer or precancer cell as compared to a normal or typical cell. Using computer analysis the unique parameters are identified from which a discriminant function is derived. The discriminant function is useful in predicting individuals who will ultimately develop cancer. The method is not restricted to any particular assay, as it is useful in any assay in which an image from a biological sample may be acquired for computer-assisted image analysis. In one embodiment, the image is a densitometry image. In another embodiment, the image is a fluorescence image.

The present invention also provides a method of computer-assisted determination of cancer and precancer in a mammal, preferably a human. The method detects qualitative and quantitative differences in expression of hn-RNP mRNA in biological samples such as cells, extracts and tissues.

In one embodiment the method of computer-assisted determination of cancer and precancer utilizes image densitometry, preferably dual-wavelength image densitometry to determine cells, extracts or tissue positive for hn-RNP mRNA. In the method, at least one labelled probe is used to hybridize with the hn-RNP mRNA present in the cell, extract or tissue. Cells, extracts or tissue are illuminated with a wavelength of light appropriate for the label used.

A second label may optionally be employed in the method. The second label does not hybridize with hn-RNP mRNA. The second label may be employed to distinguish structures within the cell, extract or tissue. One such label is a chromogen, including but not limited to hematoxylin blue and the like. In the case where two labels are used, an appropriate wavelength for each label is used.

In one embodiment, the appropriate wavelength is provided by a light source such as Koehler illumination. The light source is used to illuminate the biological sample so that an optical image acquiring means may collect a video image of the biological sample. The video image gathering means connects the video image of the biological sample into an analog electronic signal representative of the image.

The video image means, such as a video camera, may be any suitable technology which receives light as an input and provides a standard analog television video frame formatted output signal. In one embodiment, the video image means is a high resolution video camera from Hamamatsu Photonic Systems (Japan). The standard analog television video frame format signal from the video image gathering means is provided to the input of a programmable analog-to-digital converter as are known in the art. The converter converts the analog video signal from the video image gathering means into digital values. In one embodiment converter is a digital image processor, the Metamorph v2.0 from Universal Imaging, West Chester, Pa.).

A cell, extracts or tissue positive for hn-RNP mRNA may be determined visually by direct inspection of the image by an operator or by computer detection. In the case of computer-assisted determination of positive cells for hn-RNP mRNA, a discriminant function is used to calculate a positive cell, extract or tissue. The computerized determination allows the assay to determine precancer in a subject before the subject has any clinical manifestation of cancer. In one embodiment, a discriminant function value of about zero, or a value less than zero of a test biological sample taken from an individual with no clinical manifestations of cancer is predictive that the individual will develop cancer. The method of computer-assisted detection of hnRNP mRNA of the present invention allows for high accuracy in predicting the probability that a subject who will go to develop cancer. The method provides an accuracy of at least about 80% or greater in predicting those subjects who will develop cancer. In one embodiment, the level of accuracy is about 100%. This method allows for early detection of individuals at risk for developing cancer and provides an opportunity for continued monitoring and early treatment of the individual to prevent or inhibit the cancer.

Overexpression of the genes and the resultant overactivity of the gene product may contribute to deregulation of cell growth and neoplasia. Therefore, the present invention also provides antisense oligonucleotides which may be particularly useful in specifically regulating the expression of the gene encoding the epithelial protein.

As used herein, antisense therapy refers to administration or in situ generation of DNA or RNA oligomers or their derivatives which bind specifically to a target nucleic acid sequence. The binding may be by conventional base pair complementarily, or, for example, in the case of binding DNA duplexes, through specific interactions in the major groove of the double helix. By specifically binding to its target DNA or RNA, the function of DNA or RNA is inhibited or suppressed.

The antisense oligonucleotides of the present invention may vary in the number of nucleotide residues and may range from about 3 to about 100 nucleotide residues, preferably ranging from about 3 to about 50 nucleotide residues, more preferably from about 3 to about 25 nucleotide residues. In one embodiment the oligonucleotide has less than about 20 nucleotide residues. In another embodiment, the oligonucleotide has about 15 to about 20 nucleotide residues.

Antisense oligonucleotides of the present invention are constructed to prevent the expression of the epithelial protein, peptide or variant thereof that is a marker for early detection of cancer. Antisense oligonucleotides of the invention are nucleotides that bind and prevent or inhibit the transcription and/or translation of the nucleic acid encoding the epithelial protein. Of particular interest are antisense oligonucleotides that bind and prevent or inhibit the transcription and/or translation of one or more of secondary structures analogous to the structures of hn-RNP as defined by Burd, C. G. et al. *Science,* vol. 265, pp. 615–621, 1994, of Arginine-rich motif, RGGbx, α2, TI, and β4 regions of hn-RNP.

hnRNP A2/B1 have been implicated in a variety of cellular functions that could be important in the process of carcinogenesis. These functions include the regulation of alternative splice site switch activity, RNA (DNA)-protein interactions, and RNA (DNA) annealing. In particular, hnRNP A/B proteins are major nuclear proteins binding with high affinity to teleomeric DNA repeats $(TTAGGG)_n$ and to the RNA equivalent $(UUAGG)_n$. Anti sense strategies to modulate the gene coding region for the part of the hnRNP A/B protein involved in splice site regulation or interactions with telomeric binding would be steps to inhibit the role of hnRNP A/B proteins in progressive carcinogenesis. Targets for anti sense strategies include the G domain as this has major effect on hnRNP function. This regions is largely comprised of repetitive, imperfect iterations of the motif $(GN^{F}{}_{Y}GG^{S}{}_{G}RG)$ (n=12). This glycine-rich region of the hnRNP molecule greatly effects the protein functions such as nucleotide binding including the interaction with the telemeric regions. (Ishikawa, F et al *Mol. Cell. Biol.* Vol. 13, 4301, 4310, 1993; McKay, S. J. et al *Nucleic Acids Res.* Vol. 20:6461–64, 1992). Anti sense strategies to inhibit cancer would inhibit the translation of these hnRNP regions.

These same regions that are critical to the role of the hnRNP A2/B1 genes to carcinogenesis would also be rational targets for developing peptide antagonists to block the function of these two gene products. The peptide antagonists would target the comparable regions of hnRNP protein that has just been discussed for the hnRNP gene.

The antisense oligonucleotides comprise a nucleic acid sequence which is anticomplementary to the nucleic acid sequence encoding the amino acid sequences: ATVEEVDAAMNARPHKVDGRVVEPKRAVS (SEQ ID NO.:16) or portions thereof; DDHDSVDKIVIQKYHTVNGHNCEVRKALS (SEQ ID NO.:17) or portion thereof, and the like.

Examples of antisense oligonucleotides of the present invention include but are not limited to nucleic acid sequences anti complementary to the sequence or portion thereof of hn-RNPA1, A2, BE of FIGS. 1–3.

The oligonucleotides of the present invention may contain at least one or more modified linking group, sugar residue and/or base. The modified oligonucleotides of the invention, are resistant to degradation under both physiological and tissue culture conditions, and in particular are resistant to degradation by exonucleases. Such modifications include but are not limited to methyl phosphorothioate internucleotide linkages, phosphorothioate linkages, phosphoramidate internucleotide linkages, a 3' end cap and a 3' hair-pin loop structure. Such modified oligonucleotides and methods for production thereof are described in U.S. Pat. Nos. 5,264,562, 5,194,599 and 5,256,775, Padmapriya and Agrawal, *Bio Org. & Med. Chem. Lett.,* 3, 761 (1993), Temsamani et al., *Ann. N.Y. Acad. Sci.,* 660, 318 (1992), Tang et al., *Nucleic Acids Res.,* 21, 2729 (1993). Examples of such modified oligonucleotides include but are not limited to oligonucleotide methylphosphorothionates, 3' end-capped oligodeoxy nucleotide phosphorothioates and oligonucleotide phosphorothioates having a hair-pin loop structure at their 3' ends.

The oligonucleotides of the present invention may also be modified by the addition of groups to facilitate their entry into cells. Such groups include but are not limited to, non-polypeptide polymers, polypeptides, lipophilic groups and the like. Lipophilic groups refer to moieties which are chemically compatible with the outer cell surface, i.e., so as to enable the oligonucleotide to attach to, merge with and cross the cell membrane. Examples of such lipophilic groups are fatty acids and fatty alcohols, in addition to long chain hydrocarbyl groups. Such modified oligonucleotides and methods for making are disclosed in U.S. Pat. No. 5,256,775.

Cancers which may be treated using the oligonucleotides or mixtures thereof include but are not limited to melanoma, metastases, adenocarcinoma, thymoma, lymphoma, lung cancer, liver cancer, colon cancer, kidney cancer, pancreatic cancer, brain cancer and the like. Of particular interest using the oligonucleotides of the invention include cancers that are associated with overexpression of the hn-RNP gene product or expression of the altered gene product.

In the method of treatment, the administration of the oligonucleotides of the invention may be provided prophylactically or therapeutically. The oligonucleotide or mixtures thereof may be provided in a unit dose form, each dose containing a predetermined quantity of oligonucleotides calculated to produce the desired effect in association with a pharmaceutically acceptable diluent or carrier such as phosphate-buffered saline to form a pharmaceutically composition. In addition, the oligonucleotide may be formulated in solid form and redissolved or suspended prior to use. The pharmaceutical composition may optionally contain other chemotherapeutic agents, antibodies, antivirals, exogenous immunomodulators or the like.

The route of administration may be intravenous, intramuscular, subcutaneous, intradermal, intraperitoneal, intrathecal, ex vivo, and the like. Administration may also be by transmucosal or transdermal means, or the compound may be administered orally. For transmucosal or transdermal administration, penetrants appropriate to the barrier to be permeated as used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the oligonucleotides are formulated into conventional oral administration forms, such as capsules, tablets and tonics. For topical administration, the oligonucleotides of the invention are formulated into ointments, salves, gels, or creams, as is generally known in the art.

In providing a mammal with the oligonucleotide of the present invention, preferably a human, the dosage of administered oligonucleotide will vary depending upon such factors as the mammal's age, weight, height, sex, general medical condition, previous medical history, disease progression, tumor burden, and the like. The dose is administered as indicated. Other therapeutic drugs may be administered in conjunction with the oligonucleotide.

The efficacy of treatment using the oligonucleotide may be assessed by determination of alterations in the concentration or activity of the DNA, RNA or gene product of epithelial protein, peptide or variant thereof, tumor regression, or a reduction of the pathology or symptoms associated with the cancer.

In addition, to use as a therapeutic, the oligonucleotides of the invention may be used as diagnostic reagents to detect the presence or absence of the DNA, RNA or portion thereof of the epithelial protein, peptide or variant thereof to which the oligonucleotide is complementary. Of particular interest is the detection of at least one hn-RNP or portion thereof. Such diagnostic tests are conducted by binding of the oligonucleotide to its specific target molecule which is then detected by conventional means. For example, the oligonucleotide may be labeled using radioactive, fluorescent, chemiluminescent, or chromogenic labels and the like and the presence of the label detected. The presence of the target molecule may be detected in vitro or in vivo.

Another aspect of the invention is a method of overexpressing the gene encoding the epithelial protein, peptide or variant thereof by the introduction of the gene or multiple copies of the gene into a low expressing cell line such as short term culture of normal bronchial, mammary, colon cells, NIH 3T3 cells, and the like. Of particular interest are normal low expressing cell lines obtained from lung, breast, kidney, skin, bone, prostate, ovary and the like for incorporation of the gene. The introduction of the gene is accomplished by placing the gene in an expression vector such as PCRII and transfecting the vector into the low expressing cell line. Features associated with a transformed phenotype such as clonogenially, loss of contact inhibition and tumorigenicity in nude mice is evaluated. Overexpressor cell lines showing a precancer or cancer phenotype are useful in screening for therapeutic agents that down regulate expression of the epithelial protein.

The invention also provides a transgenic animal which has incorporated into its genome one or more copies of the gene encoding an epithelial protein, peptide or variant thereof which is an early marker for cancer. The general method of producing transgenic animal is described in Krimpenfort et al U.S. Pat. No. 5,175,384, Leder et al. U.S. Pat. No. 5,175,383, Wagner et al. U.S. Pat. No. 5,175,385, Evans et al. U.S. Pat. No. 4,870,009 and Berns U.S. Pat. No. 5,174,986. The incorporation of the gene results in overexpression, altered expression or expression of multiple forms or variants of the epithelial protein. The resulting transgenic animal is prone to develop cancer and may develop cancer at an accelerated rate at one or more locations of the body. This model will allow elucidation of up and downstream biology of hnRNP and epithelial proteins sharing sequence homology with at least one or more hnRNP. These experiments could provide additional confirmatory biomarkers for early detection as well as additional targets for re-regulating the transformed cells. The animal model is also useful in screening chemotherapeutic drugs for cancer treatment.

The foregoing description of the specific embodiments will so fully reveal the general nature of the invention that others can, by applying current knowledge, readily modify and/or adopt for various applications such specific embodiments without departing from the generic concept, and therefore such adaptations and modifications are intended to be comprehended within the meaning and range of the equivalents of the disclosed embodiments.

All references and patents referred to are incorporated herein by reference.

EXAMPLE 1

Materials and Methods

Electrophoresis and western blotting:

703D4 is an $IgG2b_k$ monoclonal antibody(6). The antibody was affinty purified from mouse ascites using a Protein A sepharose column and a discontinuous glycine NaCl/citrate gradient. To analyze the antigen purification, An aliquot of the starting material and of each of the purification steps described below (ion exchange, IEF, and HPLC) were assayed by either Tris-Tricine or Tris-Glycine-SDS polyacrylamide gel electrophoresis (SDS-PAGE). Aliquots were freeze-dried and reconstituted or diluted directly in either tris-glycine sample buffer containing 5% mercaptoethanol or tricine sample buffer and electrophoresed on a 10–20% Tricine or 4–20% Tris-glycine gel (NOVEX). Proteins on duplicate gels were electrophoretically transferred to PVDF membrane at 30V for 1.5–2.0 hours, stained with Coomassie brilliant blue or blocked overnight at 4° C. with 1% bovine serum albumin in phosphate buffered saline and immunoblotted using the mouse monoclonal antibody 703D4(6). The bound antibody on the western transfer PVDF membranes was detected using direct binding of radioiodinated staphylococcal Protein A. Blots were imaged on a Phosphorimager (Molecular Dynamics, CA) and on Kodak XAR and XRP film.

Preparation of cellular subfractions:

Human tumor cell lines, including the NSCLC cell lines NCI-H720 (carcinoid) and NCI-H157 (squamous ATCC CRL-5802) used for antigen purification, were grown in RPMI-1640 medium (Gibco) supplemented with 5% fetal calf serum at 37° C. and 5% $CO_2$. The cells were harvested and washed twice with iced Dulbecco's Phosphate-buffer solution (pH7.4) and resuspended in MES buffer (17 mM morpholinoethanesulfonic acid), 20 mM EDTA, 250 mM sucrose] and homogenized in a hand-held homogenizer. Trypan blue exclusion was employed to ensure greater than 90% cell lysis following homogenization. The lysates were transferred to Beckman polyallomer centrifuge tubes, and centrifuged at 150,000× g for 60 min using a Beckman XL90 ultracentrifuge and SW41 rotor. The pellet containing the membrane and nuclear fractions were retained, and the cytosolic supernatant was discarded [Krajewski, 1993, *Cancer Res.* 53:4701–4714].

The pellet fractions were resuspended in extraction buffer (0.015 M NaCl, 10 mM Tris pH7.4, 5 mM EDTA) containing 1% Tween-20. The samples were incubated on ice for one hour with frequent vortexing, and centrifuged at 16,000× g for 20 minutes. The supernatants were then diluted 3 times with DI water and adjusted to pH 6.5

Ion-exchange chromatography and liquid phase isoelectric focussing:

A Dupont Bio Series WAX (weak anion exchange) column (MacMod, Chads Ford, Pa.), equilibrated with Tris-HCl pH 6.5, was used. Detergent-solubilized proteins were pumped through the column at 2.0 mL/min, and fractions were pooled and freeze dried. 703D4 immunoreactive material bound weakly to the resin in the presence of 50 mM NaCl, and was eluted in the unbound material from this column.

Fractions positive antigen were resuspended to a final volume of 45 ml with 4M urea containing 3% CHAPS, 10% Glycerol, and 0.8% ampholines pH range 3–10 (Bio Rad, Richmond, Calif.). This protein-ampholyte cocktail was loaded to a chilled Rotofor preparative isoelectric focusing (IEF) apparatus (Bio-DAD, Richmond, Calif.) which was operated at a constant twelve watts. One hour after the maximum voltage was reached, usually 1200V, fractions were harvested by vacuum collection. Run time was approximately four hours. pH values were determined for the twenty fractions which were harvested. 703D4 antigen was concentrated in fractions with pH 8–9. The two most positive fractions from each of three IEF runs (three batches of cells) were pooled for HPLC purification.

HPLC:

All organic solvents used were HPLC grade (Burdick & Jackson, Muskegon, Wis.). The isoelectric focussing fractions positive for antigen were diluted two-fold with 18 Mohm water, acidified with 1% trifluoroacetic acid (TFA) (Pierce Chemical Co., Rockford, Ill.), and applied to a 10 mm×10 cm Poros perfusion polymeric $C_{18}$ column (PerSeptive Biosystems, Framingham, Mass.) which was equilibrated with 5% acetonitrile/0.1% TFA The protein was eluted using a twenty minute linear gradient proceeding from 5% acetonitrile/0.1% TFA to 100% acetonitrile/0.1% TFA at a flow rate of 15 ml/minute (the limit of the pumping system). Fractions of 2.5 mLs (15 secs) were collected after a 2.0 min wash. Next, the positive fractions (2.5–5.0 mLs, ca. 40% acetonitrile) were diluted five fold with water/0.1% heptafluorobutyric acid (HFBA) (Pierce Chemical Co., Rockford, Ill.) and applied to the another Poros polymeric $C_{18}$ column equilibrated with 5% methanol/0.1% heptafluorobutyric acid (HFBA) (Pierce Chemical Co., Rockford, Ill.). The protein was eluted with a twenty minute linear gradient from 5% methanol/0.1% HFBA to 100% methanol/0.1% HFBA at a flow rate of 15 ml/minute. The 703D4 antigen eluted at approximately 80% methanol.

As the last state in the purification, the positive fractions were applied to a 2.1 mm×25 cm Vydac analytical $C_4$ column (Vydac, Hesperia, Calif.) which was equilibrated with 20% acetonitrile/0.1% TFA, and the protein eluted with a linear gradient from 20% acetonitrile to 70% acetonitrile over 150 minutes (0.3%/min), at a flow rate of 0.2 ml/minute.

Digestion and protein sequencing:

Several failed attempts at obtaining N-terminal amino acid sequence information, both on SDS-PAGE blotted material and directly from the fractions at the last $C_4$ HPLC step, indicated that the N-terminus of the purified protein was blocked. Therefore a cyanogen bromide (CNBr) digestion was employed to obtain internal sequence. The purified protein, freeze-dried after the $C_4$ HPLC fractionation, was cleaved under nitrogen with 0.15 M CNBr (Fluka) in 70% formic acid at room temperature for twenty-four hours [Gross, 1974, *Biochem. Biophys. Res. Commun.* 59, 1145–50]. The resulting peptides were separated by 16% Tricine SDS-PAGE and electroblotting onto PVDF membrane. The peptides were visualized using Ponceau S and representative bands excised for Edman degradation sequence analysis on an Applied Biosystem model 477A. Amino acid sequence obtained was compared to know sequences in the SwissProt data base using PepScan (PE/SCIEX, Thornhill, Ont., Canada).

Isolation of total cellular RNA and Northern analysis:

RNA was extracted by guanidium isothiocyanate/2-mercaptoethanol and purified by ultracentrifugation as previously described [Davis et al, 1986, Preparation and analysis of RNA from eukaryotic cells. Basic methods in molecular biology, New York, Elsevier, Science Publishing Co., Inc. 129–156]. After ultracentrifugation the RNA pellet was resuspended in water, ethanol precipitated in the presence 0.3 M sodium acetate and pelleted by centrifugation. The dried pellets were redissolved in water, and 10 $\mu$g of total cellular RNA from each of tumor cell lines, normal lung and normal bronchial epithelium primary cultures were used for northern blot analysis. The RNA was resolved using a 1% agarose-formaldehyde gel with 0.2 M 3-N-morpholino-propane sulfuric acid/0.05 M sodium acetate/0.01 M EDTA as the running buffer. The RNA was then transferred to a nitrocellulose membrane, hybridized, washed and autoradiography was performed according to standard techniques.

Northern analysis was carried out using probes prepared by random priming of inserts gel-purified from restriction endonuclease digests of plasmids containing full-length cDNAs for hnRNP-A2 and -A1. Approximately $1\times10^6$ cpm/mL of probe was used for each Northern analysis.

RT-PCR and a Southern Blot analysis:

Reverse transcription was performed with 0.2 $\mu$g of DNase-treated total RNA using Superscript according to the manufacturer's protocol (Gibco). The resulting cDNA was subjected to 35 cycles of polymerase chain reaction (PCR) on a Perkin Elmer GeneAmp PCR System 9600. The primers designed for the amplification were: 5'-GAGTCCGGTICGTGTTCGTC-3' (SEQ ID NO.:11) and 5'-TGGCAGCATCAACCTCAGC-3' (SEQ ID NO.:18). These primers were selected using DNA-Star, and were chosen to span a site of alternate exon utilization (36 nt) which generates the hnRNP splice forms -A2 and -B1. (See FIG. 7*a*) The resulting amplified DNA was analyzed by electrophoresis on a 2.0% NuSieve agarose gel. Transfer to nitrocellulose filter and hybridization, wash and autoradiography were performed as previously described [Davis et al, 1986 ibid]. Southern blot analysis was carried out with a $^{32}$P-end-labelled 20 nt antisense oligonucleotide present in both hnRNP-A2 and -B1. This 22 nt antisense oligonucleotide has the following sequence: GAGAGAGAAAGGAACAGITCC (SEQ. ID NO. 19). Tables 1–3 provide the characteristics a 1164 bp, a 1145 bp and a 1178 bp cDNA product of the present invention and the primers used to produce the cDNA products.

TABLE 1

1164 bp cDNA Product

Upper Primer: 20-mer 5' GAGTCCGGTTCGTGTTCGTC 3' (SEQ. ID NO. 11)
Lower Primer: 24-mer 5' TGGGCTCTCATCCTCTCCTATTTA 3' (SEQ. ID NO. 12)

| DNA 250 pM, Salt 50 mM | Upper Primer | Lower Primer |
|---|---|---|
| Primer TM | 54.3° C. | 55.2° C. |
| Primer Overall Stability | −38.7 kc/m | −43.7 kc/m |
| Primer Location | 74 . . . 93 | 1237 . . . 1214 |
| Product Tm — Primer Tm | 24.2° C. | |
| Primers Tm Difference | 1.0° C. | |
| Optimal Annealing Temperature | 56.3° C. | |
| Product Length | 1164 bp | |
| Product Tm (% GC Method) | 78.4° C. | |
| Product GC Content | 46.6% | |
| Product Tm at 6xSSc | 100.0° C. | |

Product Melting Temperature (% GC Method)

| Salt | | | Formamide | | | |
|---|---|---|---|---|---|---|
| mM | xSSC | xSSPE | 0% | 10% | 20% | 50% |
| 1 | 0.005 | 0.006 | 50.2 | 43.7 | 37.2 | 17.7 |
| 10 | 0.051 | 0.062 | 66.8 | 60.3 | 53.8 | 34.3 |
| 50 | 0.256 | 0.312 | 78.4 | 71.9 | 65.4 | 45.9 |
| 165 | 0.846 | 1.031 | 87.1 | 80.6 | 74.1 | 54.6 |
| 330 | 1.692 | 2.062 | 92.1 | 85.6 | 79.1 | 59.6 |
| 500 | 2.564 | 3.125 | 95.0 | 88.5 | 82.0 | 62.5 |
| 1000 | 5.128 | 6.250 | 100.0 | 93.5 | 87.0 | 67.5 |
| 195 | 1.000 | 1.219 | 0.0 | % formamide = Tm 88.3° C. | | |

TABLE 2

1145 bp cDNA Product

Upper Primer: 19-mer 5' CTACAGCGCCAGGACGAGT 3' (SEQ. ID NO. 13)
Lower Primer: 20-mer 5' CCCATGGCAAATAGGAAGAA 3' (SEQ. ID NO. 14)

| DNA 250 pM, Salt 50 mM | Upper Primer | Lower Primer |
|---|---|---|
| Primer TM | 52.7° C. | 51.8° C. |
| Primer Overall Stability | −37.8 kc/m | −39.0 kc/m |
| Primer Location | 59 . . . 77 | 1203 . . . 1184 |
| Product Tm — Primer Tm | 26.8° C. | |
| Primers Tm Difference | 1.0° C. | |

TABLE 2-continued

| 1145 bp cDNA Product | |
|---|---|
| Optimal Annealing Temperature | 55.6° C. |
| Product Length | 1145 bp |
| Product Tm (% GC Method) | 78.6° C. |
| Product GC Content | 47.0% |
| Product Tm at 6xSSc | 100.2° C. |

Product Melting Temperature (% GC Method)

| Salt | | | Formamide | | | |
|---|---|---|---|---|---|---|
| mM | xSSC | xSSPE | 0% | 10% | 20% | 50% |
| 1 | 0.005 | 0.006 | 50.4 | 43.9 | 37.4 | 17.9 |
| 10 | 0.051 | 0.062 | 67.0 | 60.5 | 54.0 | 34.5 |
| 50 | 0.256 | 0.312 | 78.6 | 72.1 | 65.6 | 46.1 |
| 165 | 0.846 | 1.031 | 87.2 | 80.7 | 74.2 | 54.7 |
| 330 | 1.692 | 2.062 | 92.2 | 85.7 | 79.2 | 59.7 |
| 500 | 2.564 | 3.125 | 95.2 | 88.7 | 82.2 | 62.7 |
| 1000 | 5.128 | 6.250 | 100.2 | 93.7 | 87.2 | 67.7 |
| 195 | 1.000 | 1.219 | 0.0 | % formamide = Tm 88.4° C. | | |

TABLE 3

| 1178 bp cDNA Product | | |
|---|---|---|
| Upper Primer: 20-mer 5' GAGTCCGGTTCGTGTTCGTC 3' (SEQ. ID NO. 11) | | |
| Lower Primer: 24-mer 5' TGTTCTGTTACCTCTGGGCTCTCA 3' (SEQ. ID NO. 15) | | |
| DNA 250 pM, Salt 50 mM | Upper Primer | Lower Primer |
| Primer TM | 54.3° C. | 56.8° C. |
| Primer Overall Stability | −38.7 kc/m | −43.1 kc/m |
| Primer Location | 74 . . . 93 | 1251 . . . 1228 |
| Product Tm — Primer Tm | 24.2° C. | |
| Primers Tm Difference | 2.5° C. | |
| Optimal Annealing Temperature | 56.3° C. | |
| Product Length | 1178 bp | |
| Product Tm (% GC Method) | 78.4° C. | |
| Product GC Content | 46.6% | |
| Product Tm at 6xSSc | 100.0° C. | |

Product Melting Temperature (% GC Method)

| Salt | | | Formamide | | | |
|---|---|---|---|---|---|---|
| mM | xSSC | xSSPE | 0% | 10% | 20% | 50% |
| 1 | 0.005 | 0.006 | 50.2 | 43.7 | 37.2 | 17.7 |
| 10 | 0.051 | 0.062 | 66.8 | 60.3 | 53.8 | 34.3 |
| 50 | 0.256 | 0.312 | 78.4 | 71.9 | 65.4 | 45.9 |
| 165 | 0.846 | 1.031 | 87.0 | 80.5 | 74.0 | 54.5 |
| 330 | 1.692 | 2.062 | 92.0 | 85.5 | 79.0 | 59.5 |
| 500 | 2.564 | 3.125 | 95.0 | 88.5 | 82.0 | 62.5 |
| 1000 | 5.128 | 6.250 | 100.0 | 93.5 | 87.0 | 67.5 |
| 195 | 1.000 | 1.219 | 0.0 | % formamide = Tm 88.2° C. | | |

EXAMPLE 2

Biochemical Characterization of 703D4 Antigen

Preliminary data showed a wide range of expression of the 703D4 antigen in non-small cell lung cancer cell lines, as judged by a solid phase radiobinding assay. All results shown are for purification steps using NCI-H720 cells which grows rapidly as floating clumps of cells in culture medium containing 5% fetal bovine serum, allowing high cell density. After the methods were developed, an identical protocol was followed to purify the antigen from the original immunogen cell line, NCI-H157. 703D4 immunoreactivity at all stages of the purification was detected by SDS-PAGE followed by immunoblot analysis as preliminary attempts to scale up our previously reported immunoprecipitation technique were not successful.

Western blot analysis of crude extract under both reducing and non-reducing conditions revealed a major specific band with mobility of approximately 31 kDa (Bio-RAD) on both reduced tris-glycine and tricine gels (FIGS. 5*b* and 5*e*). Our original analysis had suggested a slightly smaller molecule (Mr approximately 31 kDa) on Novex 10.20% tricine gel under different PAGE conditions and 35 kDa on Novex 8–16% tris-glycine gels. Under all conditions only a single major immunoreactive protein was identified, although in the later stages of purification an apparent disulfide-linked homodimer appeared which could be removed by increased reduction, and at the final HPLC steps a minor band of slightly higher Mr was also seen (FIGS. 6*b*–6*c*).

Simple subcellular fractionation analysis of 703D4 antigen distribution, according to the method of Krejewski et al., [Krejewski, 1993, *Cancer Res.* 53, 4701, 4714], showed that except for a cytosolic supernatant all membrane-bound fractions including the nuclear pellet had immunoreactive protein (data not shown). This data parallels immunohistochemical characterization of 703D4 antigen expression in fixed cells, which showed binding to perinuclear and cytosolic sites. The antigen in a NCI-H720 subcellular fraction containing nuclei and membrane-bound proteins could be solubilized by gentle extraction with either non-ionic detergents such as Tween-20, NP-40 and Triton X-100 or ionic detergent such as 1% SDS.

Weak anion exchange chromatography of crude detergent-solubilized proteins at pH6.5, 7.5 and 8.5 indicated all the immunoreactivity of the crude tumor cell extract was eluted in the unbound fraction in the presence of low (50 mM) salt. When the crude antigen was subjected to preparative IEF under denaturing conditions (4.0 M urea) the immunoreactivity appeared in fractions with pH 8–9.

EXAMPLE 3

Purification of 703D4 Antigen

The protein identified by 703D4 was isolated from NCI-H720 and -H157 cells by a six-step procedure. The first steps were carried out rapidly to prevent degradation of the target molecule by a variety of protease inhibitors or reducing agents. We were not able to completely prevent loss of the molecule. To prevent degradation during the SDS-PAGE and western blot analysis of each fractionation step, the bulk of the material was stored frozen at −30° C. during the analysis. Determination of exact recoveries at each step could not be made using a western-blot analysis method, therefore the overall yield was estimated from the total protein used for purification and the final yield of purified antigen.

A typical purification commenced with 7–10 mLs packed cells, washed with phosphate buffered saline to remove serum proteins present in the cell culture medium. The initial step was subcellular fractionation to remove cytosolic proteins, and gentle detergent solubilization of the membrane-bound fraction. The detergent-solubilized fraction was then diluted to lower the salt concentration and injected onto the weak anion-exchange column. Studies with weak and strong anion and cation exchange resins demonstrated tight binding to cation and strong anion exchange matrices at acidic to neutral pH, but poor recovery of immunoreactive material. Therefore a weak anion exchange resin was used to remove a significant portion (approximately 75%) of irrelevant protein. This prevented loss of immunoreactive protein through co-precipitation at the IEF step. The unbound material was collected, freeze-dried, and redissolved in a denaturing buffer for preparative IEF. IEF concentrated the immunoreactive protein into a basic region of the pH gradient. Several batches of cells were pooled at this point for HPLC purification.

The HPLC chromatograms from the next stages of this procedure are shown in FIG. 5a. Attempts to remove the ampolytes and urea after the preparative IEF by molecular sieve chromatography or direct injection onto silica-based reversed phase HPLC matrices resulted in precipitation of the target protein and loss within the column matrix. The Poros macro-porous polymeric $C_{18}$ column rapidly and efficiently desalted the antigen from the urea/ampholyte cocktail and simultaneously separated 703D4 immunoreactivity from the bulk of the other proteins in the mixture (FIGS. 5*a,* 5*b*). Our HPLC procedures utilize mobile phases usually applied to peptide analysis and/or purification, but proved very effective for purification of this protein. The use of the chromatographically "weaker" organic modifier (methanol) with the more lipophilic ion-pairing agent (HFBA) resulted in a distinctly different mobility of the 703D4 antigen to that in the acetonitrile/TFA mobile phase, and also provided selectivity for removal of other proteins present in the sample. The use of these two solvent systems resulted in significantly greater purification of target molecule than either solvent system alone.

Analytical $C_4$ HPLC with an acetonitrile gradient containing 0.1% trifluoroacetic acid was used as the final purification step. 2.5 mL of positive fractions from the methanol/heptafluorobutyric acid polymeric $C_{18}$ column was diluted five fold with water/0/1% TFA, injected onto a Vydac $C_4$ column and eluted with a slow gradient (0.3%/min) acetonitrile in 0.1% trifluoroacetic acid. Immunoblotting analysis of $C_4$ fractions revealed two immunoreactive proteins with distinct sizes as determined by SDS-PAGE (FIGS. 6*b* and 6*c*). The lower and later eluting one is the principal immunoreactive protein, and was greater than 95% pure as determined by coomassie staining of the SDS-PAGE gel.

Overall yield of the principal immunoreactive protein from a typical purification, determined by amino acid analysis and N-terminal Edman sequence yield, was 200 pmol. This yield implies an approximately 25,000 fold purification, although as pointed out above this detection system did not allow for an accurate estimate of loss at several of the steps in the procedure.

EXAMPLE 4

Amino-terminal Sequencing of 703D4 Antigen

Figure 8:
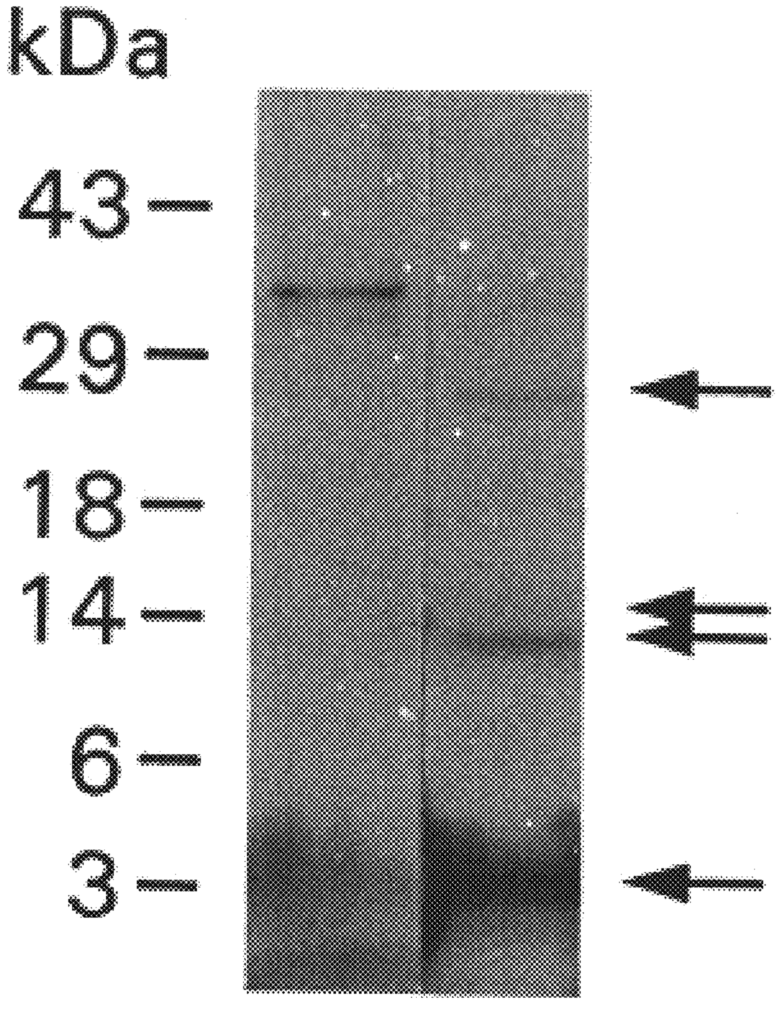
FIG. 8 shows 16% tricine SDS-PAGE analysis of products of CNBr digestion of purified 703D4 principal antigen. Note the left lane is the antigen before digestion, the arrows indicated the four visible bands which subjected to amino-terminal sequencing.

Several attempts to obtain amino-terminal sequence of purified 703D4 antigen were not successful, including direct sequencing from the C4 HPLC fractions. The major immunoreactive protein, that is, the later eluting, lower Mr band on SDS-PAGE of the analytical $C_4$ purification step, was therefore concentrated by freeze-drying the peak fractions and cleaved by CNBr/formic acid. Four bands were separated and visible after Tricine SDS-PAGE on a linear 16% gel, electroblotting onto PVDF membrane, and staining with Ponceau S or Coomassie blue (FIG. 8). All four bands were subject to 12 cycles of Edman degradation on an ABI 477A using the standard ABI protocol for blotted proteins. The sequences revealed were: AARPHSIDGRVV (SEQ ID NO.: 1) (27 kDa and 13 kDa bands), QEVQSSRSGRGG (SEQ ID NO.: 2) (15 kDa band) and EREKEQFRKLFI (SEQ ID NO.: 6) (4 kDa band). The search in SwissProt protein sequence database of each of these sequences identified a single gene product. The sequences, and the size of the cyanogen bromide digestion products, are consistent with the major 703D4 antigen being substantially homologous to the heterogeneous nuclear ribonucleoprotein (hnRNP) A2. FIG. 7*a* shows these sequences aligned with the translated cDNA sequence of hnRNP B1, which is identical to hnRNP A2 but includes a previously reported 36 nucleotide (12 amino acid) exon close to the protein amino terminus. The 4 kDa CNBr fragment sequence crossed this site of alternate exon splicing, demonstrating the major antigen is substantially homologous to hnRNP A2. As expected for CNBr-generated fragments, each sequence is immediately C-terminal to a methionine residue in the predicted sequence.

The last step in the purification of the 703D4 antigen resolved a second immunoreactive band of slightly higher molecular size, and parallel immunoreactivity (judged by a comparison of Coomasie and immunostaining intensities). A CNBr digestion was carried out on pooled $C_4$ HPLC fractions containing the minor immunoreactive band which eluted slightly before the hn RNP-A2 (pooled from three separate purifications). The CNBr digest yielded two principal Coomasie-stained bands after Tricine SDS-PAGE. The approximate 5 kDa band was Edman sequenced on an Applied Biosystems 494A and yielded a sequence EKTKEtVPlerKkrE (SEQ ID NO.:4) (amino acids in upper case represent the primary amino acid in each cycle, and lower case letters denote amino acids identified as the secondary cells). This sequence is identical to that of the hnRNP-B1 CNBr fragment which includes the 12 amino acid insertion not present in the hnRNP-A2. A lower level sequence present in the same sample was consistent with hn RNP-A2, which had not been completely resolved from hnRNP-B1 by the $C_4$HPLC (FIG. 6*a*). The 13 kDa band from the same digest yielded sequences AaRp-s-DGRvv (SEQ ID NO.:5) consistent with that expected for the 13 kDa CNBr fragment of hn RNP-A2/B1.

EXAMPLE 5

Analysis of hnRNP A2/B1 Expression

Figure 9A:
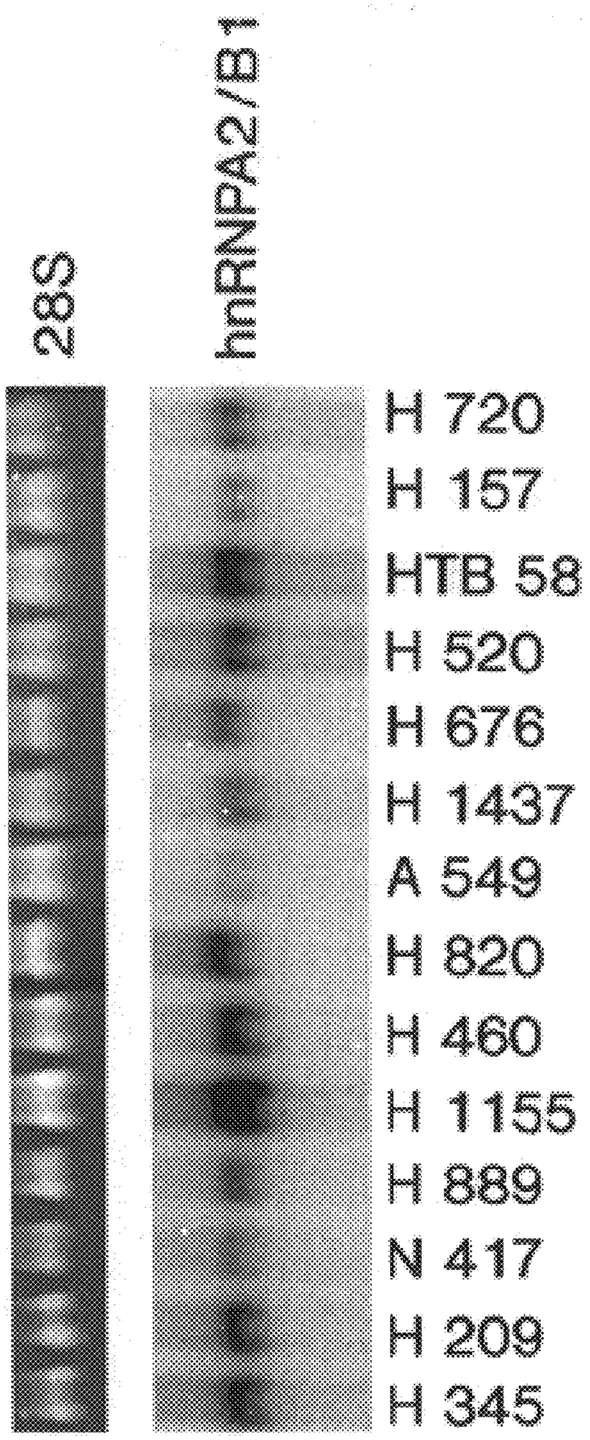
FIG. 9*a* shows expression of hnRNP-A2/B1 mRNA in lung derived cell cultures. 9*a:* Northern analysis of NSCLC cell lines (NCI-H720, H157, HTB58, H520, H676, H1437, H549, H820, H4670, H1155) and SCLC cell lines (NCI-H889, H417, H209, H345). All cells were harvested in station phase and analyzed as described in Materials and Methods. 28S rRNA band visualized under UV illumination used for quantification.
Figure 9B:
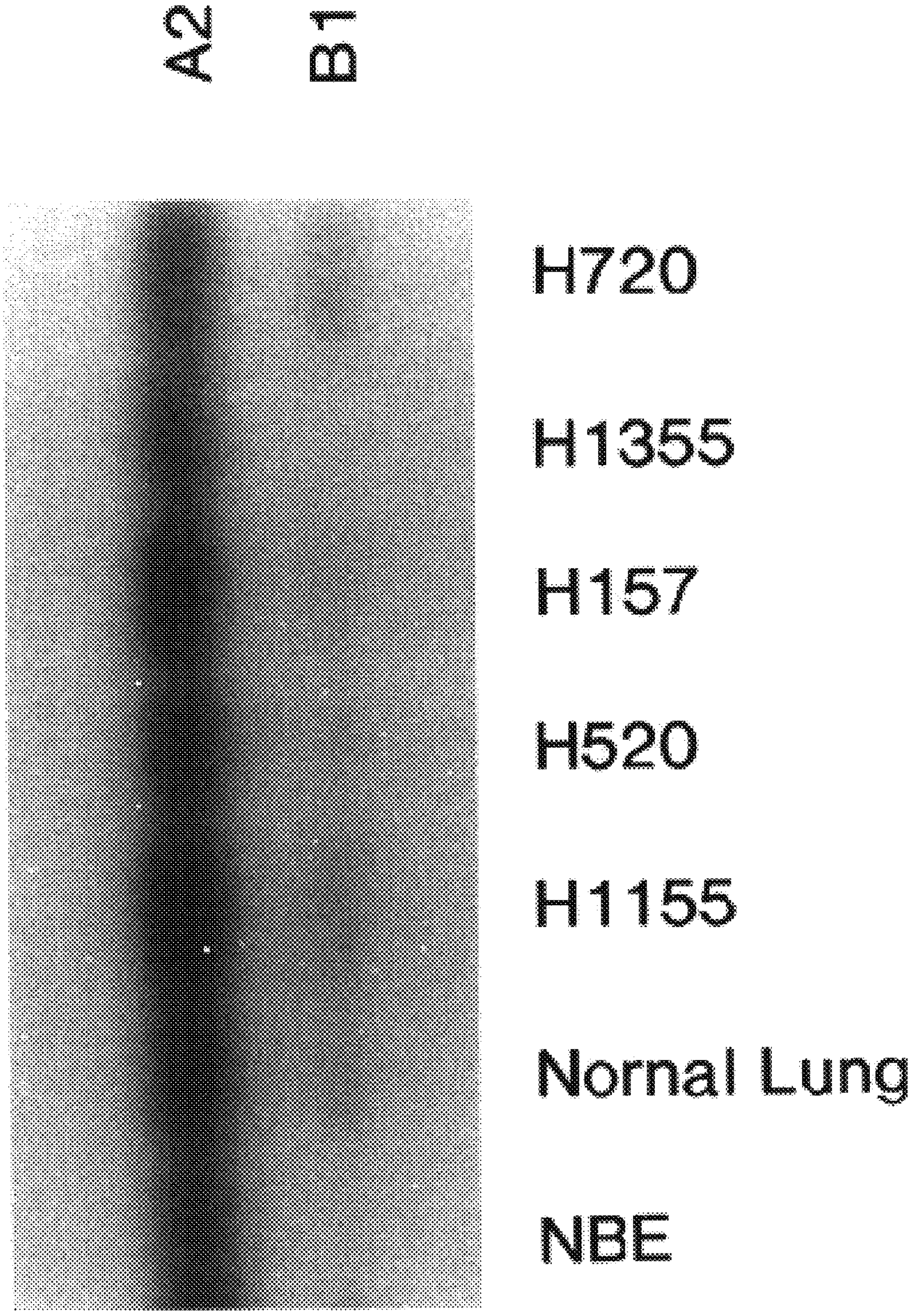
FIG. 9*b* shows RT-PCR of mRNA from cell lines NCI-H720, H1355, H1157, H1155, normal lung and normal bronchial epithelium primary culture. Expected size of the products is 280 bp (hnRNP-A2) and 316 bp (hnRNP-B1). RT-PCR was carried out as described in Materials and Methods. Products were analyzed on 2% agarose TBE-gels, transferred to nitrocellulose, and probed with an end-labelled 20% primer common to both hnRNP-A2 and -B1.

FIG. 9*a* demonstrates a wide range of expression of hnRNP A2/B1 in both normal and tumor cell lines, and is generally consistent with our radiobinding assays (results not shown).

hnRNP-A2/B1 mRNA is also expressed in the single transformed normal bronchial epithelial cell line tested, and in several normal bronchial epithelial cell primary cultures. Digitized signal intensity of the Northern blot was adjusted for loading differences by quantitation of the 28S rRNA band photographed under UV light and scanned by laser densitometry (Molecular Dynamics Personal Densitometer). Expression of hnRNP-A2/B1 in most tumor cell lines is higher than in the normal lung cell primary cultures analyzed. Both NSCLC and SCLC cell lines express hnRNP-A2/B1 mRNA. Northern analysis using a full-length cDNA probe cannot distinguish hnRNP-A2 from -B1, therefore Rt-PCR was used to confirm that both forms of the gene product are expressed. Results show that all tested cell lines and the normal lung expressed both splice forms, and that hnRNP-A2 appears to be the major form in all cases (FIG. 9*b*).

Biamonti et al have reported that expression of hnRNP-A1 mRNA, the product of a closely related but distinct gene is subject to proliferation-dependent regulation in normal fibroblasts and lymphocytes but is proliferation-independent in transformed cell lines. Expression of hnRNP-A2/B1 mRNA was analyzed at different stages of cell growth. Cells were harvested in either log phase, or stationary phase one to four days after reaching confluence. The data demonstrate that the levels of the mRNA are proliferation-dependent in all of the lung-derived cells tested (FIG. 10). In 6/6 normal bronchial epithelial cell primary cultures, 1/1 transformed bronchial epithelial cell line, and 3/3 lung tumor cell lines the levels of hnRNP-A2/B1 mRNA fall after the cells leave log-phase growth (FIG. 10).

The data demonstrates overexpression of hnRNP-A2/B1 in cancer cell lines and in transformed bronchial epithelial cells compared to short term, normal primary bronchial epithelial cell cultures (FIGS. 9*a,* 9*b* and 10). Preliminary evidence for hnRNP-A2/B1 showed overexpression in breast tumor cells and transformed breast epithelial cells compared to normal breast epithelial cell primary cultures (data not shown). These findings showed overexpression in several immortalized or transformed cell lines such as epidermal carcinoma cells, promyelocytic cells, SV40 transformed human fibroblasts and teratocarcinoma cell. Rat neuronal cell also expression a high level of hnRNP-A1 mRNA both shortly before and after birth, whereas normal primary fibroblast cultures overexpress hnRNP-Al only during the logarithmic phase of cell growth (Biamonti, G. et al, *J. Mol. Biol.,* 230, 77–89, 1993). The data demonstrates that although hnRNP-A2/B1 is overexpressed in lung epithelial tumor cells, it is still apparently subject to proliferation-dependent control. Studies on the effect of hnRNP overexpression or knockout on transformation and tumorigenicity are in progress.

Our identification of the 703D4 early lung cancer detection antigen as hnRNP-A2/B1 is provocative in light of the emerging knowledge about the hnRNP group of proteins (Burd, C. G. et al, *Science,* 29, 615–621, 1994). The family of hnRNPs have roles in RNA processing, including pre-mRNA exon splicing and splice site choice, and also in transcription, DNA replication, and recombination (Dreyfuss, et al, *Annu. Res. Biochem.,* 62, 289–321, 1993) (Spector, D. L. *Curr. Opin. Cell. Biol.,* 5, 442–447, 1993). hnRNPs are involved in shuttling mRNA from the nucleus to the cytosol, which is consistent with the subcellular fractionation described here and our previously reported immunohistochemical localization (Katz, D. et al *Nucleic Acid Res.* 22, 238–246, 1994; Pinol-Roma et al *Nature* 355, 730–732, 1992). These roles for the hnRNPs indicate these proteins are integral to cellular proliferation, although the exact mechanism by which hnRNP-A2/B1 is involved in carcinogenesis is not yet clear. Proliferation markers increase in cells responding normally to injury or during fetal growth, and so are not selective for pre-neoplastic carcinogenized cells (Risio, M. J. *J. Cell. Biochem. Suppl.* 166, 79–87, 1992; Ganju, R. K. *J. Clin. Invest.* 94, 1784–1791, 1994). However, our clinical findings of increased levels of hnRNP-A2/B1 in exfoliated bronchial cells from patients whose lungs are in the pre-malignant phases of carcinogenesis indicates a casual role for hnRNP-A2/B1 in the process of carcinogenesis. These data, from several different systems, support a role for hnRNP-A2/B1 and A1/B2 or molecule closely related to these proteins in the expression of the transformation phenotype, and thereby provide a rationale for identification of 703D4 as an early lung tumor detection antibody.

EXAMPLE 6

In Vivo Inhibition of Epithelial Protein Expression and Tumor Growth Rate in Murine Systems In one embodiment, epithelial protein expression and tumor growth rate inhibition may be demonstrated in the following manner. H-157 or H720 tumor cell line known to express high levels of the epithelial protein is injected subcutaneously into the flanks of Balb/C (strain) mice. The antisense oligonucleotide (SEQ ID NO.: 20) (5'TAAGCTTTCCCCATTGTTCGTAGT3') is administered at a concentration of 2.5 mg per Kg body weight by intravenous injection into one group of mice. Control mice are injected with a control oligonucleotide. After 30 days the lungs are removed and the expression of the epithelial protein monitored by immunoassay, or by Northern or Southern blot analysis. hnRNP expression and tumor growth rate are expected to be lower in those mice receiving injections of antisense oligonucleotides than those receiving injection of the control oligonucleotide.

EXAMPLE 7

Inhibition of Epithelial Protein Expression in Human Cells

Inhibition of epithelial protein expression in human cells may be shown as follows. NCI-H720 human lung carcinoid cancer cells are grown in R5 medium. Antisense oligonucleotide having the nucleic acid sequence 5'TAAGCTTTTC-CCCATTGTTCGTAGT3' is resuspended in phosphate buffered saline and mixed with DOTAP (Boehringer Mannheim), a lipofection reagent (2.5 $\mu$g/ml of culture medium) at the desired concentration. Fresh antisense oligonucleotide, in the absence of DOTAP, is added after 16–20 hrs of incubation. After 26–40 hours the cells are rinsed in serum-free media lacking both methionine and cysteine and label added for 4 hours in 1 ml of medium containing 150–200 $\mu Ci^{35}S$-translabel (ICN). The medium is collected.

Immunoprecipitates are recovered after incubation with 703D4 antibody electrophoresed and autoradiographed. The epithelial protein expression is expected to be lower from human cells treated with antisense oligonucleotide than human cells treated with a control oligonucleotide.

EXAMPLE 8

Expression of Early Lung Cancer Detection Marker P31 in Neoplastic and Non-Neoplastic Respiratory Epithelium

Materials and Methods

Tissues

Twenty-eight paraffin-embedded, stage I NSCLC resection specimens and corresponding pathology reports from 28 patients were obtained from the Department of Pathology, Naval Hospital, Bethesda, M.D. as part of an approved clinical protocol (22). All material was reviewed by the study's reference pathologist (R.I.L.) and tumors were diagnosed according to the WHO classification (23). For each patient, one representative tissue block was chosen and the morphologic status of the respiratory epithelium in three lung compartments (bronchi, bronchioli, alveoli) was recorded. P31 status was evaluated relative to the field changes in the airways adjacent to the primary tumor contained in the paraffin block.

Immunohistochemistry

703D4 (5) was purified from mouse ascites using a Protein A column and discontinuous glycine NaCl/citrate gradient (Pierce, Rockford, Ill.). 10 $\mu$g/ml of Protein A purified mouse monoclonal antibody was used to identify areas of p31 expression. Immunohistochemical staining was performed using the Vectastian ABC kit (Vector Laboratories, Burlingame, CA) following the vendor's instructions with previously reported modifications (11). All experiments incorporated a tumor slide known to express p31 as a positive control and an isotopic (IgG 2b) myeloma protein (Sigma Chemical Co., St. Louis, Mo.) as a negative control.

Procedure for Slide Analysis

Three distinct lung compartments (bronchi, bronchioli, and alveoli) were mapped for each case using light microscopy in corresponding hematoxylin and eosin stained sections. These compartments were differentiated by their epithelium and surrounding tissue as previously described (12). All slides were screened for the presence of the following histologic abnormalities: basal cell hyperplasia (BCH); goblet cell hyperplasia (GCH); squamous metaplasia (SQM), dysplasia (DYS); type II cell hyperplasia (T2H); fibrosis (FIB) and bronchiolization of the alveoli (BOA) (Table I). These morphologic designations were determined by concurrence of three reviewers (J.Z., S.M.I., R.I.L.) using published criteria (9,13,14).

To quantitate abnormalities in each compartment, the number of HPFs containing the abnormality was divided by the total number of fields analyzed. All individual representatives of the bronchial and/or bronchiolor compartments contained in each section was analyzed. Each slide was designated as having one alveolar region. In alveoli containing abnormalities, a total of 10 high power fields (HPFs) per slide using a 40× objective of the microscope was sampled and counted. In bronchi and bronchioli, it was not always possible to evaluate 10 HPFs of abnormalities, therefore as many HPFs as possible were included. For instance, in one bronchus 3 HPFs of BCH in a total of HPFs (Table II) were counted. For comparison between regions, the staining index (SI, see below) for areas of related histology (ARH) was averaged, that is, for each histological abnormality and for normal epithelium in each lung compartment Levels of p31 expression were scored in normal and atypical lung compartments as well as corresponding tumor tissue independently by two readers (J.Z., S.M.J.). Discrepancies were resolved after joint review prior to clinical correlation analysis. A staining distribution score (0=no positive cells; 1 for 1–10%; 2 for 11–50%; 3 for 51–100% of cell positive) and staining intensity score (0=negative, 1=+; 2=++; 3=+++) was obtained for each patient. Using the sum of these values, an SI (SI=distribution score+intensity score, possible values: 0, 2–6) was established for each lung compartment as previously published (15) (Table 4).

TABLE 4

SCORING CRITERIA FOR P31 EXPRESSION

| Staining Index[1] (0, 2–6) | Staining pattern | Cellular Localization |
|---|---|---|
| Negative = (0) | Focal = (F) | Cytoplasmic |
| Weak = (2) | Diffuse = (D) | Membranous |
| Moderate = (3–4) | | Perinuclear |
| Strong = (5–6) | | |

[1]Staining index (SI) = Sum of distribution of and intensity scores were distribution scores equals the percent of positive epithelial cells in high power field (0 = no positive cells; 1 for 1–10%; 2 for 11–50%; 3 for 51–100% of cells positive) and intensity of staining (0 = negative, 1 = +; 2 = ++; 3 = +++).

Clinicopathologic analysis

Data were obtained from 28 patients. SI data for all compartments examined were averaged to yield one value per patient per compartment. Comparisons of SIs were performed between various subgroups using Wilcoxon rank sum test. All p-values are two-sided.

EXAMPLE 9

Results

Distribution of Normal vs Abnormal Lung Compartments

From the 28 NSCLC cases examined, we identified 11 bronchi in 6 specimens, 40 bronchioli in 21 specimens, and 24 alveolar regions in 24 specimens. Twenty-seven of the 28 specimens were included in the analysis since they contained both tumor and non-neoplastic lung tissue (one specimen contained only tumor with no recognizable non-neoplastic tissue). The presence of histologic abnormalities in each lung compartment were then screened. BCH, GCH and DYS was detected in 3, 2 and 1 bronchi respectively, however no areas of SQM were detected in any of the specimens examined. In bronchioli, only 7 of 40 were found to contain histologic abnormalities. Of the 24 specimens with alveolar tissue, 7 contained histologically normal alveoli and 17 contained one or more abnormality. T2H was the most common histologic abnormality observed (15/24), while BOA was detected in only 3 of the 24 cases (2 of which also contained T2H) and one alveolar compartment contained FIB. A summary of histologic abnormalities detected in the various lung compartments are shown in Table 5.

TABLE 5

DISTRIBUTION OF HISTOLOGIC ABNORMALITIES IN NON-NEOPLASTIC LUNG (N = 27)[1]

| Compartment | Number of normal | Number of ARHs with abnormalities (Number of HPFs with abnormality/Total number of HPFs)[3] | | | | | |
|---|---|---|---|---|---|---|---|
| Number (n)[2] | (%) | BCH | GCH | SQM | DYS | T2H | BOA |
| BRONCHI (11)[4] | 6 (55%) | 3 (8/21) | 2 (20/20) | — | 1 (8/10) | — | — |
| BRONCHIOLI (40) | 33 (82%) | 1 (2/3) | — | — | 6 (24/27) | — | — |
| ALVEOLI (24)[4] | 7 (29%) | — | — | — | — | 15 (80/160) | 3 (6/160) |

Abbreviations: BCH = basal cell hyperplasia, GCH = goblet cell hyperplasia, SQM = squamous metaplasia, DYS = dysplasia, T2H — type II hyperplasia, BOA — bronchiolization of the alveoli

[1]Number of patients specimens, one of the 28 slides lacked non-neoplastic lung tissue

[2]Number of areas of related histology (ARHs) analyzed

[3]ARHs = Areas of related histology

Figure 11C:
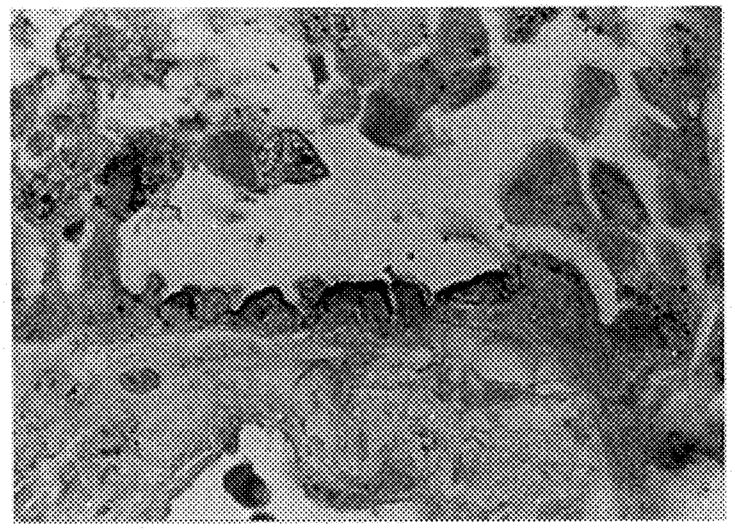

[4]Some compartments contained more than one abnormality.

p31 expression in NSCLC p31 expression in a range of NSCLC subtypes are tabulated in Table 6. Of the 28 primary lung tumors, 16 (57%) demonstrated p31 immunoreactivity. p31 expression in all histologic subtypes except the single carcinoid examined was observed. Both focal (detected in solitary cell or small groups of tumor cells) and diffuse (>50% of tumor cells positive) staining was observed. The predominant staining pattern was diffuse and cytoplasmic as illustrated in FIGS. 11*a* and 11*b*. In addition to the predominantly cytoplasmic staining pattern, membranous staining was observed in 1 of the 9 adenocarcinomas (FIG. 11*c*) and the 1 pulmonary blastoma. No correlation was apparent between staining pattern, mean staining index and tumor histology.

p31 Expression in Non-Neoplastic Lung

Figure 12A:
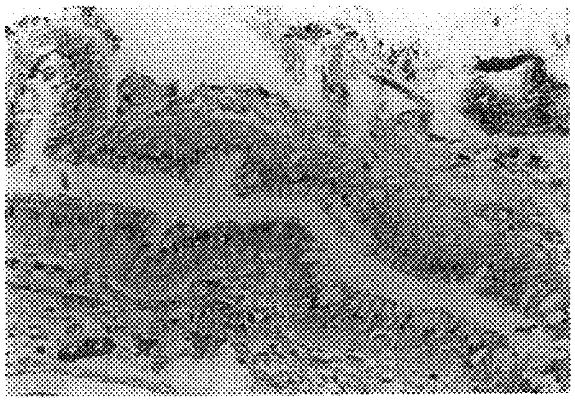
FIGS. 12A through 12D shows P31 expression pattern in non-neoplastic lung (lacking histologic abnormalities). 12A) Diffuse granular localization of p31 towards the apical portion of ciliated and non-ciliated bronchial epithelium. Note faint staining of underlying basal cells (arrows) (Immunohistochemical staining, X225). 12B) Strong p31 expression in bronchial glands (Immunoperoxidase, X225). 12C) p31 expression in bronchial (Immunohistochemical staining, X270). 12D) Localization of p31 in normal type II cells. Note moderate staining intensify and the distribution of normal type II cells along alveolar delicate (normal) septa. (Immunoperoxidase, X360).
Figure 12B:
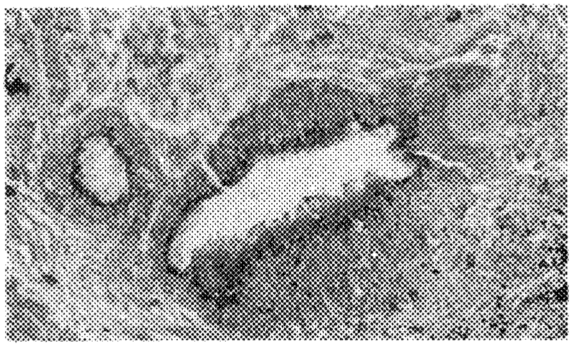
Figure 12C:
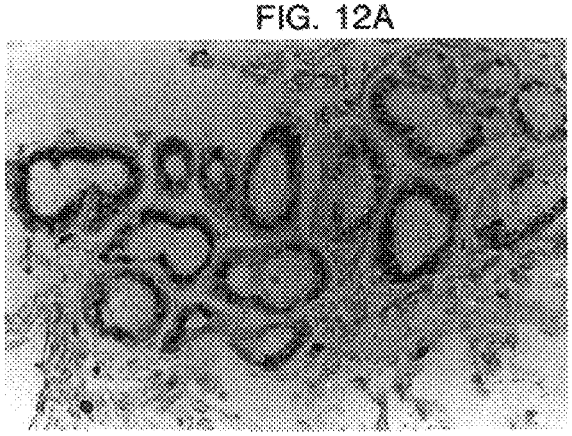

Results of p31 staining in normal and atypical lung compartments are summarized in Table 7. While p31 staining was not detected in histologically abnormal bronchi and bronchioli, patterns of diffuse and/or focal cytoplasmic p31 staining was expressed in one third of morphologically normal bronchi and bronchioli. More specifically, p31 expression was detected in both ciliated and non-ciliated epithelial cells as well as underlying basal cell epithelium (FIGS. 12*a,* 12*b*). While only 2 of 27 cases demonstrated well preserved bronchial glands, both demonstrated strong granular staining for p31 (FIG. 12*c*).

TABLE 6

P31 EXPRESSION IN NSCLC

| Histology | Total | Number of Positive tumors[1] | Mean Staining Index ± SEM | Staining pattern[2] |
|---|---|---|---|---|
| ADENO[3] | 16 | 9 | 2.4 ± 0.55 | D/C(8), D/C M P(1) |
| LARGE CELL | 3 | 3 | 3.0 ± 0.58 | D/C(2), F/C(1) |
| SQUAMOUS | 5 | 2 | 1.2 ± 0.8 | D/C(1), F/C(1) |
| MIXED | 2 | 1 | 2.0 ± 1.98 | D/C(1) |
| CARCINOID | 1 | 0 | 0.0 | — |
| OTHER[4] | 1 | 1 | 4.0 | D/C M P, F/C(1) |
| Total | 28 | 16 | 2.2 ± 0.09 | D/C(14),F/C(3),D/M(2),D/P(1) |

[1]A tumor with staining index ≧2 was called positive.
[2]Abbreviations, D = diffuse, F = focal, C = cytoplasmic, M = membranous, P = perinuclear, Some tumors demonstrated more than one staining pattern
[3]Adenocarcinoma subtypes included: Papillary and bronchioalveolar (11), Moderately differentiated (3) and Poorly differentiated (2). One of the adenocarcinomas had a small cell lung cancer compartment next to a papillary component which was negative.
[4]Pulmonary blastoma.

TABLE 7

P31 EXPRESSION IN NON-NEOPLASTIC LUNG

| Histology of Adjacent Tumor (N)[3] | Number of Positive ARH[1]/total ARH [Pattern][2] | | | | | |
|---|---|---|---|---|---|---|
| | Bronchi (n = 11)[4] | | Bronchioli (n = 40) | | Alveoli (n = 24) | |
| | Normal | Atypia[5] | Normal | Atypia[5] | Normal | Atypia[6] |
| Adeno (16) | 0/2 | 0/5 | 6/21 [D/C] | 0/7 | 1/5 [F/C] | 2/10 [D/C, D/M] |
| Large cell (3) | — | — | 0/4 | — | 0/1 | 0/1 |
| Squamous (5) | 0/2 | — | 4/5 [3F/C, 1D/C] | — | — | 2/4 [D/M, F/C] |
| Mixed (2) | 1/1 [D/C] | — | 1/2 [D/C] | — | — | 1/2 [D/C] |
| Carcinoid (1) | — | — | 0/1 | — | 0/1 | — |
| Other[7] (1) | 1/1 [F/C] | — | — | — | — | — |
| Total (%) | 2/6(33) | 0/5(0) | 11/33(33) | 0/7(0) | 1/7(4) | 5/17(29) |

Figure 12D:
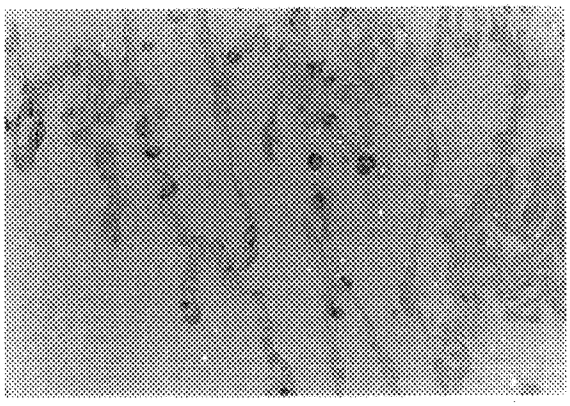
Figure 13A:
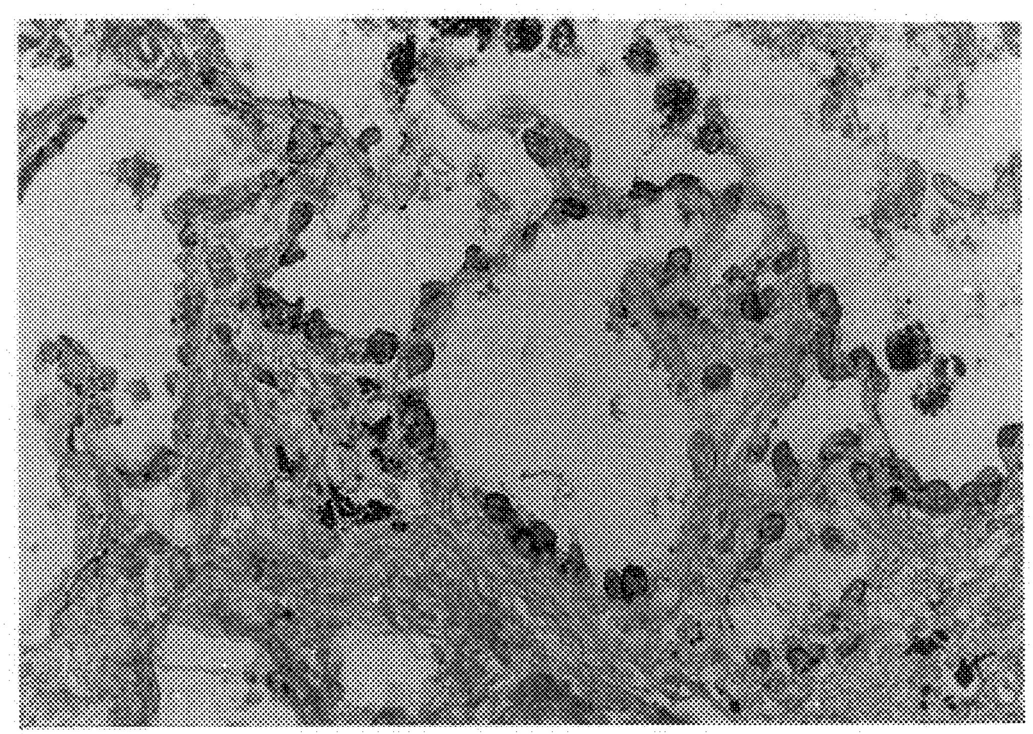
FIGS. 13A through 13B show variable localization of p31 expression in type II cell hyperplasia. 13A) Type II hyperplasia demonstrating strong diffuse cytoplasmic p31 immunoreactivity. Note increased number of type II cells and presence of fibrosis as compared with normal alveolar epithelium in FIG. 12D (Immunohistochemical of p31 in type II cell hyperplasia. (Immunohistochemical staining, X360). 13B shows membranous pattern of positive expression with Type II pneumocytes.
Figure 13B:
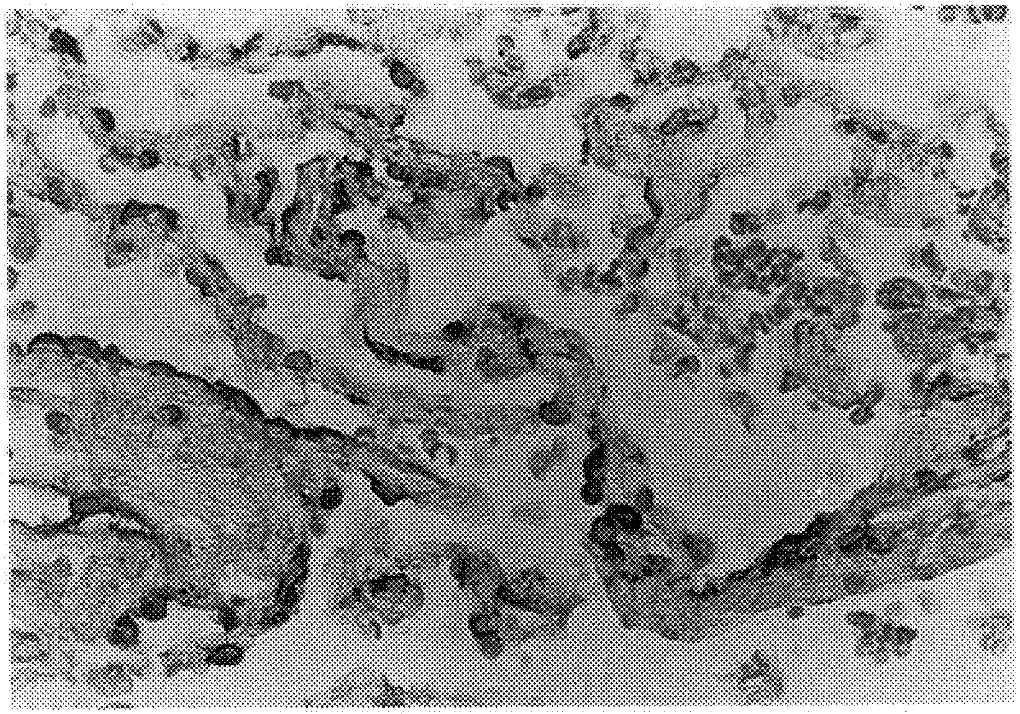

[1]All ARH with staining index ≧2 were scored positive.
[2]Abbreviations, D = diffuse, F = focal, C = cytoplasmic, M = membranous
[3](N) = number of patient specimens.
[4](n) = number of lung compartments
[5]Basal cell hyperplasia, goblet cell hyperplasia, dysplasia
[6]Fibrosis, type II hyperplasia, bronchiolization of the alveoli
[7]Pulmonary blastoma
p31 expression in alveolar epithelium was confined to type II cells (FIG. 12d) and was most remarkable in areas containing T2H (FIGS. 13a and p31 expression in alveolar epithelium was confined to type II cells (FIG. 12*d*) and was most remarkable in areas containing T2H (FIGS. 13*a* and 13*b*) which were frequently accompanied by fibrosis. In contrast, areas containing BOA were negative (not shown). Since p31 staining was most remarkable in alveoli, p31 immunoreactivity in two patient groups was compared, one with histologically normal alveolar regions (n=5) and the other with T2H (n=15). Only 1 of 5 patients demonstrated p31 staining in the group with normal alveoli, as compared to 5 of 15 patients which had positive p31 staining in regions containing T2H. A stronger staining intensity was observed in alveolar regions containing T2H (FIGS. 13*a* and 13*b*) when compared to normal alveolar regions (FIG. 12*d*). When the mean SI of normal alveolar epithelium (0.36±0.36) to T2H (1.09±0.45) was compared, no statistically significant difference (p=0.37, Wilcoxon rank sum) was found. Both diffuse and focal cytoplasmic staining were seen in alveoli, however, membranous staining was occasionally observed in alveoli containing T2H (FIG. 13*b*).

Comparison of p31 Expression in Tumor vs Non-neoplastic Lung

A comparison of p31 immunoreactivity in tumor versus surrounding non-neoplastic lung is illustrated in Table 8. Of the 27 specimens analyzed, 15 contained p31 positive tumor tissue, 7 of which (47%) also demonstrated p31 staining in the surrounding non-neoplastic lung (most frequently in alveolar region) and the remaining 8 specimens (53%) showed no antigen expression in non-neoplastic lung. Alternatively, in 3 of 12 cases where the tumor tissue did not express p31, the surrounding non-neoplastic tissue was positive for p31 expression (25%). There was no significant association between p31 expression in tumor and nonneoplastic lung (p2=0.42, Fisher's exact test).

TABLE 8

Comparison Of p31 Expression In Tumor vs. Non-neoplastic Lung

| TUMOR (27)[1] | NON-NEOPLASTIC LUNG (27) | |
|---|---|---|
| | POSITIVE | NEGATIVE |
| POSITIVE (15) | 7 | 8 |
| NEGATIVE (12) | 3 | 9 |

Clinicopathological correlation:

p31 expression in various lung compartments was evaluated for association with clinicopathologic features such as smoking history (pack years), sex and age. No correlation could be found between p31 expression and gender (Table 9).

TABLE 9

Relationship of p31 expression status and clinical features (age)

| Sex | Years Range | (N)[1] | NUMBER OF PATIENTS WITH STAINING INDEX ≧2/TOTAL NUMBER OF PATIENTS (MEAN STAINING INDEX ± SEM) Bronchi | Bronchioli | Alveolar Region | Tumor |
|---|---|---|---|---|---|---|
| Males | ≦59 | (6) | 0/2 (0) | 0/8 (0) | 0/9 (0) | 5/10 (1.90 ± 0.66) |
| | ≧60 | (11) | 1/2 (2.0 ± 2.0) | 3/5 (1.6 ± 0.68) | 2/6 (1.08 ± 0.79) | 4/7 (1.71 ± 0.68) |
| | | $p_2$ = | 0.62 | 0.023 | 0.09 | 0.92 |
| Females | ≦59 | (3) | 0/2 (0) | 0/4 (0) | 1/5 (0.4 ± 0.4) | 4/6 (3.0 ± 0.97) |
| | ≧60 | (8) | 1/1 (2.0) | 2/4 (2.3 ± 1.35) | 3/4 (2.58 ± 0.93) | 3/5 (2.4 ± 0.98) |
| | | $p_2$ = | 0.48 | 0.19 | 0.08 | 0.49 |
| Males | All ages | (17) | 1/4 (1.0 ± 1.0) | 3/13 (0.62 ± 0.33) | 2/15 (0.43 ± 0.33) | 9/17 (1.82 ± 0.46) |
| Females | All ages | (11) | 1/2 (0.67 ± 0.67) | 2/8 (1.15 ± 0.76) | 4/9 (1.37 ± 0.58) | 8/11 (2.73 ± 0.66) |
| | | $p_2$ = | 0.83 | 0.73 | 0.11 | 0.21 |

[1](N) = Number of patients.

There was a statistically significant association of p31 expression status with smoking history and age. A significant increase in p31 expression was observed in heavy smokers (>50 pack years) in bronchioli ($P_2$=0.021). A statistically significant increase in p31 expression in bronchioli ($P_2$=0.005) and alveoli ($P_2$=0.017) of older patients (Table 10) was found. This increase in p31 expression with smoking history and age only reached significance (p<0.05) when males and females were grouped together, but appears as a nonsignificant increase (trend) for each sex separately.

TABLE 10

Relationship of p31 expression status with smoking history & age

| Clinical Features | Total Number of Cases | Mean Staining Index[1] ± SEM (Number of Specimens) Bronchi | | Bronchioli | | Alveolar Region | | Tumor | |
|---|---|---|---|---|---|---|---|---|---|
| Pack Years | | | | | | | | | |
| ≦50 | 14 | 0.4 ± 0.4 | (5) | 0 | (10) | 0.2 ± 0.2 | (10) | 2.71 ± 0.52 | (14) |
| >50 | 14 | 2.0 ± 2.0 | (2) | 1.56 ± 0.59 | (11) | 1.2 ± 0.48 | (14) | 1.64 ± 0.55 | (14) |
| | $p_2$ = | 0.47 | | 0.021 | | 0.14 | | 0.2 | |

TABLE 10-continued

Relationship of p31 expression status with smoking history & age

| Clinical Features | Total Number of Cases | Mean Staining Index[1] ± SEM (Number of Specimens) Bronchi | | Bronchioli | | Alveolar Region | | Tumor | |
|---|---|---|---|---|---|---|---|---|---|
| Age | | | | | | | | | |
| ≦59 | 16 | 0 | (4) | 0 | (12) | 0.14 ± 0.14 | (14) | 2.31 ± 0.55 | (16) |
| ≧60 | 12 | 2.0 ± 1.15 | (3) | 1.9 ± 0.67 | (9) | 1.68 ± 0.62 | (10) | 2.0 ± 0.55 | (12) |
| | $p_2$ = | 0.12 | | 0.005 | | 0.017 | | 0.65 | |

[1]Mean staining index was calculated to yield one value per patient per subcompartment.

The studies have shown the presence of p31 immunoreactivity in all major histologic subtypes of tumors. p31 expression was also found in all three compartments (bronchi, bronchioli, alveoli) of respiratory epithelium. The findings demonstrated that the p31 expression pattern in NSCLC and nonneoplastic lung was variable. Both diffuse and focal staining mostly in the cytoplasm and occasionally on the cell membrane was observed. In this analysis p31 immunoreactivity was found more frequently in patients over 55 years and individuals with prolonged smoking history.

To determine if p31 expression identifies potentially important preneoplastic cell populations, we focused on p31 immunoreactivity in non-neoplastic lung was focused on. p31 was most commonly expressed in areas of T2H, which may reflect changes in the biology of this common cell type suggesting that T2H is a candidate preneoplastic change. This may be particularly relevant because the histopathology of lung cancer has been changing recently, with adenocarcinoma increasing in the United States. Pulmonary adenocarcinomas commonly demonstrating papillolepidic features are thought to arise from progenitor cells in the peripheral airways, namely the Clara cells and type II pneumocytes. Yet, preneoplastic histologic abnormalities found in the peripheral airways (bronchioli and/or alveoli) are not well defined. The fact that normal appearing type II cells can express the p31 early lung cancer detection marker may be indicative of the initial transformation to a precancer state.

In contrast, well-defined histologic abnormalities such as BCH, GCH, SQM are frequently seen in conducting airways (bronchi and bronchioli); however, all of these histologic changes are potentially reversible (14). SQM was not detected in any of the specimens analyzed in this study. This was most likely due to the limited amount of material available for study. The absence of SQM and lack of p31 staining in histological abnormalities of airways in general may reflect the reversible nature of these lesions. We have previously shown that p31 expression is absent in human lung tissue obtained from young, non-smoking trauma victims. Therefore, the presence of p31 immunoreactivity in histologically normal epithelium may actually indicate an early event preceding cytomorphological change in conducting airways.

According to the stem cell hypothesis, a single cell can differentiate along three paths to give rise to normal lung as well as the major histologic types of lung cancer (24). Since p31 can be detected in all major types of lung cancer the expression of p31 may be an early event in lung carcinogenesis. As reported in Table V there were 3 specimens which did not express p31 but p31 was still expressed in the surrounding non neoplastic epithelium.

p31 expression occurs throughout the human lung in both non-neoplastic and neoplastic tissue from patients who had Stage I NSCLC resections with curative intent. The distinct expression pattern makes p31 an informative marker for potentially neoplastic events such as peripheral adenocarcinomas originating in the alveolar region of human lung. Increased p31 expression was found to be associated with T2H, increased age and prolonged smoking history.

EXAMPLE 10 hnRNP Prospective Detection of Preclinical Lung Cancer

Two prospective studies on preclinical detection of early lung cancer that compare the accuracy of hnRNP overexpression by exfoliated sputum epithelial cells with routine sputum morphology were conducted. These studies were initiated to address the questions: (a) Does hnRNP prospectively detect lung cancer in the absence of dysplastic changes in epithelial cells, and (b) can hnRNP overexpression be detected prospectively in high-risk persons with no prior lung cancer? The first question is addressed by an eleven-center study, "The early detection of second primary lung cancers (SPLCs) by sputum immunostaining," conducted by the Lung Cancer Early Detection Working Group (LCEDWG)[21] in patients whose annual incidence of SPLC is between 1 percent and 5 percent.[25]

In a second study, hnRNP expression was evaluated in Yunnan Tin Corp (YTC) miners, a community-dwelling Chinese population of tobacco smokers, industrially exposed to radon and arsenic, whose average annual incidence of primary lung cancer (1° LC) is 1 percent.[26] These studies entail prospective observational designs, not comparative treatment trials. Initial screening and first-year follow-up data are presented separately for each study. Consistent with findings observed previously in archived material, we observed that 67 percent of those identified in advance by up-regulation of hnRNP in their premalignant sputum specimens developed lung cancer.

SPLC Population and Study Design

Investigators at institutions formerly participating in the National Cancer Institute's Lung Cancer Study Group (LCSG),[27-30] plus other institutions with active surgical oncology programs, have formed the collaborative LCEDWG. Study patients were identified by these investigators after complete resection of non-small cell lung cancer (NSCLC). Patients were not excluded on the basis of age, gender, ethic background, Karnofsky score or smoking status. TNM staging as based on the extent of the cancer at screening[31] and cell type was assigned according to WHO diagnostic criteria.[32] Provided a patient underwent biopsy of at least one mediastinal node, and all biopsied mediastinal nodes were negative, anyone with T1N0 or T2N0 disease who had not developed either recurrence or SPLC six weeks or more after surgical resection was eligible. If node sampling was not done, for a patient to be included, two years must have elapsed since surgery with no known or suspected metastases beyond the mediastinum. Following the LCSG criteria, SPLC was defined as lung cancer that, if it appeared less than 2 years after primary resection, had to be a different histological cell type, and if it appeared more than 2 years after resection, could be of the same cell type, provided that it had the characteristics of a primary cancer and arose in a different lobe.[25]

Before enrolling patients, each LCEDWG institution received local Human Volunteers Committee approval, established its sputum induction facility, and received specimen collection training and approval during a site visit by a cytotechnologies from the Johns Hopkins University School of Hygiene. Techniques for specimen production and handling were as follows: To help ensure an adequate specimen, each patient annually performed a 15-minute hypertonic saline induction. Fresh sputum was smeared on glass slides for Papanicolaou staining, and the remaining sputum was homogenized, concentrated and placed a Saccomanno's preservative (2 percent polyethylene glycol 1450 in 50 percent ethanol).[2] Over the following 3 days, the patient on arising collected post induction sputum in Saccomanno's preservative, then mailed in the pooled specimen. If routine cytologic examination at the receiving institution showed the presence of neoplastic cells, the patient underwent conventional evaluation for SPLC (or recurrence) by the treating physician. All screening specimens were sent to Johns Hopkins for analysis.

Chinese Population and Study Design

Active and retired Chinese tin miners could volunteer for annual 1° LC screening if they were older than 40, had worked underground for more than 10 years, had no previous malignancy (except nonmelanoma skin cancer), and gave informed consent. At registration, standardized interviews recorded age, gender, ethnic background, and smoking, occupational, and nutritional histories. Each annual sputum specimen produced during a hypertonic saline inducted was examined, and each miner underwent annual chest radiography. The miners in whom lung cancer was detected were advised to undergo a diagnostic work-up at the YTC Workers' General Hospital in Geiju City. The criteria used for cell type and staging were similar to those described earlier for the SPLC. Using a prospective case-cohort study design, a randomly selected subcohort of controls, age-stratified by the expected distribution of lung cancer cases, was identified at enrollment. At the conclusion of the first year of follow-up, screening sputum specimens of miners who developed 1° LC and specimens of the age-matched subcohort were sent to Johns Hopkins for analysis. imaged on a Zeiss Axiomat microscope (Carl Zeiss, Oberkochen, Germany). To optimize the transmitted light for the brown diaminobenzidine that labels hnRNP expression and the blue (hematoxylin) counterstain, Omega narrow-band filters of 600 nm (range 590 to 610 nm) and 510 nm (range 500 to 520 nm), respectively, were used.[34] Transmission was detected by a high resolution video camera (Hamamatsu Photonic Systems, Japan) interfaced to a digital image processor (Metamorph v. 2.0, Universal Imaging, West Chester, Pa.). Background-subtracted, shading-corrected images of each field at both wavelengths were then recorded to an optical drive (Panasonic/Matsushita Co., Osaka). Interpretations of Papanicolaou stained and immunostained slides and optical/electronic quantitation were entered into the data base maintained by the Johns Hopkins Oncology Biostatistics Coordinating Center. Finally, all slides and an aliquot of each specimen were placed in storage.

Statistical considerations

The primary statistical endpoint for this study was the occurrence of cancer: a second primary lung cancer (recurrences were not counted) in the SPLC population, and a primary lung cancer in the YTC population. Student's T and chi squared tests were used to assess the significance of differences between those with and without cancer, and multiple logistic regression was used to determine the simultaneous association of multiple factors. These significance levels may, of course, change by the end of these studies, but since this simply a report of consistent findings among parallel study designs, no alteration is required in the sample sizes or type I error calculations.

JHLP samples were used to develop a dual-wavelength densitometry algorithm and a linear discriminant function.[35] A refined version of this algorithm was blindly applied to the test specimens from the SPLC and 1° LC studies. Optical density measurements of epithelial cells were averaged at each wavelength and used to classify specimens as neoplastic on the basis of a linear discriminant function (SPSS-Win v 6.0, SPSS Inc., Chicago, Ill.):

$$D=\beta_0+\beta_1(\text{Optical Density}_{600})^{1/2}-\beta_2(\text{Optical Density}_{510})^{1/2}$$

The cutpoint value of D (indicating neoplasia and the weights $\beta_0$, $\beta_1$, and $\beta_2$ were determined in advance from reference sputum specimens of JHLP participants who developed squamous cell, adenocarcinoma, or small cell lung cancer, or no lung cancer at all.[4] The sensitivity and specificity of the prospective discriminant score classification among test specimens and their exact 95 percent binomial confidence limits were then calculated.

Results

SPLC Detection

Accrual of patients with resected stage I NSCLC was begun in January 1992 with a three-year goal of 1,000 patients. After 41 months, 660 patients (638 eligible, ⅔ of the goal) have been registered. The 595 patients with satisfactory specimens on first examination were primarily white and nearly 60 percent were men (Table 11). Although 90 percent of the patients had smoked in the past, three-fourths of them considered themselves former smokers at registration. Their mean age at enrollment, 3.6 years after primary resection, was 66.5 years. Good health was reflected by their average Karnofsky score (95.2). The most commonly resected cell type for the primary tumor was adenocarcinoma (43.8 percent); and when combined with the bronchoalveolar subtype (11.5 percent), adenocarcinoma constituted 55.3 percent of the resected primary tumors.

TABLE 11

Entry Characteristics of 595 Subjects at Risk of Second Primary Lung Cancer by Outcome Group

| | ACTIVE FOLLOW-UP | | | | | COMPLETED FOLLOW-UP | | | | | |
|---|---|---|---|---|---|---|---|---|---|---|---|
| | (N = 539) | | 2ND PRIMARY (N = 13) | | | RECURRENCE (N = 16) | | | NONCANCER (N = 27) | | |
| CHARACTERISTIC | N/MEAN | %/RANGE | N/MEAN | %/RANGE | p* | N/MEAN | %/RANGE | p | N/MEAN | %/RANGE | p |
| Race[†] | | | | | 0.232 | | | 0.185 | | | 0.412 |
| White | 472 | 90.1 | 13 | 100.0 | | 16 | 100.0 | | 23 | 85.2 | |
| Nonwhite | 52 | 9.9 | 0 | 0.0 | | 0 | 0.0 | | 4 | 14.8 | |
| Gender[‡] | | | | | 0.059 | | | 0.237 | | | 0.758 |
| Male | 308 | 58.6 | 11 | 84.6 | | 7 | 43.8 | | 15 | 55.6 | |
| Female | 218 | 41.4 | 2 | 15.4 | | 9 | 56.2 | | 12 | 44.4 | |
| Age at enrollment (Yrs)[‡] | 66.0 | 33–89 | 68.4 | 61–79 | 0.142 | 63.3 | 53–79 | 0.234 | 68.3 | 40–83 | 0.227 |
| Smoking Status[‡] | | | | | 0.149 | | | 0.909 | | | 0.135 |
| Current | 74 | 14.1 | 4 | 30.7 | | 2 | 13.3 | | 6 | 22.2 | |
| Former | 400 | 76.0 | 9 | 69.2 | | 12 | 80.0 | | 16 | 59.3 | |
| Never | 52 | 9.9 | 0 | 0.0 | | 1 | 6.7 | | 5 | 18.5 | |
| Age at Diagnosis (Yrs) | 62.3 | 32–85 | 65.4 | 53–79 | 0.260 | 60.7 | 53–71 | 0.489 | 64.9 | 39–79 | 0.189 |
| Karnofsky Score | 95.4 | 50–100 | 92.3 | 70–100 | 0.222 | 97.5 | 60–100 | 0.363 | 94.8 | 60–100 | 0.739 |
| Cell Type of Primary[§] | | | | | 0.108 | | | 0.530 | | | 0.913 |
| Squamous | 176 | 33.7 | 3 | 23.1 | | 4 | 25.0 | | 8 | 29.6 | |
| Large Cell | 36 | 6.9 | 2 | 15.4 | | 0 | 0.0 | | 3 | 11.1 | |
| Adenocarcinoma | 226 | 43.3 | 5 | 38.5 | | 10 | 62.5 | | 11 | 40.7 | |
| Broncho-alveolar | 62 | 11.9 | 1 | 7.7 | | 1 | 6.3 | | 4 | 14.8 | |
| Mixed | 14 | 2.7 | 2 | 15.3 | | 1 | 6.3 | | 1 | 3.7 | |
| Other | 8 | 1.5 | 0 | 0.0 | | 0 | 0.0 | | 0 | 0.0 | |
| Cell Type of 2nd Primary | | | | | | | | | | | |
| Squamous | | | 2 | 15.4 | | | | | | | |
| Large Cell | | | 2 | 15.4 | | | | | | | |
| Adenocarcinoma | | | 4 | 30.8 | | | | | | | |
| Mixed | | | 2 | 15.4 | | | | | | | |
| Other | | | 2 | 15.4 | | | | | | | |
| Missing | | | 1 | 7.7 | | | | | | | |

*p values test differences between subgroups with completed follow-up and those in active follow-up.
[‡]There are 13 cases whose gender, age at enrollment or smoking status was unknown.
[†]There are 15 cases whose race was unknown.
[§]There are 17 cases whose primary cell type was unknown.

Cytologic review of 582 of 595 (98 percent) available initial sputum specimens showed that 68.3 percent contained only normal morphology, 13.8 percent showed slight atypical (regular) metaplasia, 1.1 percent exhibited moderate atypical metaplasia, and one case (0.1 percent) showed grave atypical metaplasia. None of the specimens showed neoplastic morphology and there was no significant association between the extent of cytologic abnormality and the cell type of the primary tumor.

We recognized 13 SPLCs and 16 recurrent lung cancers consistent with the 13 of each expected during the first year on the basis of 435 person-years of follow-up. Another 27 patients have died from other causes or withdrawn from the study, for an overall total of 56 for whom follow-up has been completed. Adenocarcinoma was the most common SPLC (4 of 13, or 31 percent). Squamous cell, mixed adenosquamous, large cell, and small cell each accounted for 2 of 13 patients (15 percent), while one SPLC died before histologic confirmation (Table 11). Compared with those who did not have cancer, persons who later developed SPLC overexpressed hnRNP, as indicated by a significantly greater optical density at 600 nm (Table 12). Specimens from those whose lung cancer recurred had an intermediate optical density.

TABLE 12

Distribution of Optical Densities at 600 nm by Study, Race, Gender, Age Group, Smoking, and Endpoint Status.

| | OPTICAL DENSITY AT 600 λ | | |
|---|---|---|---|
| | MEAN ± SD | RANGE | P |
| CHARACTERISTICS OF 595 SUBJECTS AT RISK FOR 2ND PRIMARY LUNG CANCER | | | |
| Race | | | 0.2314 |
| White | 0.373 ± 0.100 | 0.048–0.756 | |
| Nonwhite | 0.356 ± 0.088 | 0.175–0.581 | |
| Gender | | | 0.2694 |
| Male | 0.375 ± 0.100 | 0.129–0.756 | |
| Female | 0.366 ± 0.097 | 0.048–0.668 | |
| Age at Enrollment | | | 0.5459 |
| ≦60 | 0.380 ± 0.110 | 0.048–0.756 | |
| 61–65 | 0.368 ± 0.093 | 0.154–0.696 | |

TABLE 12-continued

Distribution of Optical Densities at 600 nm by Study, Race, Gender, Age Group, Smoking, and Endpoint Status.

| | OPTICAL DENSITY AT 600 λ | | |
|---|---|---|---|
| | MEAN ± SD | RANGE | P |
| 66–70 | 0.369 ± 0.100 | 0.129–0.630 | |
| >70 | 0.367 ± 0.091 | 0.101–0.659 | |
| Smoking Status | | | 0.0001 |
| Current | 0.409 ± 0.111 | 0.129–0.756 | |
| Former | 0.370 ± 0.096 | 0.101–0.696 | |
| Never | 0.330 ± 0.085 | 0.048–0.513 | |
| Endpoint Status | | | 0.0177 |
| 2nd Primary Lung Cancer | 0.445 ± 0.084* | 0.332–0.622 | |
| Recurrent Lung Cancer | 0.410 ± 0.090 | 0.275–0.518 | |
| Noncancer | 0.372 ± 0.078 | 0.248–0.600 | |
| Nonendpoint | 0.369 ± 0.100 | 0.048–0.756 | |
| CHARACTERISTICS OF 94 SUBJECTS AT RISK FOR PRIMARY LUNG CANCER† | | | |
| Age at Enrollment | | | 0.5286 |
| ≦60 | 0.403 ± 0.200 | 0.128–0.854 | |
| 61–65 | 0.407 ± 0.185 | 0.142–0.848 | |
| 66–70 | 0.486 ± 0.192 | 0.175–0.880 | |
| >70 | 0.426 ± 0.231 | 0.119–0.796 | |
| Smoking Status | | | 0.8475 |
| Current | 0.428 ± 0.202 | 0.119–0.880 | |
| Former | 0.421 ± 0.189 | 0.142–0.843 | |
| Never | 0.381 ± 0.234 | 0.128–0.792 | |
| Endpoint Status | | | 0.0001 |
| Case | 0.543 ± 0.180 | 0.160–0.880 | |
| Control | 0.312 ± 0.145 | 0.119–0.796 | |

*Subjects with second primary lung cancer have a significantly greater optical density than either noncancer subjects ($p < 0.05$) or nonendpoint subjects ($p < 0.05$).
†All 94 primary lung cancer subjects are Chinese males
Note: In biological tissues, optical densities cover a theoretical range from 0.0 (clear) to 1.2 (unable to transmit light). For these samples, optical density can be roughly considered to be the proportion of background light blocked by hnRNP immunostaining.

Central Labs/Lab Procedures

Sputum Morphology: The specimen collection, preparation, staining, and quantitation methods used were described during previous evaluations of Johns Hopkins Lung Project (JHLP) archived specimens[4] and were similar for both studies. A single cytopathologist (YSE) reviewed all slides that showed even moderate atypical metaplasia, as well as a sample of the negatives.

Immunocytochemistry and Cell Culture Controls: A single lot of monoclonal antibody of hnRNP (designated 703D4) was purified from mouse ascites using a Protein A column and discontinuous glycine NaCl/citrate gradient (Pierce, Rockford, Ill.).[5] This purified antibody (10 μg/ml) was applied to cytospin slides (Shandon, Pittsburgh, Pa.) of each patient's specimen and positive control slides. For negative controls, the primary antibody was replaced by a similar protein concentration of mouse $IgG_{2b}$ nonimmune serum. Immunostaining consistency was achieved by applying Vectastain Elite ABC kit reagents (Vector Laboratories, Burlingame, Calif.) with a semiautomated capillary-gap technique (Biotek Instruments, Chicago, Ill.) following Gupta's method.[33] Slides were interpreted by a study immunocytopathologist (PKG or WHZ, FIGS. 2*a* and 2*b*) before automated measurement. Images of sputum epithelial cells showing mild atypical metaplasia and expressing hnRNP as detected by monoclonal antibody 703D4 and stained with diaminobenzidine and hematoxylin demonstrates hnRNP overexpression in an epithelial cell from a sputum specimen preceding a SPLC. ATCC human bronchogenic cancer cell lines HTB58 (squamous cell cancer) and Calu-3 (adenocarcinoma) were mixed with normal sputum, preserved in Saccomannos and used as controls.

Image Cytometry

Sputum epithelial cells with regular metaplasia were visually selected by a cytotechnologist who had no knowledge of the patients' clinical status. After 2 slides per patient were scanned, 5 to 10 characteristic fields were selected for each subject. Koehler illumination, followed by neutral density filter standardization of light transmission was established. Immunostained slides were Overall, the risk of developing SPLC during the first year was 13 out of 595 (2.2 percent, see Table 13). Of the patients who overexpressed hnRNP, ten of 15 (67 percent positive predictive value) developed SPLC 10 to 12 months after their initial examination. Only 3 of the 25 predicted to be negative (12 percent) developed SPLC (Relative Risk 5.6, sensitivity 77 percent, specificity 82 percent) for an overall accuracy of 80 percent. Evaluation of the sputum of the 13 SPLCs for morphological criteria detected only 1 patient with preclinical evidence suggesting neoplasia (grave atypical metaplasia, sensitivity 8 percent). These data indicate that immunostaining for hnRNP A2/B1 overexpression increased the sensitivity of routine sputum cell morphology in detecting SPLC nine-fold (from 8 percent to 77 percent).

TABLE 13

Immunodetection of Preclinical Second Primary Lung Cancer by hnRNP Overexpression.

| PREDICTED GROUP (TEST RESULT) | | ACTUAL GROUP CANCER | NO CANCER |
|---|---|---|---|
| Cancer (Positive) | n = 15 | 10 (76.9) | 5 (18.5) |
| No Cancer (Negative) | n = 25 | 3 (23.1) | 22 (81.5) |
| Total | n = 40 | 13 | 27 |

Overall 2nd Primary Lung Cancer risk: 13/595, 2.2%
Positive Predictive Value: 10/15, 67%
Risk among Predicted Negative: 3/25, 12%
Relative Risk of a Positive Test: 250/45, 5.6
Sensitivity: 77% Exact 95% binomial confidence interval 46% to 95%.
Specificity: 82% Exact 95% binomial confidence interval 62% to 94%.

1° LC Detection

All of the 6,285 eligible YTC miners enrolled for screening were Chinese males. Overall, the risk of developing 1° LC during the first year was 57 of 6285 (0.9 percent). All 1° LC patients were confined with a consensus "best information" diagnosis by a panel of clinicians from YTC and Johns Hopkins. The cell type of the most commonly resected primary tumors was squamous cell carcinoma (48.9 percent), while adenocarcinoma constituted 4.2 percent of the primary tumors, and large cell and small cell cancers accounted for one case each (2.1 percent). The remaining 1° LC patients with no histologic diagnosis chose traditional care. Patients without 1° LC at screening continued to be followed and were known to be free of cancer for up to two years.

Investigators at Johns Hopkins who were blinded to case/noncase status evaluated the sputum specimens for the 57 1° LC patients and 76 nonpatients. Specimens were considered satisfactory for 94 miners with a mean age at enrollment of 63 years (45 patients and 49 age-matched controls, Table 14). Although more than 90 percent had smoked in the past, only two-thirds smoked when they entered the study.

TABLE 14

Entry Characteristics of 94 Subjects at Risk of Primary Lung Cancer by Outcome Group

| | CANCER (N = 45) | | CONTROL) (N = 49) | | |
|---|---|---|---|---|---|
| CHARACTERISTIC* | N/ MEAN | %/ RANGE | N/ MEAN | %/ RANGE | P |
| Age at Enrollment (Yrs) | 62.89 | 52–74 | 62.69 | 52–75 | 0.878 |
| Smoking Status | | | | | 0.342 |
| Current | 28 | 62.22 | 33 | 67.35 | |
| Former | 15 | 33.33 | 11 | 22.45 | |
| Never | 2 | 4.44 | 5 | 10.20 | |
| Age at Outcome (Yrs) | 62.13 | 49–74 | ..† | — | |
| Time from Sputum to Outcome (Mos) | 15.38 | 3.2–36.3 | ..† | — | |
| Screening Cytology | | | | | 0.006 |
| Normal | 23 | 51.11 | 40 | 81.63 | |
| Slight | 5 | 11.11 | 5 | 10.20 | |
| Moderate | 4 | 8.89 | 4 | 8.17 | |
| Cancer | 10 | 22.22 | 0 | 0.00 | |
| Cell Type of Primary | | | | | — |
| Squamous | 23 | 51.11 | ..† | — | |
| Adenocarcinoma | 2 | 4.44 | ..† | — | |
| Large cell | 1 | 2.22 | ..† | — | |
| Other | 1 | 2.22 | ..† | — | |
| Missing | 18 | 40.00 | ..† | — | |

*Race for all subjects was Chinese, and all were males.
†Does not apply.

Compared with controls, patients who developed lung cancer during this study showed hnRNP overexpression as evidenced by significantly greater optical densities of sputum epithelial cells (Table 12). Of the 54 predicted positive by overexpression of hnRNP (Table 15), 37 (69 percent) developed lung cancer, while of the 40 predicted negative, only 8 (20 percent) for an overall accuracy of 73 percent. Similar proportions of patients who developed 1° LC and controls expressed moderate atypia in their sputum (4 of 45 and 4 of 49, respectively, or 9 percent and 8 percent). Ten of 45 (22 percent) of the cancer patients showed neoplastic cells in their sputum, while none of the controls did. These data indicate that hnRNP overexpression increased by roughly three-fold (from 22 percent to 72 percent) the sensitivity of routine (Papanicolaou-stained) sputum cell morphology to detect 1° LC.

TABLE 15

Immunodetection of Preclinical Primary Lung Cancer by hnRNP Overexpression

| PREDICTED GROUP (TEST RESULT) | | ACTUAL GROUP CANCER | ACTUAL GROUP NO CANCER |
|---|---|---|---|
| Cancer (Positive) | n = 54 | 37 (82.2%) | 17 (34.7) |
| No Cancer (Negative) | n = 40 | 8 (17.8) | 32 (65.3) |
| Total | n = 94 | 45 | 49 |

Overall Primary Lung Cancer risk: 56/6285, 0.9%
Positive Predictive Value: 37/54, 69%
Risk among Predicted Negative: 8/40, 20%

TABLE 15-continued

Immunodetection of Preclinical Primary Lung Cancer by hnRNP Overexpression

| PREDICTED GROUP (TEST RESULT) | ACTUAL GROUP CANCER | ACTUAL GROUP NO CANCER |
|---|---|---|

Relative Risk of a Positive Test: 1480/432, 3.4
Sensitivity 82% Exact 95% Binomial Confidence Interval, 68% to 92%
Specificity 65% Exact 95% Binomial Confidence Interval, 50% to 78%

Conclusions

Up-regulation of hnRNP in sputum specimens was 80% accurate in detecting a second primary lung cancer within 12 months, even though cytologic change suggestive of lung cancer was found in only one patient. In the primary lung cancer study, overexpressed hnRNP was 73% accurate in identifying preclinical primary lung cancer, while only 22% of primary lung cancers were diagnosed cytologically.

Two prospective studies accurately predicted that 67 percent and 69 percent of those with hnRNP up-regulation in their sputum would develop lung cancer in the first year of follow-up, compared with background lung cancer risks of 2.2 percent and 0.9 percent, respectively. Using sputum cells to monitor hnRNP expression therefore greatly improves the accuracy of preclinical cancer detection.

EXAMPLE 11

Fluorescence In Situ Hybridization Using Production Iodide Counterstaining For Detection of Expression of Epithelial Protein mRNA Fluorescence in situ hybridization (FISH) in combination with propidium iodide (I) counterstaining is used to demonstrate mRNA expression of epithelial protein, peptides or variants in bone sections as described by Wulf, M. et al. *Biotechniques,* Vol. 19, No. 3, pp.368–372, 1995.

After surgical removal, tissue samples are immediately fixed in 10% formaldehyde (pH 7.0) and nondecalcified, paraffin-embedded specimens are used for FISH. Pretreatment of sections before hybridization is carried out as described by Sandberg, M. et al., *J. Bone Joint Surg.,* 71:69–71, 1989. For prehybridization, sections are covered with 300 μl of prehybridization buffer (50% deionized formamide, 0.3 M NaCl 10 mM Tris-HCl, pH 7.5; 10 mM $NaHPO_4$ pH 6.8; 5 mM EDTA; 0.1× Denhardt's 10 mM dithiothreitol; 0.25 mg/ml yeast tRNA, [Sigma Chemical, St. Louis, Mo.]; 12.5% dextran sulfate; 0.5 mg/ml salmon sperm DNA [Sigma Chemical] and is incubated in a humid chamber for 2 hr at 42° C. For hybridization, a digoxigenin-labeled double-stranded cDNA probe for the epithelial protein having the sequence 5-GAGTCCGGTTCGTGTTCGTC-3' (SEQ ID NO.:11) and 5'-TGGCAGCATCAACCTCAGC-3' (SEQ ID NO.:18) are used. The probe is labeled with digoxigenin according to the protocol of the Dig-Labeling Kit (Boehringer Mannheim, Mannheim, Germany). Prior to hybridization, the labeled probe is mixed with prehybridization buffer to a concentration of 1 μg/mL, heated for 10 min. at 95° C. and quickly chilled on ice. Excess prehybridization buffer is removed from the slides, and approximately 30 μl of hybridization solution is applied to the sections. Sections are covered with a coverslip, sealed with rubber cement and hybridized in a humid chamber at 42° C. for 18 h. The post-hybridization washing steps are performed as described by Weithege, T., et al. *Pathol. Res. Pract.,* 187:912–915, 1991.

Probe detection is carried out using an anti-digoxigenin antibody conjugated to FITC (fluorescein isothiocyanate; Boehringer Mannheim). Unbound conjugate is removed by washing two times for 10 min. with phosphate-buffered saline (PBS) (3.8 mM $NaH_2PO_4$; 7.8 mM $Na_2HPO_4$; 0.13 M NaCl). Sections are counterstained with PI (Boehringer Mannheim) in PBS (500 ng/mL) for 5 min. at room temperature (30 $\mu$l per section). Excess PI is removed by washing with PBS, followed by dehydration (70%, 96%, 100% ethanol). Sections are air-dried and mounted in a glycerol/PBS solution. For analyses, a fluorescence microscope (Leitz Diaplan, Wetzlar, Germany) is used.

Using FISH, differential expression of the epithelial protein, peptide or variant mRNA in precancer and cancer cells is determined as compared to normal cells.

EXAMPLE 12

Computerized Method for Generating Predictive Discriminant Functions for Predicting Cancer Based on Computerized Image Analysis of Cellular Features The method of this invention allows one to distinguish atypical cells from normal cells and to determine or predict whether an individual will go on to develop cancer. As used herein, an atypical cell refers to a functionally and/or morphologically altered cell such as a precancer cell and cancer cell. Such a prediction may be made far in advance of any clinical signs of cancer in the individual. Prediction can be made as early as two years or more prior to any clinical signs of the cancer. Such a method is invaluable in identifying those individuals at risk for cancer and allows for early intervention of treatment to inhibit or prevent the development of cancer.

The method relys on measurement of cellular features or labels whose expression differs as compared to typical or normal cells. These features or labels may include one or more of those listed below. Image analysis in combination with appropriate statistical software allows for the identity of cellular features which are predictive of the development of cancer. The image analysis detects differences or alterations in cellular features or labels distinctive of cancer and precancer. Various parameters may be labeled and measured as indicators or predictors of cancer including but not limited to alterations in morphology increased or altered mRNA expression, increased or altered cancer proteins, expression of a cellular receptor or alternatively a decline in cellular receptor, factors associated with apoptosis or other cellular events which are unique to precancer or cancer cells.

The present method of predicting cancer has distinct advantages in that it is computer assisted, and highly accurate in predicting cancer development.

Archived tissues or cells taken from known positive cancer patients, patients known to develop cancer and negative individuals known to remain negative are used to provide specimens for the image analysis method for determining the parameters unique to cancer and precancer cells. Based on the measured cell labels or features, a discriminant function may be derived from the best linear combination of parameters which distinguishes specimens of individuals who develop cancer compared with those that remain cancer free. This discriminant function is useful for predicting cancer in unknown samples.

In some cases it is advantageous to add a labeled probe or a chromogen to identify on additional parameter to use in detecting cellular features unique to cancer and precancer. A labeled probe, for example, may specifically identify mRNA, DNA, protein, glycoprotein, cellular receptors, carbohydrate and the like which are modulated in some fashion in cancer or precancer as compared to normals. In one embodiment, the labeled probe detects hn-RNP mRNA.

The image analysis may be made from any spatial electronic array such as that recorded during video microscopy by a charge coupled device (CCD) camera, analog or digital, whether recording transmitted, reflected, or fluorescent illumination. Any image that distinguishes cancer or precancer from normal cells, tissue or extracts may be used in the present invention to determine a discriminant function predictive of cancer or precancer.

Commercial packages such as MetaMorph 2.x (Universal Imaging Corporation, West Chester, Pa.) are available to automatically measure more than 100 features of a cell. By referring to the "Measure" menu and selecting "Configure Object Measurements", the user can select the measurements to calculate and log to a data file. For example, the 108 possible measurements in MetaMorph's "Object Classifer Set", Version 2.1 are presented below:

"Total area", "Pixel area", "Area", "Hole area", "Relative hole area", "Standard area count", "Perimeter", "Centroid X", "Centroid Y", "Width", "Height", "Orientation", "Length", "Breadth", "Fiber length", "Fiber breadth", "Shape factor", "Ell. form factor", "Inner radius", "Outer radius", "Mean radius", "Equiv. radius", "Equiv. sphere vol.", "Equiv. prolate vol.", "Equiv. oblate vol.", "Equiv. sphere surface area", "Average gray value", "Total gray value", "Optical density", "Integrated OD", Intensity center X", "Intensity center Y", "Radial dispersion", "Texture Difference Moment", "Texture Inverse Difference Moment", "OD Variance", "OD Relative Low Area", "OD Relative Medium Area", "OD Relative High Area", "OD Relative Low Amount", "OD Relative Medium Amount", "OD Relative High Amount", "OD Relative Low Distance", "OD Relative Medium Distance", "OD Relative High Distance", "EFA Harmonic A0", "EFA Harmonic C0", "EFA Harmonic 2, Semi-Major Axis", "EFA Harmonic 2, Semi-Minor Axis", "EFA Harmonic 2, Semi-Major Axis Angle", "EFA Harmonic 2, Ellipse Area", "EFA Harmonic 2, Axial Ratio", EFA Harmonic 3, Semi-Major Axis", EFA Harmonic 3, Semi-Minor Axis", "EPA Harmonic 3, Semi-Major Axis Angle", "EFA Harmonic 3, Ellipse Area", "EFA Harmonic 3, Axial Ratio", "EFA Harmonic 4, Semi-Major Axis", "EFA Harmonic 4, Semi-Minor Axis", EFA Harmonic 4, Semi-Major Axis Angle", EFA Harmonic 4, Ellipse Area", "EFA Harmonic 4, Axial Ratio", "EFA Harmonic 5, Semi-Major Axis", "EFA Harmonic 5, Semi-Minor Axis", "EFA Harmonic 5, Semi-Major Axis Angle", "EFA Harmonic 5, Ellipse Area", "EFA Harmonic 5, Axial Ratio", "EFA Harmonic 6, Semi-Major Axis", "EFA Harmonic 6, Semi-Minor Axis", "EFA Harmonic 6, Semi-Major Axis Angle", "EFA Harmonic 6, Ellipse Area", "EPA Harmonic 6, Axial Ratio", "EFA Harmonic 7, Semi-Major Axis", "EFA Harmonic 7, Semi-Minor Axis", "EFA Harmonic 7, Semi-Major Axis Angle", "EFA Harmonic 7, Ellipse Area", "EPA Harmonic 7, Axial Ratio", "EFA Harmonic 8, Semi-Major Axis", "EFA Harmonic 8, Semi-Minor Axis", "EFA Harmonic 8, Semi-Major Axis Angle", "EFA Harmonic 8, Ellipse Area", "EFA Harmonic 8, Axial Ratio", "EFA Harmonic 9, Semi-Major Axis", "EFA Harmonic 9, Semi-Minor Axis", "EFA Harmonic 9, Semi-Major Axis Angle", "EFA Harmonic 9, Ellipse Area", "EFA Harmonic 9, Axial Ratio", "EFA Harmonic 10, Semi-Major Axis", "EFA Harmonic 10, Semi-Minor Axis", "EFA Harmonic 10, Semi-Major Axis Angle", "EFA Harmonic 10, Ellipse Area", "EFA Harmonic 10, Axial Ratio", "EFA Harmonic 11, Semi-Major Axis", "EFA Harmonic 11, Semi-Minor Axis", "EFA Harmonic 11, Semi-Major Axis Angle", "EFA Harmonic 11, Ellipse Area", "EFA Harmonic 11, Axial Ratio", "EFA Harmonic 12, Semi-Major Axis", "EFA Harmonic 12, Semi-Minor Axis", "EFA Harmonic 12, Semi-Major Axis Angle", "EFA Harmonic 12, Ellipse Area", "EPA Harmonic 12, Axial Ratio", "EFA Harmonic 13, Semi-Major Axis", "EPA Harmonic 13, Semi-Minor Axis", "EFA Harmonic 13, Semi-Major Axis Angle", "EFA Harmonic 13, Ellipse Area", "EFA Harmonic 13, Axial Ratio".

Powerful commercial statistical packages such as SPSS 7.0 for Windows (SPSS, Inc., Chicago, Ill.) are available for microcomputer data management and analysis. The algorithms are identical to those used in SPSS software on mainframe computers, and the statistical result will be as precise as those computed on a mainframe.

The SPSS package includes discriminant analysis which provides direct prediction of group membership. In this procedure, the best linear combination of variables is automatically selected for distinguishing among several groups. Coefficients for the variables are chosen by the computer to make the ratio of between-groups sums of squares to total sums of squares as large as possible.

The present invention provides a method for determining a discriminant function algorithm using commercial statistical package to select and weight an optimal combination of cellular measurements (made by a commercial imaging package) to provide a direct prediction of group membership (precancer or cancer case or control).

In one embodiment, a discriminant function for predicting lung cancer utilizes the parameters of optical density, nuclear texture difference moment and nuclear area of the elliptical Fourier harmonic which provides an accuracy of about 100% in predicting those individuals who will go on to develop cancer. In the case where a lower accuracy is satisfactory, the discriminant function may be based on optical density alone, without the nuclear parameters.

Different tissue or epithelial cells from different locations may utilize the same discriminant function or an alternative discriminant function. The method of determining a discriminant function may lead to selection of alternative sets of variables, with corresponding different coefficients depending on the tissue, cell type and the degree of accuracy desired. This method of image analysis with a discriminant function calculated from a prospective collection of archived specimens of patients with known clinical outcome allows for the determination of a predictive discriminant function equation. Thus, the method is useful in determining a predictive discriminant function equation for any cancer for which prospective specimens may be obtained including but not limited to cancer of the lung, breast, liver, prostate, uterus, ovary, gastrointestinal tract, esophagus and the like. Such a discriminant function used in image analysis allows for prediction of individuals who will go on to develop cancer.

EXAMPLE 13

Method for Developing A Discriminant Function Predictive of Lung Cancer Based On Dual-Wavelength Image Densitometry of Archived Sputum Cells with Labeled hnRNP mRNA Up-regulated hnRNP mRNA may be recognized visually by the intensity and frequency of epithelial cells labeled with biotin-11-UTP and immunostained by peroxidase-DAB. Visual interpretation compares the "differential display" of immunolabeled informative (mildly atypical) epithelial cells to background (mature) epithelial cells. Accuracy has been improved by objective measurement of light intensity transmitted through immunolabeled epithelial cells using video microscopy. Performed at 600 nm and 510 nm, two wavelengths of light optimized to the staining chromogens, this technique is called dual-wavelength image densitometry, and measurements are made as follows:

1. Koehler illumination (standard laboratory practice)

Begin by adjusting the microscope for Koehler illumination to achieve the brightest, uniformly illuminated field. These adjustments provide that light rays from the light source (in focus in the conjugate "aperture" planes, which include the light source, and the aperture diaphragm) are parallel when passing through the conjugate "field" planes (which include the specimen, the field diaphragm and the retina).

a. Bring specimen into focus with appropriate objective. In the present study the specimens were imaged at (50×).

b. Reduce the aperture and field diaphragms and focus the condenser until a sharp image of the field diaphragm is superimposed on the specimen.

c. Open the field diaphragm just beyond the visual field.

d. Adjust the aperture diaphragm to maximize the dynamic range of the CCD (charge coupled device) video camera without saturation.

The following steps have been programmed into the Measurements Menu "Optical Density Application," of the MetaMorph Image Analysis Program, Universal Imaging Corp, West Chester, Pa., identified in the file structure as the "Tockman.out" drop-in.

2. Calibrate CCD and Acquire Control Images (Acquires 11 reference images)

a. Prepare a dark reference image to be used for densitometry. The dark reference is acquired by averaging 16 frames with the light source blocked.

b. Prepare a white reference image. The white reference is acquired by averaging 16 frames of a blank section of the specimen slide with the 600 nm filter in place. A second white reference is acquired with the 510 nm filter in place. The dark reference is subtracted pixel by pixel from the white reference images prior to storage (Background subtraction).

c. Acquire the 1st neutral density image. Placing a 0.2 neutral density filter in the light path, 16 frames of a blank section of the specimen slide are averaged at 600 nm. Prior to storage, this image is divided (pixel by pixel) by the background subtracted white reference image to correct for optical and illumination irregularities (Shading Correction). This procedure is repeated at 510nm.

d. Acquire the 2nd neutral density image. After placing a 0.4 neutral density filter in the light path, the procedures in (c) are repeated.

e. Plot density calibration. After averaging the transmitted light recorded by the CCD for dark, white, 1st and 2nd neutral density images the computer constructs a four point calibration curve of gray scale light intensity (on an 8-bit, 256 interval ordinate) against optical density (abscissa). One calibration curve is constructed for each wavelength. The calibration curves for the first day are arbitrarily selected as the standard curves, and calibration curves from the subsequent measurement sessions are standardized to these, assuring comparability of measurement values during the course of an experiment.

f. Acquire positive control images. Immunostained Calu-3 cultured lung cancer cell hybridized with the mRNA antisense probe are selected. The cell image at 600 nm is acquired after averaging 16 frames, background subtraction and shading correction. A second image is acquired at 510 nm without any change in cell position (registration) by automatically rotating the filter wheel.

g. The negative control images are acquired in a similar fashion from an identical control slide to which the sense probe has been hybridized.

3. Acquire an Image Pair

Each test slide is scanned by a cytotechnologist who selects epithelial cell fields for imaging. Each image is acquired first at 600 nm and then at 510 nm by averaging 16 frames, background subtraction and shading correction without change in registration. Each image pair is saved to a "stack" of images for the same patient. Each stack is saved to the optical disk file which includes the stack of 11 reference images.

4. Measure an Image Pair (Prior to measurement, the computer checks the integrity of the reference stack, standardizes the densitometry calibration, retrieves the stack of patient images and places the image of the first field on the computer screen.)

a. Select the nucleus to be measured. A mouse click when the cursor overlies the nucleus of the first cell to be measured causes the computer to enlarge the cell 400× and place it in the center of the field.

b. Outline the nucleus region of interest. Rapidly dragging the mouse outlines the nucleus to separate it from other structures in the image.

c. Threshold the nucleus. The actual margins of the nucleus are determined by the pixel values of transmitted light. The threshold of included values is raised and lowered by the technician until a best fit is achieved.

d. Measure the nucleus. More than 100 separate measurements may be made and recorded electronically to an Excel spreadsheet by a dynamic data entry (DDE) link. In one embodiment, the measurements which most contribute to the separation of cells by cancer outcome are:

Nuclear Texture Difference Moment. This measurement is based on the number of sign changes proceeding from pixel-to-pixel across the nucleus. A texture difference moment of 0 indicates uniform gray. Higher values indicate coarse clumping.

Area of the Elliptical Fourier Harmonic #9. This application of the Fast Fourier Transform (FFT) analyzes periodic data in a closed contour. Based on the work of Kuhl and Giardina (Computer Graphic Image Proc 1982;18:236–58), this procedure recognizes finer variation as higher order Fourier harmonics. Here, nuclei with a smaller proportion of their area (in pixels) as 9 pointed shapes seem to be discriminatory. Larger values indicate a larger area.

e. Outline the cytoplasm region of interest at 600 nm. Rapidly dragging the mouse outlines the image of the cell cytoplasm at 600 nm.

f. Threshold the cytoplasm. The actual margins of the cytoplasm are determined by the pixel values of transmitted light. The threshold of includes values is raised and lowered by the technician until a best fit is achieved.

g. Measure the cytoplasm at 600 nm. The nucleus is converted into a binary mask which is subtracted from the cytoplasmic image. Similar to the nucleus, more than 100 separate measurements may be made and recorded electronically to an Excel spreadsheet by a dynamic data entry (DDE) link. In one embodiment, the measurements which most contribute to the separation of cells by cancer outcome are:

Average cytoplasmic density at 600 nm. The optical density of the cytoplasm at 600 nm is determined by the average measured pixel gray level and the standardized calibration table.

h. Outline the cytoplasm region of interest at 510 nm. Rapidly dragging the mouse outlines the image of the cell cytoplasm at 510 nm.

i. Threshold the cytoplasm. The actual margins of the cytoplasm are determined by threshold as above.

j. Measure the cytoplasm at 510 nm. At present, the measurements which most contribute to the separation of cells by cancer outcome are:

Average cytoplasmic density at 510 nm. The optical density of the cytoplasm at 510 nm is determined by the average measured pixel gray level and the standardized calibration table.

5. The linear discriminant Function Data Analysis (This is a commercially available routine for the PC by SPSS Inc., Chicago, Ill.).

a. Excel measurement data are entered into the SPSS program to find linear combinations of dependent variables that best separate specimens from individuals who later develop cancer from those who remain cancer free.

b. With outcome groups set as cancer or not cancer, and the dependent variables as the average cytoplasmic optical density at 510 nm, the average cytoplasmic optical density at 600 nm, the nuclear texture difference moment and the area of the nucleus described by elliptical fourier texture difference moment and the area of the nucleus described by elliptical fourier harmonic 9, have produced complete discrimination of sputum specimens from Johns Hopkins Lung Project (JHLP) participants who went on to develop cancer compared to those who remained cancer free.

These measurements are combined into a new discriminant function:

$$D=\beta_0+\beta_1(\text{Optical Density}_{600})+\beta_2(\text{Optical Density}_{510})+\beta_3(\text{Nuclear Texture Differ.})+\beta_4(\text{Nuclear Ellipse area at Fourier Harmonic 9})$$

The unstandardized values for these JHLP weights are

| | |
|---|---|
| $\beta_2$ = CYAVOD51 | −8.1834331 |
| $\beta_1$ = CYAVOD60 | −16.7053961 |
| $\beta_3$ = NUCTXDIF | 5.5935067 |
| $\beta_4$ = NUCTXDIF | 58.8520016 |
| $\beta_0$ = (Constant) | −5.5977584 |

EXAMPLE 14

Early Detection of Lung Cancer by In-Situ Hybridization to the Messenger-RNA of (hnRNP) A2/B1

Only a minority of cells in the sputum of individuals who later develop lung cancer over-express the hnRNP antigen. To understand the temporal course and the causes for hnRNP up-regulation, a tissue in situ hybridization assay was modified for use in exfoliated sputum cells.

Figure 14:
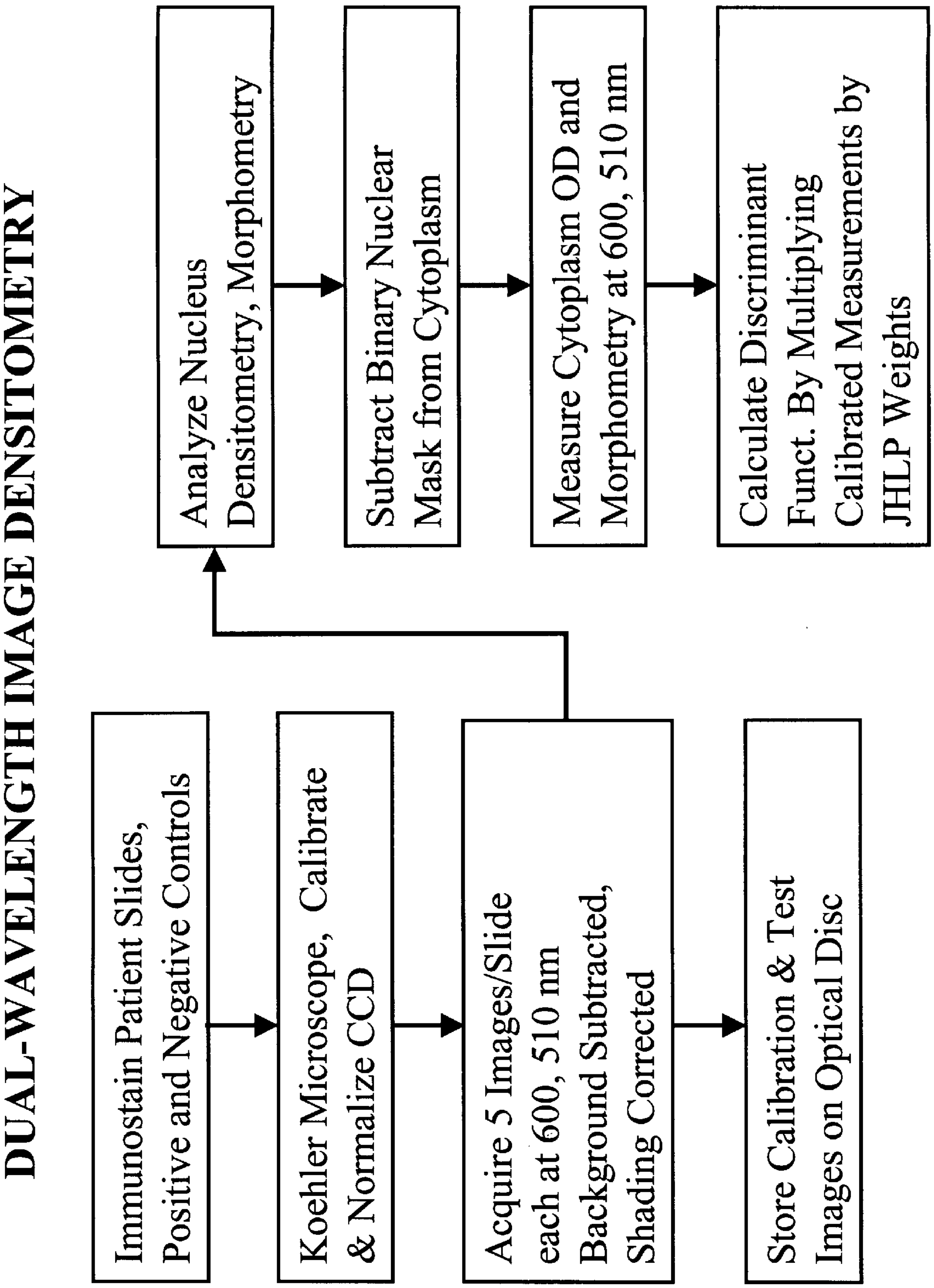
FIG. 14 shows standardization and calibration procedure for dual-wavelength image densitometry.

The immunocytochemistry assay of sputum specimens had demonstrated a low level of background expression in normal sputum cells (U.S. Pat. No. 5,455,159), and provided the impetus to develop a dual-wavelength image densitometry technique to quantify enhanced antigen presence for early lung cancer detection (Tockman, et al. 1993, *Diagnostic Cytopathol,* vol. 9(6):615–22). Dual-wavelength image densitometry depends upon a series of carefully standardized and calibrated procedures (See FIG. 14) to assure reliable measurement of cytoplasmic optical density at 600 nm and 510 nm. Computerized interpretation of protein antigen densitometry combines these optical densities into a discriminant function.

$$D=\beta_0+\beta_1\ (\text{Optical Density}_{600})^{1/2}-\beta_2(\text{Optical Density}_{510})^{1/2}$$

The potential for altered nuclear distribution and impaired mobility of the hnRNP across nuclear membranes has led to measurement of additional cellular features and development of a new discriminant function. The modified algorithm for image densitometry has accurately quantitated hnRNP messenger RNA expression in the same JHLP specimens used to validate the expression of hnRNP protein, resulting in a more accurate detection of early lung cancer.

Methods

Clinical Materials. As previously described, the John Hopkins Lung Project (JHLP) conducted cytologic screening on induced sputum specimens from 5,226 middle-aged, male smokers between 1976 and 1984 (U.S. Pat. No. 5,455,159; Tockman, et al. 1989 *J. Clin. Oncol.,* vol 6:1685–93). During the course of up to 8 years of annual screening, 626 (12%) of these participants had moderate or greater atypia on one or more of their sputum specimens. All such specimens plus follow-up material were individually placed in Saccomanno's preservative solution (SPS, 2% polyethylene glycol in 50% ethanol) and stored (Saccomanno, et al. 1963 *Acta Cytol.,* vol. 7:305–10). 86 of these individuals developed lung cancer during follow-up. A random selection of these specimens, stratified to include examples of each major lung cancer cell type (adenocarcinoma, squamous cell carcinoma, large cell undifferentiated, and small cell undifferentiated), provided 22 sputum specimens collected, on average, two years prior to the development of clinical lung cancer. Morphologically similar specimens from individuals who did not develop cancer were used as controls. Archived material remains available on 13 of these individuals, 8 of whom developed cancer (3 squamous, 3 small call undifferentiated, 2 adenocarcinoma) and 5 who remained cancer-free.

In-situ Hybridization. Single-stranded RNA probes of 1.6 kb and 1.8 kb transcribed by phage polymerases from plasmids containing SP6 and T7 promoters were used and were made as described herein. Cytologic specimens and control material, prefixed in SPS, were cytospun (Shandon, Pittsburgh, Pa.) onto sialated, RNAse free glass slides (American Histo). Calu-3 (ATCC human bronchogenic adenocarcinoma cell line) was mixed with normal sputum and used as control material. Pretreatment optimization included the following procedures. After 4% paraformaldehyde (Sigma) post-fixation for 1 hr. at room temperature, we treated the slides with 0.1M Tris/50 mM EDTA (pH 8.0) prewarmed to 37° C. containing 10 $\mu$g/ml proteinase K (Gibco BRL) for 10 min. to increase probe access. Acetylation with 0.25% acetic anhydride and 0.1M triethanolamine solution (pH 8.0, sigma) for 10 min. is used to decrease background binding. Probes are labeled with 10 nmol/$\mu$l digoxigenin-11-UTP (Boehringer Mannheim).

The in situ hybridization procedure follows that of Cox et al. (*Dev. Biol.* 1984; 101: 485–502. Hybridization of one set of slides was conducted to an antisense single-stranded riboprobe to detect specific hybridization. In parallel, under identical conditions, a second set of slides was hybridized to the sense riboprobe to detect nonspecific background hybridization. As a second control, a third set of slides was treated with RNAse prior to antisense probe hybridization to detect any signal which may result from binding to non-RNA cell components. Immunocytochemistry is used to detect the digoxigenin-labeled, hybridized probe. After post-hybridization stringency washes and RNAse rinse, the slides undergo peroxidase diaminobenzidine (DAB) staining (Vector Laboratories, Burlingame, CA) with hematoxylin counterstain.

Dual-Wavelength Image cytometry. Sputum epithelial cells with regular metaplasia were visually selected by a cytotechnologist who had no knowledge of the patients' clinical status. After 2 slides per patient were scanned, 5 to 10 characteristic fields were selected for each subject. Koehler illumination, followed by neutral density filter standardization of light transmission was established. Slides were imaged on a Zeiss Axiomat microscope (Carl Zeiss, Oberkochen, Germany). To optimize the transmitted light for the brown diaminobenzidine-labeled digoxigenin and the blue (hematoxylin) counterstain, Omega narrow-band filters of 600 nm (range 590 to 610 nm) and 510 nm (range 500 to 520 nm), respectively, were used (Tockman, et al. 1992 *Cancer Res.,* vol. 52 (Suppl); 27115-8S.) Transmission was detected by a high resolution video camera (Hamamatsu Photonic Systems, Japan) interfaced to a digital image processor (Metamorph v 2.0, Universal Imaging, West Chester, Pa.). Background-subtracted, shading-corrected images of each field at both wavelengths were then recorded to an optical drive (Panasonic/Matsushita Co., Osaka).

After shading correction to account for illumination and camera sensor non-uniformities, optical density values are measured at 600 nm and 510 nm as previously determined from the transmittance spectrum of the chromogen labels. Nuclear texture analysis is based on the number of sign changes in pixel-to-pixel comparisons (nuclear texture difference moment), with larger values indicating coarse clumping. The shape of the nuclear membrane is determined by evaluating the Fourier power at various frequency ranges. Greater irregularity is reflected as increased cytoplasmic area high Fourier harmonics. These measurements are combined into a new discriminant function:

$$D=\beta_0+\beta_1(\text{Optical Density}_{600})+\beta_2(\text{Optical Density}_{510})+\beta_3(\text{Nuclear Texture Differ.})+\beta_3(\text{Nuclear Elipse area at Fourier Harmonic 9})$$

RESULTS

Figure 15:
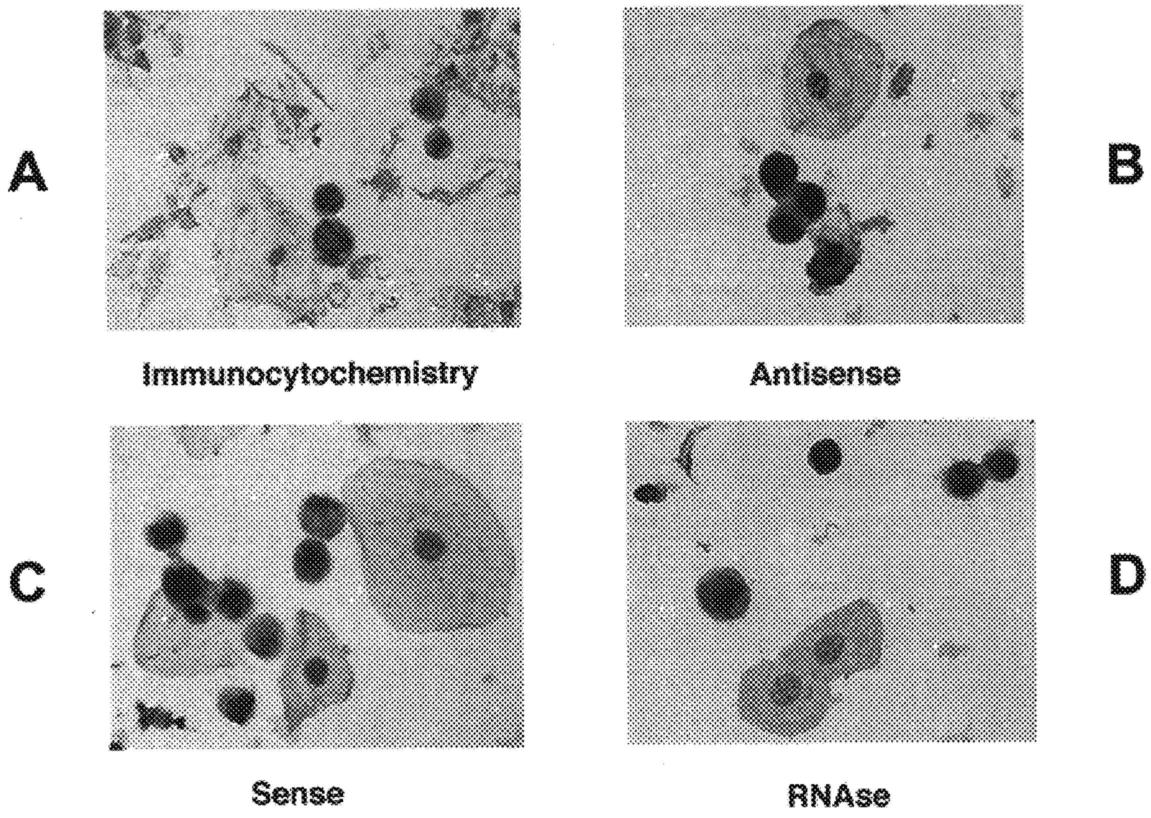
FIGS. 15A–15D show expression of hnRNP A2 mRNA/protein in a control mixture of Calu-3 cells plus normal sputum cells.

The expression of hnRNP A2 messenger RNA and protein in positive and negative control specimens are presented in FIGS. 15*a–d*. FIG. 15*a,* labeled "immunocytochemistry," shows mature squamous epithelial cells in normal sputum mixed with cultured Calu-3 adenocarcinoma cells. The normal epithelial cells display small nuclei with extensive cytoplasm, expressing a normal (background) level of hnRNP detected by monoclonal antibody 703D4 and faintly stained with DAB. The cultured tumor cells have large nuclei with a small rim of densely staining cytoplasm indicating hnRNP up-regulation. FIG. 15*b* (labeled "antisense") shows similar positive control material expressing specific mRNA hybridization labeled with DAB. Note the similarity of spatial expression to the hnRNP protein (FIG. 15*a*). FIGS. 15*c* ("Sense") and 15*d* ("RNAse") present the in situ hybridization negative controls.

Figure 16:
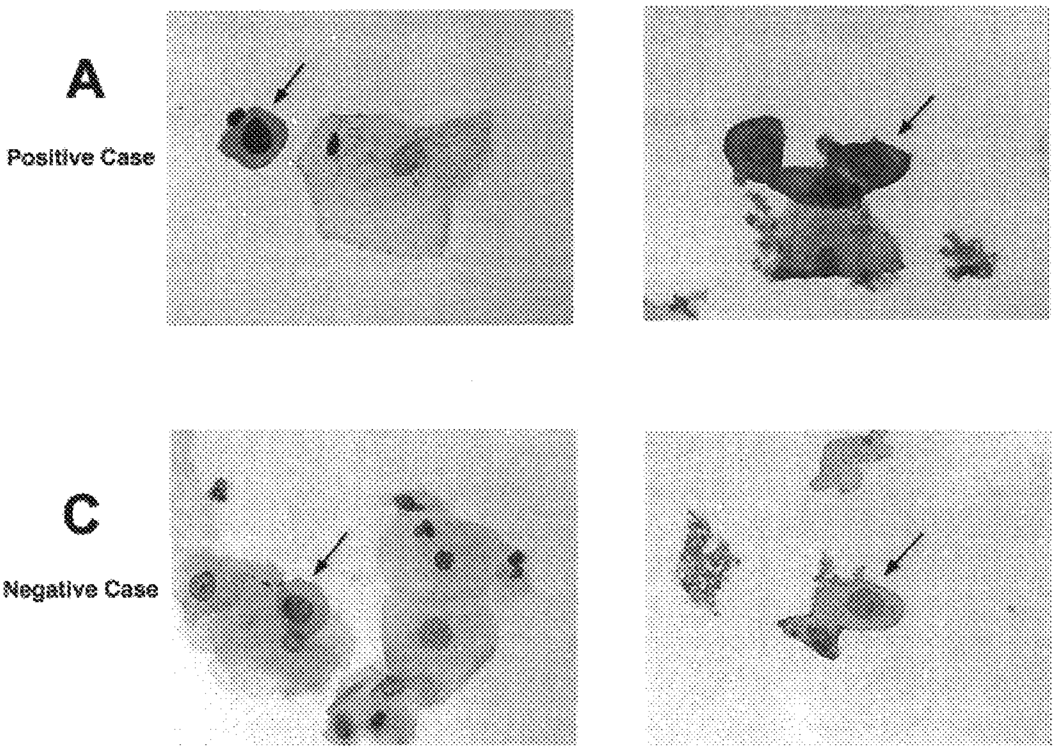
FIGS. 16A–16D show expression of hnRNP A2 mRNA/protein in clinical sputum cells.
Figure 17:
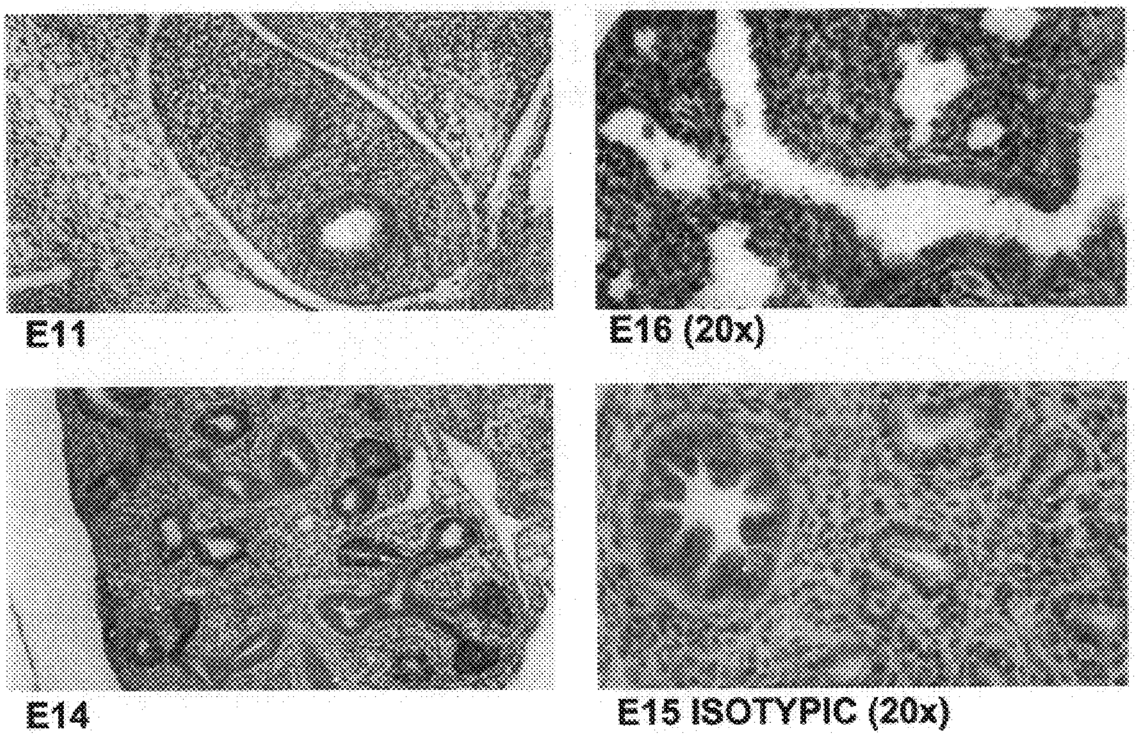
FIGS. 17A–17D show expression of hnRNP in developing mouse lung.

In FIGS. 16*a–d,* the expression of hnRNP A2 messenger RNA and protein is contrasted between a positive case (FIGS. 16*a,* 16*b*) and a negative case (FIGS. 16*c,* 16*d*). In the upper row, two aliquots of a specimen from a patient who later developed squamous lung cancer illustrates mild morphologic atypia and positive expression of hnRNP protein (FIG. 16*a*) and hnRNP messenger RNA (FIG. 16*b*). In the lower row, similar assays of the sputum of a patient who did not develop lung cancer show neither over-expression of protein nor of messenger RNA despite similar cellular morphology.

Table 16 shows the group means and standard deviations for the specific variables measured on the hybridized sputum cells of individuals who later developed cancer and those who remained cancer-free. Although the sample is small, the carefully made measurements demonstrate significantly greater optical densities (message expression) of the cells of patients who later develop cancer, significantly less fine folding of the nuclear membrane and coarser nuclear clumping (which just fails to reach statistical significance, Table 17). Although the values of specific variables are strongly suggestive, individually they do not successfully predict the subsequent development of cancer.

TABLE 16

| Clinical | | CYAVOD51 | CYAVOD60 | NUCTXDIF | NEFAHAR9 |
|---|---|---|---|---|---|
| | | Group means | | | |
| Outcome | | | | | |
| Noncancer | n = 5 | .37296 | .37706 | 1.94926 | .11760 |
| Cancer | n = 8 | .54558 | .55011 | 2.32015 | .07474 |
| Total | n = 13 | .47919 | .48355 | 2.17750 | .09123 |
| | | Group standard deviations | | | |
| Outcome | | | | | |
| Noncancer | n = 5 | .03674 | .03455 | .46603 | .03796 |
| Cancer | n = 8 | .06402 | .06763 | .14906 | .02072 |
| Total | n = 13 | .10235 | .10366 | .34732 | .03467 |

TABLE 17

| Wilks' Lambda (U-statistic) and univariate F-ratio with 1 and 11 degrees of freedom | | | |
|---|---|---|---|
| Variable | Wilks' Lamdba | F | Significance |
| CYAVOD51 | .27057 | 29.6553 | .0002 |
| CYAVOD60 | .28537 | 27.5471 | .0003 |
| NUCTXDIF | .70760 | 4.5456 | .0564 |
| NEFAHAR9 | .60801 | 7.0919 | .0221 |

DISCRIMINANT ANALYSIS

On groups defined by TWOUTCM

Analysis number 1

Direct method: all variables passing the tolerance test are entered.

Minimum tolerance level .00100

Canonical Discriminant Functions

TABLE 17-continued

Maximum number of functions
Minimum cumulative percent of variance 100.00
Maximum significance of Wilks' Lambda 1.0000
Prior probability for each group is .50000
Classification function coefficients
(Fisher's linear discriminant functions)

| TWOUTCM = | 1 | 2 |
|---|---|---|
| CYAVOD51 | 1104.0237635 | 1142.7674226 |
| CYAVOD60 | −1273.2985274 | −1194.6819128 |
| NUCTXDIF | 137.2456245 | 110.7637170 |
| NEFAHAR9 | 1433.1731052 | 1154.5440928 |
| (constant) | −184.5560010 | −155.4676693 |

Canonical Discriminant Functions

| Fcn | Eigenvalue | Pct of Variance | Cum PCT | Canonical Corr | After Fcn | Wilks' Lambda | Chi-Square | df | Sig |
|---|---|---|---|---|---|---|---|---|---|
| | | | | | 0 | .137555 | 17.854 | 4 | .0013 |
| 1* | 6.2698 | 100.00 | 100.00 | .92787 | | | | | |

*Marks the 1 canonical discriminant functions remaining in the analysis.
Standardized canonical discriminant function coefficients

| | Func 1 |
|---|---|
| CYAVOD51 | −.45504 |
| CYAVOD60 | −.96039 |
| NUCTXDIF | 1.70686 |
| NEFAHAR9 | 1.66169 |

Structure maxtrix:
Pooled within-groups correlations between discriminating variables and canonical discriminant functions
(Variables ordered by size of correlation within function)

| | Func 1 |
|---|---|
| CYAVOD51 | −.65573 |
| CYAVOD60 | −.63200 |
| NEFAHAR9 | .32067 |
| NUCTXDIF | −.25673 |

Unstandarized canonical discriminant function coefficients

| | Func 1 |
|---|---|
| CYAVOD51 | −8.1834331 |
| CYAVOD60 | −16.6053961 |
| NUCTXDIF | 5.5935067 |
| NEFAHAR9 | 58.8520016 |
| (Constant) | −5.5977584 |

Canonical discriminant functions evaluated at group means (group centroids)

| Group | Func 1 |
|---|---|
| 1 | 2.91348 |
| 2 | −1.82092 |

| Case | Mis | | Actual | Highest Probability | | | 2nd Highest | | Discrim |
|---|---|---|---|---|---|---|---|---|---|
| No. | Val | Sel | Group | Group | P(D/G) | P(G/D) | Group | P(G/D) | Scores |
| 1 | | | 2 | 2 | .3001 | 1.0000 | 1 | .0000 | −2.6571 |
| 2 | | | 2 | 2 | .4501 | .9995 | 1 | .0005 | −1.0656 |
| 3 | | | 2 | 2 | .7782 | .9999 | 1 | .0001 | −1.5393 |
| 4 | | | 2 | 2 | .4901 | .9996 | 1 | .0004 | −1.1307 |
| 5 | | | 2 | 2 | .1653 | .9904 | 1 | .0096 | −.4334 |
| 6 | | | 2 | 2 | .5001 | 1.0000 | 1 | .0000 | −2.4952 |
| 7 | | | 2 | 2 | .2680 | 1.0000 | 1 | .0000 | −2.9286 |
| 8 | | | 2 | 2 | .7668 | 1.0000 | 1 | .0000 | −2.1174 |
| 9 | | | 1 | 1 | .3916 | 1.0000 | 2 | .0000 | 3.7702 |
| 10 | | | 1 | 1 | .8095 | 1.0000 | 2 | .0000 | 3.1546 |
| 11 | | | 1 | 1 | .1979 | .9940 | 2 | .0060 | 1.6258 |
| 12 | | | 1 | 1 | .2922 | .9980 | 2 | .0020 | 1.8602 |
| 13 | | | 1 | 1 | .2138 | 1.0000 | 2 | .0000 | 4.1566 |

The calculated discriminant functions are shown in a histogram in Table 18. The discriminant functions of the sputum cells of those who develop cancer are clearly separated from those of individuals who remain cancer-free. This conclusion is supported by the classification table (Table 19). This table shows that determination of hnRNP messenger RNA expression by dual wavelength image cytometry can distinguish sputum cells archieved two years in advance of clinical cancer of individuals who will develop lung cancer from those who remain cancer free.

TABLE 18

Symbols used in plots

| Symbol | Group | Label |
|---|---|---|
| 1 | | Noncancer |
| 2 | | Cancer |

```
        4+              All-groups Stacked Histogram                       +
         I              Canonical Discriminant Function 1                  I
         I                                                                 I
  F      I                                                                 I
  r     3+                                                                 +
  e      I                                                                 I
  q      I                                                                 I
  u      I                                                                 I
  e     2+                                                                 +
  n      I                                                                 I
  c      I                                                                 I
  y      I                                                                 I
        1+                                                                 +
         I          22  22  2  22  2         11        11  1               I
         I          22  22  2  22  2         11        11  1               I
         I          22  22  2  22  2         11        11  1               I
                    22  22  2  22  2         11        11  1
         x-------+---------+---------+---------+---------+--------X
        out    -4.0      -2.0        .0       2.0       4.0      out

 Class     2222222222222222222222222222222222221111111111111111111111111
 Centroids                   2                        1
```

TABLE 19

| Classification results - | | | |
|---|---|---|---|
| | No. of | Predicted Group Membership | |
| Actual Group | Cases | Noncancer | Cancer |
| Noncancer | 5 | 5<br>100.0% | 0<br>.0% |
| Cancer | 8 | 0<br>.0% | 8<br>100.0% |

Percent of "group" cases correctly classified: 100.00%

Classification processing summary 13 (Unweighted) cases were processed.

0 cases were excluded for missing or out-of-range group codes.

0 cases had at least one missing discriminating variable.

13 (Unweighted) cases were used for printed output.

For comparison, hnRNP protein expression in the same 13 sputum specimens is evaluated in a similar discriminant function analysis (Tables 20–24). Table 20 shows the group means and standard deviations for the optical densities measured on the immunostained sputum cells of individuals who later developed cancer and those who remained cancer-free. Although a trend is apparent, measurement variability and the small sample size preclude a significant difference (Table 21).

TABLE 20

| Clinical | | CYVOD51 | CYAVOD60 |
|---|---|---|---|
| Group means | | | |
| Outcome | | | |
| Noncancer | n = 5 | .27056 | .27131 |
| Cancer | n = 8 | .34531 | .34419 |
| Total | n = 13 | .31656 | .31616 |

TABLE 20-continued

| Clinical | | CYVOD51 | CYAVOD60 |
|---|---|---|---|
| Group standard deviations | | | |
| Outcome | | | |
| Noncancer | n = 5 | .11262 | .11309 |
| Cancer | n = 8 | .10508 | .10503 |
| Total | n = 13 | .11001 | .10982 |

TABLE 21

Wilks' Lambda (U-statistic) and univariate F-ratio with 1 and 11 degrees of freedom

| Variable | Wilks' Lambda | F | Significance |
|---|---|---|---|
| CYAVOD51 | .88160 | 1.4772 | .2496 |
| CYAVOD60 | .88707 | 1.4003 | .2616 |

The greater variability in the densitometry of hnRNP protein expression is demonstrated by the overlapping discriminant function scores shown in the histogram in Table 22. The discriminant functions of the sputum cells measured only for protein expression show both false positive and false negative results. This conclusion is supported by the classification table (Table 23). This table shows that hnRNP protein expression can accurately distinguish 77% of the sputum specimens archived two years in advance of clinical cancer of individuals who will develop lung cancer from those who remain cancer free.

TABLE 22

```
Symbols used in plots
Symbol  Group  Label

1              Noncancer
2              Cancer

      4+            All-groups Stacked Histogram                     +
       I            Canonical Discriminant Function 1                I
       I                                                             I
F      I                                                             I
r     3+                                                             +
e      I             2                                               I
q      I             2                                               I
u      I             2                                               I
e     2+             2                                               +
n      I             1                                               I
c      I             1                                               I
y      I             1                                               I
      1+             1                                               +
       I          21 11      2   22    22  2  1                      I
       I          21 11      2   22    22  2  1                      I
       I          21 11      2   22    22  2  1                      I
                  21 11      2   22    22  2  1
      x--------+--------+--------+--------+---------------+--------X
      out     -2.0     -1.0      .0      1.0             2.0      out

 Class  111111111111111111111111111111112222222222222222222222222222222222
Centroids                          1       2
```

| TABLE 23 | | | |
|---|---|---|---|
| Classification results - | | | |
| | No. of | Predicted Group Membership | |
| Actual Group | Cases | Noncancer | Cancer |
| Noncancer | 5 | 4<br>80.0% | 1<br>20.0% |
| Cancer | 8 | 2<br>25.0% | 6<br>75.0% |

Percent of "group" cases correctly classified: 76.92%

Classification processing summary 13 (Unweighted) cases were processed.

0 cases were excluded for missing or out-of-range group codes.

0 cases had at least one missing discriminating variable.

13 (Unweighted) cases were used for printed output.

While this result represents a great step forward over current clinical practice, the further improvement in accuracy of early detection by hnRNP messenger RNA over protein expression in the same specimens is apparent (Table 24).

TABLE 24

| hnRNP Protein vs. hnRNP mRNA Expression in Archieved Sputum | | |
|---|---|---|
| | Developed Lung Cancer | |
| Assay Result | Yes | No |
| Immunocytochemistry | | |
| Positive | 6 | 1 |
| Negative | 2 | 4 |
| Accuracy | 77% | |

TABLE 24-continued

| hnRNP Protein vs. hnRNP mRNA Expression in Archieved Sputum | | |
|---|---|---|
| | Developed Lung Cancer | |
| Assay Result | Yes | No |
| In Situ Hybridization | | |
| Positive | 8 | 0 |
| Negative | 0 | 5 |
| Accuracy | 100% | |

EXAMPLE 14

In Situ PCR and In Situ RT-PCR of Paraffin-Embedded Lung Sections for Localization of Nucleic Acids of an Epithelial Protein The following protocol as described by Martinez, A., et al. *J. Histochem. and Cytochem.,* Vol. 43, No. 8, pp.739–747, 1995 is used to detect nucleic acids of the epithelial protein, peptide or variants thereof which are associated with pre-cancer and cancer, in precancer and cancer cells. The method is also useful to detect the chromosomal location of the nucleic acid or chromosomal abnormalities at the location as has been reported by Saccone, S. et al *Genomics* 1992, Jan: 12(1): 171–174; Biamonti, G. et al *Nucleic Acid Res.* 1994, Jun 22(11): 1996–2002.

Materials and Methods

Cell Lines

NCH720 and NCH157 cell lines are used in this study. These cell lines were grown under protein-free and hormone-free conditions using phenol red-free RPMI-1640 containing 30 nM selenium and 10 mM L-glutamine (Siegfried et al., *J. Biol. Chem.* 269:8596, 1994). Pellets of approximately $5\times10^6$ cells are washed in PBS, re-suspended in 1 ml of 2% NuSieve low melting-point agarose (Cat. 50082, Lot 626592; FMC BioProducts, Rockland, Me.), allowed to solidify, fixed for 2 hr in 4% paraformaldehyde or 10% formalin, and embedded in paraffin by routine histopathology techniques., Archive Books Ten formalin-fixed, paraffin-embedded blocks containing normal lung and representative cases of precancer and lung tumors are obtained from the files of the BPRB, NCI at the NCI-Navy Medical Oncology Branch.

Immunohistochemistry

The monoclonal antibody 703D4 is used (U.S. Pat. No. 4,569,788). A avidin-biotin histochemical staining procedure (Hsu et al, *J. Histochem. Cytochem.* 29:577, 1981) is used to localize 703D4 immunoreactivity in lung tissue and cell lines using the Vectastrain ABC kit (Cat PK-4001; Vector Laboratories, Burlingame, Calif.) with a 0.03% solution of 3,3'-diaminobenzidine (Cat. D-5637, Lot 122H3642; Sigma, St. Louis, Mo.) and 0.006% $H_2O_2$ as the enzyme substrates.

RNA Extraction

The guanidine isothiocyanate-cesium chloride method of Glisin et al (*Biochemistry* Vol. 13; 2633, 1974) is used to extract total RNA from the cell lines. Poly A +RNA from normal human brain (Cat. 6516-2, Lot 2Y081), liver (Cat. 6510-2, Lot 39076), lung (Cat. 6524-2, Lot 34401), stomach (Cat. 6548-2, Lot 38131), and uterus (Cat. 6537-2, Lot 29100) are purchased from Clontech Laboratories (Palo Alto, Calif.).

Northern Blot

Standard formaldehyde gels were run with total RNA (10 μg/well) at 120 v. 100 mAmp for 3 hr. At the end of the run, the gels are washed for 15 min in 20× SSC and then blotted overnight by capillary flow transfer onto a 0.45-μm nitrocellulose filter (Davis et al, *Basic Methods in Molecular Biology,* Norwalk, Conn., Appleton & Large, 1986). The blots are UV crosslinked at 1200 Joules and pre-hybridized for 4 hr. The Stratagene Prime-It kit (Stratagene; La Jolla, Calif.) is used to label the probe. The probes were prepared by random priming of inserts gel purified from restriction endonuclease digests of plasmids containing full-length cDNAs for hnRNP-A2 and A1 with $^3$P-dCTP. Probe ($1\times10^6$ cpm) is added to each ml of hybridizing buffer. After overnight hybridization, the blot is washed once in 2× SSC/0.1% SDS at room temperature, the blot is washed once in 2× SSC/0.1% at room temperature (RT; 30 min) and once with 0.1% SSC.0.1% SDS at 60° C. (30 min). The blots are then air-dried and autoradiographed at −80° C. on Kodak XAR5 film for 1–2 days.

Standard PCR

Oligonucleotide primers for epithelial protein are made using a MilliGen 8700 DNA synthesizer (Millipore; Marlborough, Mass.). Sequences are 5'-GAGTCCGGTTCGTGTTCGTC-3' (SEQ ID NO.:11) and 5'-TGGCAGCATCAACCTCAGC-3' (SEQ ID NO.:18). All buffers, enzymes, and nucleotides used are obtained from Applied Biosystems (Perkin-Elmer Cetus; Norwald, Conn.). A Perkin-Elmer 9600 Thermocycler is used to amplify the samples. PCR products are analyzed electrophoretically using a 1% agarose gel (80 V, 3 hr) and the ethidium bromide staining is observed under UV light, followed by Southern analysis with nested $^3$P-labeled probes.

Southern Analysis

Gels are denatured in 1.5 M NaCl/0.6 M NaOH and 1.5 M NaCl/2 M Tris and blotted onto a 0.2-μm nitrocellulose filter in 20× SSC by capillary flow transfer overnight. The filter are cross-linked at 80° C. under vacuum and put in hybridization buffer. Anti-sense nested probes are end-labeled by standard $^{32}$P procedures (Sambrook et al, *Molecular Cloning: A Laboratory Manual,* Vol. II, Cold Spring Harbor, N.Y., Cold Spring Harbor Laboratory Press, 8.3, 1989). Hybridization with the probe is done overnight at 42° C. Stringency washing at RT is in 5× SSC/0.1% SDS (twice for 30 min), then 1× SSC/0.1% SDS (twice for 30 min). Filters are air-dried and autoradiographed at −80° C. on Kodak XAR5 film for 2–4 hr.

In Situ PCR

The in situ PCR technique for localizing specific DNA sequences is performed by a three-step protocol as described by Nuovo (PCR in situ hybridization, In Nuovo, GJ, ed. PCR In Situ Hybridization: Protocols and Applications, New York, Raven Press, 157, 1992a). After dewaxing the tissue sections, a protein digestion is carried out to facilitate reagent penetration into the cells. The second step consists of the PCR itself with simultaneous labeling of the PCR products, followed by the third step that visualizes the labeled product. The in situ amplification technique for RNA detection utilizes a similar protocol. However, it incorporates two additional steps. After proteinase digestion the tissue is exposed to RNAse-free DNAse to avoid amplification of genomic DNA. Second, the remaining mRNA is reverse-transcribed to form cDNA templates, which are in turn amplified by PCR. To maximize the efficiency of the in situ PCR technique, all of these protocol steps must be optimized for individual experiments. The reverse transcription and the PCR steps is performed using an OmniSlide thermocycler (20-slide capacity) equipped with a heated wash module (National Labnet; Woodbridge, N.J.).

Protease Digestion

Depending on the fixative and the nature of the tissue, reagent access to the target nucleic acid can vary. To identify optimal permeability methods, we analyzed enzyme digestion procedures, may be varied by the concentration of proteinase K (Cat. P-0390, Lot 93H0603; Sigma) between 1 and 100 μg/ml and incubation time (5–45 min).

DNAse Digestion

Deoxyribonuclease I Amplification Grade (Cat. 18068-015, Lot ED2409; Gibco BRL, Gaithersburg, Md.), 10 U/slide is used to degrade the DNA according to the manufacturer's specifications. The influence of different digestion times on the quality of the staining is tested.

Reverse Transcription

For this step the SuperScript Preamplification System (Cat. 18089-011, Lot EDT001; Gibco is used following the manufacturer's specifications. In summary, the sections are immersed in a solution containing the random primers, covered with parafilm coverslips, and incubated in the thermocycler for 10 min at 70° C. After removing the coverslips, another solution containing the reverse transcriptase (100 U/section) is added and covered with a new piece of parafilm. The slides are then maintained at RT for 10 min, at 45° C. for 45 min, and at 70° C. for 10 min.

PCR

Before the in situ PCR experiment, all parameters for the PCR reaction, including $MgCl_2$ concentration, pH, and annealing temperature, is optimized by standard PCR. At this point the PCR products can be cloned and sequenced to confirm identity. Products are cloned into a pCRII vector (Cat. 2000-01; Invitrogen, San Diego, Calif.) and sequenced with the dsDNA Cycle Sequencing Kit (Cat. 81965A, Lot CAC 108; Gibco). Optimization of conditions favoring single band production is advised because it is not possible to distinguish PCR products of different molecular weights in the tissue sections. To eliminate the possibility of generating PCR products from genomic DNA, it is important to design primers that bridge introns so as to distinguish template source on the basis of product size.

Synchronized "hot start" PCR (Nuovo, The hot start polymerase chain reaction, In Nuovo, GJ, ed. PCR In Situ Hybridization Protocols and Applications, New York, Raven Press, 63, 1992b) is achieved using the Taq neutralizing antibody technique (Kellogg et al, *Bio Techniques* 6:1134, 1994). Taq-blocking monoclonal antibody was purchased from Clontech (TaqStart antibody; Cat. 5400-1, Lot 47656).

For the analyses described here the following PCR mixture is used: 2.5 mM $MgCl_2$ 200 $\mu$M dNTP2, 100 $\mu$M digoxigenin-11-2'-deoxyuridine-5'-triphosphate (Cat. 1558 706, Lot 13945241-12; Boehringer Mannheim, Indianapolis, Ind.), 1 ng/$\mu$l primers, 50 mM KCl, 10 mM Tris-HCL, pH 8.3. An 80-$\mu$l aliquot of solution is applied to each slide, and then each slide is covered by silanated glass coverslips, sealed with rubber cement, and placed in the thermocycler. The targets are amplified, 15–20 cycles to obtain crisp staining. After DNA amplification, two washes in 0.1× SSC at 45° C., 20 min each, are performed to eliminate unbound nucleotides.

Development of Digoxigenin

Detection of digoxigenin-tagged PCR products is done with a kit from Boehringer Mannheim (Cat. 1210 220, Lot. 14101420-13). It involves a 2-hr incubation with an anti-digoxigenin antibody bound to alkaline phosphatase. After a thorough rinse, the appropriate substrates (nitroblue tetrazolium and 5-bromo-chloro-3-indolyl-phosphate) are enzymatically transformed into a dark blue precipitate. Color deposition was checked under the microscope.

Recently, it has been observed that polyvinyl alcohol enhances the intensity of the alkaline phosphatase-nitroblue tetrazolium reaction and prevents diffusion of the precipitate (Barth and Ivarie, *Bio Techniques* 17:324, 1994; De Block and Debrouwer, *Anal. Biochem.* 215:86, 1993). To take advantage of this technique the dilution of the anti-digoxigenin antibody is increased to 1:2000 (instead of the usual 1:500 recommended by the manufacturer) to obtain considerable background reduction.

Controls

The PCR technique is well known for its ability to amplify even single copies of DNA in a sample, contaminants included. Therefore, the precautions recommended for routine PCR regarding scrupulous care with cleanliness, use of a dedicated set of pipettes, and preparation of the PCR mixture away from the amplification area (Orrego, Organizing a laboratory for PCR work. In Innis M A, Gelfand D H, Sninsky J J, White, T J, eds. PCR protocols: A Guide to Methods and Applications, New York, Academic Press, 447, 1990) are also applicable for in situ PCR. In addition, working with tissue sections adds new concerns, such as heterogeneous application of reagents, bubbles, drying of the boundaries, and stability of the nucleic acids during the preparation of the samples.

At least three types of controls are recommended in every experiment to avoid false-positives or -negatives.

Positive Control

Include a section from a block that is previously positive for the same set of primers. If this is the first time that these primers are being used, include a section of a well-fixed tissue or cell line known to have a high expression of the target nucleic acid as determined by other techniques (e.g., Northern analysis, standard PCR, in situ hybridization).

Negative Control

Omission of the reverse transcription and/or RNAse treatment will yield information about nonspecific amplification of remaining nuclear or mitochondrial DNA.

Negative Control

Omission of the primers in the PCR mixture will reveal nonspecific staining due to endogenous priming: DNA fragments produced by the exonuclease activity of the DNA polymerase (Komminoth and Long, *Virchows Arch* [B] 64:67, 1993) or by apoptosis (Gold et al, *J. Histo Chem. Cytochem* 41: 1023) and other artifacts such as intrinsic alkaline phosphatase activity.

An additional control consists of establishing existing relationship between the transcriptional/translational products. This can be done by staining one section for the nucleic acid by in situ PCR and a serial section with a specific antibody against the polypeptide. The co-localization of the mRNA and its protein within the same cells will strengthen the validity of the observation.

Confirmation of the in situ PCR product integrity can be achieved in two ways: (a) It is possible to scrape the tissue of the glass slide after in situ PCR, to extract the DNA (TRIzol reagent, Cat. 5596UA, Lot DPU 201; Gibco), and to analyze by agarose gel electrophoresis and Southern blot with the appropriate radioactive probe. Cloning and sequencing of this product is also possible, after several additional PCR cycles to yield products without modified bases, (b) Product identity is tested by performing in situ hybridization with a $^{32}$P-labeled nested probe after the amplification. This procedure is routinely used for indirect in situ PCR (Patterson et al *Science* 260:976, 1994; Walter et al *Ann NY Acad. Sci.* 724:404, 1994).

EXAMPLE 15

Strategies to identify significant post translational modifications of hnRNP A2/B1 can be performed in at least two ways. The previously described cyanogen bromide digest fragments are systematically evaluated for specific sites of post translational activity. Using a panel of specialized enzymes that attack a protein at the site of a specific post translational modificatons, the presence of a particular modification is revealed in comparing an enzymatically treated cyanogen bromide-treated digest fragment with a sample of the original cyanogen bromide-treated material (that is not subjected to the enzyme). For example, treatment of digests with phosphatases would reveal change in molecular weight after treatment with the enzyme by either 2D-gel electrophoresis or by mass spectrometry. These are standard approaches to the characterization of post translational changes.

EXAMPLE 16

Heterogeneous Nuclear Ribonucleoprotein (HnRNP) A2/B1 Expression in Fetal Lung The expression of hnRNP A2/B1 by immunocytochemistry and in situ hybridization in fetal tissue was evaluated to determine if these molecules were potentially involved in early organogenesis. This would establish hnRNP A2/B1 as an oncofetal antigen and provide additional support for the hypothesis that hnRNP A2/B1 is playing a central role in the process of carcinogenesis and fetal development. The tissues evaluated included multiple sections of mouse and rat lung tissue from various stages of embryonal development and examples of mature rodent lung. Comparable human tissue was also evaluated.

Sections (4 $\mu$m thick) were mounted on slides coated with Vectabond (SP-1800; Vector Laboratories, Burlingame, Calif.), dewaxed and prepared for hybridization with RNA probes as described by Gibson and Polak. Plasmid 72 ORNPc1A containing the human hnRNP gene was used to generate riboprobes. In summary, the DNA fragment was subcloned into pCR II vector (Invitrogen) and linearized with the appropriate restriction enzymes. Labeled probes were prepared using digoxigenin-11-UTP (1277 073; Boehringer, Barcelona, Spain) and T7 (881 767; Boehringer) or T3 RNA polymerases (1031 163; Boehringer) to synthesize sense and antisense RNA transcripts, respectively. Hybridization was performed in a moist chamber at 46° C. for 20 hours in a 15-$\mu$l volume containing 0.5 ng/$\mu$l of probe for each section. Stringency washes included treatments with 150 mmol/L NaCl, 15 mmol/L sodium citrate, pH 7.0 (SSC), and sodium dodecyl sulfate (SDS) as follows: four washes in 2× SSC/0/1% SDS, two washes in 0.1× SSC/0.1% SDS at 46° C., brief rinses in 2× SSC, incubation in 2× SSC containing 10 $\mu$g/ml RNAse at 37° C. for 15 minutes, and additional rinses in 2× SSC.

Visualization of digoxigenin was performed with a monoclonal =antibody coupled to alkaline phosphatase (1093 274; Boehringer) diluted 1:500 acting for 2 hours at room temperature. Nitroblue tetrazolium chloride (N-5514; Sigma) and 5-bromo-4-chloro-3-indoly-phosphate (B-8503; Sigma) were used as substrates for the alkaline phosphatase. Controls included the use of the sense probe and treatment of the sections with RNAse before the hybridization.

The results of this analysis are as follows. The hnRNP A2/B1 expression in the lung begins with the mesenchymal cells of the mainstream bronchus on day 10 of embryonal development. The immunoreactivity migrates from the mainstream to the evolving bronchi through Day 13 and 14 with strong expression in the undifferentiated epithelium. FIGS. 17*a*–17*d* show the dynamic changes in fetal mouse lung. The central expression of the antigen is restricted and the activity becomes positive in the undifferentiated epithelium of the peripheral airways by Day 16. So the pattern of expression of hnRNP A2/B1 mirrors the known sequence of lung development in moving from central to distal in a timeframe that precisely corresponds to peak organ development activity. This pattern of timing and expression was consistent between mice, rats and human. In all three, the expression of this marker in normal, mature lung was markedly restricted. The pattern and intensity of expression at the protein and mRNA level was also parallel.

This temporal and spatial correlation of hnRNP A2/B1 expression is highly suggestive of a critical role for this molecule in growth regulation both in fetal development and is consistent with our hypothesis that hnRNP A2/B1 is playing an important role in the development of cancer.

An additional finding of this work was the expression of hnRNP A2/B1 in other sites. The earliest expression was in the mesenchyma especially of the heart. Discreet expression was evident in brain and ganglions of the spinal cord. There was broad representation of this antigen in other epithelial sites that modulated during the course of development. This results suggests that hnRNP A2/B1 may have diagnostic value for other types of cancer.

REFERENCES

1. Boring, C., Squires, T., Tong, T. and Montgomery, S. Cancer statistics. Ca-A Cancer J. for Clinicians, 44: 7–26, 1994.
2. Saccomanno, G., Saunders, R. and Klein, M. Cytology of the lung in reference to irritant, individual sensitivity and healing. Acta Cytol, 14: 377–381, 1970.
3. Frost, J., Fontana, R. and Melamed, M. Early lung cancer detection: Summary and conclusions. Am. Res. Respir. Dis., 103: 565–570, 1984.
4. Tockman, M., Gupta, P., Myers, J., Frost, J. Baylin, S., Gold, E., Chase, A., Wilkinson, P. and Mulshine, J. Sensitive and specific monoclonal antibody recognition of human lung cancer antigen on preserved sputum cell: A new approach to early lung cancer detection. J. Clin. Oncol., 6: 1685–1693, 1988.
5. Mulshine, J., Cuttitta, F., Bibro, M., Fedorko, J., Fargion, S., Little, C., Carney, D., Gazdar, A. and Minna, J. Monoclonal antibodies that distinguish non-small cell from small cell lung cancer. J. Immuol., 131: 497–502, 1983.
6. Saccomanno, G., Archer, V. and Auerbach, O. Development of carcinoma of the lung as reflected in exfoliated cells. Cancer, 33: 1974.
7. Naisell, M., Auer, G. and Kato, H. Cytological studies in man and animals on development of bronchogenic carcinoma. In: E. McDowell (eds.), Cytological studies in man and animals on development of bronchogenic carcinoma., pp. 207–242, New York: Churchill Livingstone, 1987.
8. Slaughter, D., Southwick, H. and Smejkal, W. "Field cancerization" in oral stratified squamous epithelium. Cancer, 6: 963–968, 1953.
9. Auerbach, O., Stout A., Hammond, C. and Garfinkel, M. Changes in bronchial epithelium in relation to cigarette smoking and in relation to lung cancer. The New England Journal of Medicine, 265: 253–267, 1961.
10. World Health Organization. The World Health Organization histological typing of lung tumors. American Journal of Clinical Pathology, 77: 123–136, 1982.
11. Linnoila, R., Mulshine, J., Steinberg, S., Funa, K., Matthews, M., Cotelingam, J. and Gazdar, A. Neuroendocrine differentiation in endocrine and nonendocrine lung carcinoma. Am. J. Clin. Pathol., 90: 1–12, 1988.
12. di Fiore, M. Atlas of human histology. (ed), Philadelphia: Lea & Febiger, 1981.
13. Plopper, C. G. and Dungworth, D. Structure, function, cell injury and cell renewal of bronchiolar and alveolar epithelium. In: E. McDowell (eds.), Structure, function, cell injury and cell renewal of bronchiolar and alveolar epithelium, pp. 94–128, New York: Churchill Livingstone, 1987.
14. Nasiell, M. The general appearance of the bronchial epithelium in bronchial carcinoma. Acta Cytol, 7: 97–106, 1963.
15. Jensen, S., Steinberg, S. Jones, J. and Linnoila, R. Clara cell & W 10 KD protein mRNA in normal and atypical regions of human respiratory epithelium. Int. J. Cancer, 58: 629–637, 1994.
16. Sozzi, G., Miozzo, M., Tagliabue, E. and et al. Cytogenetic abnormalities and overexpression of receptors for growth factor in normal bronchial epithelium and tumor samples of lung cancer patients. Cancer Res., 51: 400–404, 1991.
17. Melamend, M., and Zaman, M. Pathogenesis of epidermoid carcinoma of lung. In: Y. Shimosato, M. Melamed and P. Nettesheim (eds.) Pathogenesis of epidermoid carcinoma of lung, pp. 37–64 Boca Raton, Fla.: CRC Press, 1982.
18. Hittelman, W. Wang, Z., Cheong, N., Sohn, H. and Lee, J. Premature chromosome condensation and cytogenetics of human solid tumor. Cancer Bull, 41: 298–305, 1989.
19. Carter, D., Marsch, R. and Baker, R. Relationship of morphology of clinical presentation in ten cases of early squamous carcinoma of the lung. Cancer, 37: 1389–1396, 1976.
20. Nettesheim, P. and Szakal, M. Morphogenesis of alveolar bronchiolization. Lab. Invest., 26: 210–219, 1972.
21. Tockman, M., Erozan, Y., Gupta, P., Piantadosi, S., Mulshine, J., Ruckdeschel, J. and Investigators, t. L. The early detection of second primary lung cancers by sputum immunostaining. Chest, 106: 385S–390S, 1994.
22. Shaw, G., Gazdar, A., Phelps. R., Linnoila, R., Ihde, D., Johnson, B., Oie, H., Pass, H., Steinberg, S., Ghosh, B., Walsh, T., Nesbitt, J., Cotelingam, J., Minna, J. and Mulshine, J. Individualized chemotherapy for patients with non-small cell lung cancer determined by prospective identification of neuroendocrine markers and in vitro drug sensitivity testing. Cancer Research, 53:5181–5187, 1993.
23. World Health Organization. The World Health Organization histological typing of lung tumors. American Journal of Clinical Pathology, 77:123–136, 1982.
24. Gazdar, A., carney, D., Guccion, J. and Baylin, S. Small cell carcinoma of the lung: cellular organ and relationship to other pulmonary tumors. In: F. Greco, R. Oldman and J. Bunn PA (eds.), Small cell carcinoma of the lung.

25. Grover F. L., Piantadosi S. Recurrence and survival following resection of bronchioloalveolar carcinoma of the lung—the Lung Cancer Study Group experience Ann Surg 1989; 209:779–90.

26. Qiao Y. L., Taylor P. R., Yao S. X., et al. The relation of radon exposure and tobacco use to lung cancer among miners in Yunnan Province, China. Am. J. Ind. Med. 1989; 16:511–521.

27. Piantadosi S. Long term follow-up of surgically resected T1N0 non-small cell lung cancer patients. Lung Cancer 1988; 4 (Suppl):A82. abstract.

28. Feld R., Rubinstein L. V., Weisenberg T. H., et al. Sites of recurrence in resected stage I non-small cell lung cancer: a guide for future studies. J. Clin. Oncol. 1984; 2:1352–8.

29. Ginsberg R. J. Limited resection for peripheral T1N0 tumors. Lung Cancer 1988; 4 (Suppl):A80. abstract.

30. Thomas P., Feld R. Preliminary report of a clinical trial comparing post-resection adjuvant chemotherapy versus no therapy for T1N1, T2N0 non-small cell lung cancer. Lung Cancer 1988:A160. abstract.

31. Mountain C. F. A new international staging system for lung cancer. Chest 1986; 89 (Suppl):225S–233S.

32. Kreyberg L. Histological typing of lung tumors. Vol. 1. International histological classification of tumors. Geneva: WHO, 1967.

33. Gupta P. K., Myers J. D., Baylin S. B., Mulshine J. L., Cuttitta F., Gazdar A. F. Improved antigen detection in ethanol-fixed cytologic specimens. A modified avidin-biotin-peroxidase complex (ABC) method. Diagn Cytopathol 1985; 1:133–6.

34. Tockman M. S., Gupta P. K., Pressman N. J., Mulshine J. L. Considerations in bringing a cancer biomarker to clinical application. Cancer Res. 1992; 52 (Suppl) :2711S–8S.

35. Tockman M. S., Gupta P. K., Pressman N. J., Mulshine J. L. Cytometric validation of immunocytochemical observations in developing lung cancer. Diagnostic Cytopathol 1993; 9(6):615–22.

We claim:

1. A method for computer-assisted detection of a cell expressing hnRNP A2/B1 mRNA using dual wavelength image densitometry comprising:

(a) contacting a cell with a labeled probe which specifically hybridizes with hnRNP A2/B1 mRNA in the cell;

(b) illuminating the cell to acquire a first background-subtracted, shading-corrected image of the cell at a first predetermined wavelength;

(c) illuminating the cell to acquire a second background-subtracted, shading-corrected image of the cell at a second predetermined wavelength; and (d) using a computer to compare the first and second background-subtracted, shading-corrected images with a set of control images to detect the level of hnRNP A2/B1 mRNA expression by the cell, wherein the labeled probe is detected from either of the first or second images.

2. A method for determining a human lung cancer or precancer cell comprising:

(a) contacting a sample lung cell with a labeled probe which specifically hybridizes with hnRNP A2/B1 mRNA in the sample lung cell;

(b) generating an optical image from the sample lung cell;

(c) acquiring the optical image;

(d) analyzing the optical image for a cellular parameter or combination of cellular parameters unique to a lung cancer or precancer cell; and (e) determining whether the sample lung cell is a lung cancer or precancer cell using a discriminant function, the discriminant function being created by comparing the cellular parameter or combination of cellular parameters from the optical images of normal lung control cells and lung cancer or precancer control cells, wherein at least one cellular parameter is hnRNP A2/B1 mRNA expression.

3. A method for determining a human breast cancer or precancer cell comprising:

(a) contacting a sample breast cell with a labeled probe which specifically hybridizes with hnRNP A2/B1 mRNA in the sample breast cell;

(b) generating an optical image from the sample breast cell;

(c) acquiring the optical image;

(d) analyzing the optical image for a cellular parameter or combination of cellular parameters unique to a breast cancer or precancer cell; and (e) determining whether the sample breast cell is a breast cancer or precancer cell using a discriminant function, the discriminant function being created by comparing the cellular parameter or combination of cellular parameters from the optical images of normal breast control cells and breast cancer or precancer control cells, wherein at least one cellular parameter is hnRNP A2/B1 mRNA expression.

4. A method for determining a human epithelial cancer or precancer cell comprising:

(a) contacting a sample epithelial cell with a labeled probe which specifically hybridizes with hnRNP A2/B1 mRNA in the sample epithelial cell;

(b) generating an optical image from the sample epithelial cell;

(c) acquiring the optical image;

(d) analyzing the optical image for a cellular parameter or combination of cellular parameters unique to an epithelial cancer or precancer cell; and (e) determining whether the sample epithelial cell is an epithelial cancer or precancer cell using a discriminant function, the discriminant function being created by comparing the cellular parameter or combination of cellular parameters from the optical images of normal epithelial control cells and epithelial cancer or precancer control cells, wherein at least one cellular parameter is hnRNP A2/B1 mRNA expression.

5. The method according to any of claims 2, 3 or 4 wherein the labeled probe is added in situ.

6. The method according to any of claims 2, 3 or 4 wherein the optical image of the biological sample is stored in a digital image processor.

7. The method according to any of claims 2, 3 or 4 wherein the combination of cellular parameters unique to the cancer cell further comprises a cellular parameter selected from the group consisting of nuclear texture difference moment, nuclear elliptical area at a Fourier harmonic, optical density, cellular morphometry and combinations thereof.

8. The method according to any of claims 2, 3 or 4 wherein the combination of cellular parameters analyzed includes an optical density and cellular morphometry.

9. The method according to any of claims 2, 3 or 4 wherein the combination of cellular parameters analyzed includes a nuclear texture difference moment.

10. The method according to any of claims 2, 3 or 4 wherein the combination of cellular parameters analyzed includes a nuclear elliptical area at a high Fourier harmonic.

11. The method according to any of claims 2, 3 or 4 wherein the combination of cellular parameters analyzed includes an optical density, the optical density being analyzed at two different wavelengths.

12. The method according to any of claims 2, 3 or 4 wherein the combination of cellular parameters analyzed is an optical density at 600 nm, an optical density at 510 nm, a nuclear texture difference moment and a nuclear elliptical area at a high Fourier harmonic.

13. The method according to any of claims 2, 3 or 4 wherein the discriminant function is further created from a nuclear texture difference moment and a nuclear elliptical area at a Fourier harmonic from the images of the normal control cells treated with the labeled probe and from the images of the cancer or precancer control cells treated with the labeled probe.

14. The method according to claim 13 wherein the discriminant function is represented by the formula:

$$D=\beta_0+\beta_1(\text{Optical Density}_{600})+\beta_2(\text{Optical Density}_{510})+\beta_3(\text{Nuclear Texture Differences})+\beta_3(\text{Nuclear Ellipse Area at a Fourier Harmonic}),$$

wherein $\beta_0$, $\beta_1$, $\beta_2$ and $\beta_3$ are calibrated optical density measurements.

15. The method according to claim 14 wherein the Fourier harmonic is in a range of about 7 to about 9.

16. The method according to claim 14 wherein the Fourier harmonic is about 9.

17. The method according to any of claims 2, 3 or 4 wherein the method provides greater than about 80% accuracy in predicting the development of cancer in an individual.

18. The method according to any of claims 2, 3 or 4 wherein a value of about zero or less for the discriminant function is indicative of cancer or precancer.

19. The method according to any of claims 2, 3 or 4 wherein the normal control cells and the cancer control cells are derived from an archived bank of cells taken from normal humans and humans with cancer or precancer, respectively.

20. A method for diagnosing a lung, breast or epithelial cancer or precancer in a human comprising:

(a) adding to a biological sample a labeled probe which specifically hybridizes with hnRNP A1/B2 mRNA, the biological sample comprising lung, breast or epithelial cells or tissue suspected of being cancerous or precancerous, or an extract thereof;

(b) obtaining an optical image of the biological sample containing the labeled probe;

(c) detecting an optical density of the image of the biological sample; and (d) using the optical density of the image of the biological sample and a discriminant function to predict cancer or precancer, the discriminant function being created from optical density measurements of images of a normal lung, breast or epithelial control cell, tissue or extract treated with the labeled probe and a lung, breast or epithelial cancer or precancer control cell, tissue or extract treated with the labeled probe and being created by comparing a cellular parameter or combination of cellular parameters from the optical densities of the normal lung, breast or epithelial control cell, tissue or extract and the lung, breast or epithelial cells or tissue suspected of being cancerous or precancerous or an extract thereof, wherein at least one cellular parameter is the level of hnRNP mRNA expression.

21. The method according to claim 20 wherein the labeled probe is added in situ.

22. The method according to claim 20 wherein the image of the biological sample is stored in a digital image processor.

23. The method according to claim 20 wherein the combination of cellular parameters unique to the cancer cell, tissue or extract thereof further comprises a cellular parameter selected from the group consisting of nuclear texture difference moment, nuclear elliptical area at a Fourier harmonic, optical density, cellular morphometry and combinations thereof.

24. The method according to claim 20 wherein the combination of cellular parameters analyzed includes an optical density and cellular morphometry.

25. The method according to claim 20 wherein the combination of cellular parameters analyzed includes a nuclear texture difference moment.

26. The method according to claim 20 wherein the combination of cellular parameters analyzed includes a nuclear elliptical area at a high Fourier harmonic.

27. The method according to claim 20 wherein the combination of cellular parameters analyzed includes an optical density, the optical density being analyzed at two different wavelengths.

28. The method according to claim 20 wherein the combination of cellular parameters analyzed is an optical density at 600 nm, an optical density at 510 nm, a nuclear texture difference moment and a nuclear elliptical area at a high Fourier harmonic.

29. The method according to claim 20 wherein the discriminant function is further created from a nuclear texture difference moment and a nuclear elliptical area at a Fourier harmonic from the images of the normal control cell, tissue or extract treated with the labeled probe and from the images of the cancer or precancer control cell, tissue or extract treated with the labeled probe.

30. The method according to claim 29 wherein the discriminant function is represented by the formula:

$$D=\beta_0+\beta_1(\text{Optical Density}_{600})+\beta_2(\text{Optical Density}_{510})+\beta_3(\text{Nuclear Texture Differences})+\beta_3(\text{Nuclear Ellipse Area at a Fourier Harmonic}),$$

wherein $\beta_0$, $\beta_1$, $\beta_2$ and $\beta_3$ are calibrated optical density measurements.

31. The method according to claim 30 wherein the Fourier harmonic is in a range of about 7 to about 9.

32. The method according to claim 30 wherein the Fourier harmonic is about 9.

33. The method according to claim 20 wherein the method provides greater than about 80% accuracy in predicting the development of cancer in an individual.

34. The method according to claim 20 wherein a value of about zero or less for the discriminant function is indicative of cancer or precancer.

35. The method according to claim 20 wherein the normal control cells and the cancer control cells are derived from an archived bank of cells taken from normal humans and humans with cancer or precancer, respectively.

* * * * *

SEQUENCE LISTING

```
(1) GENERAL INFORMATION:

   (iii) NUMBER OF SEQUENCES:  23


(2) INFORMATION FOR SEQ ID NO: 1:

     (i) SEQUENCE CHARACTERISTICS:
          (A) LENGTH:  12
          (B) TYPE:  Amino Acid
          (C) STRANDEDNESS:  Unknown
          (D) TOPOLOGY:  Linear

    (ii) MOLECULE TYPE: peptide

    (xi) SEQUENCE DESCRIPTION: SEQ ID NO: 1:

Ala Ala Arg Pro His Ser Ile Asp Gly Arg Val Val
  1               5                  10


(2) INFORMATION FOR SEQ ID NO: 2:

     (i) SEQUENCE CHARACTERISTICS:
          (A) LENGTH:  12
          (B) TYPE:  Amino Acid
          (C) STRANDEDNESS:  Unknown
          (D) TOPOLOGY:  Linear

    (ii) MOLECULE TYPE: peptide

    (xi) SEQUENCE DESCRIPTION: SEQ ID NO: 2:

Gln Glu Val Gln Ser Ser Arg Ser Gly Arg Gly Gly
  1               5                  10


(2) INFORMATION FOR SEQ ID NO: 3:

     (i) SEQUENCE CHARACTERISTICS:
          (A) LENGTH:  11
          (B) TYPE:  Amino Acid
          (C) STRANDEDNESS:  Unknown
          (D) TOPOLOGY:  Linear

    (ii) MOLECULE TYPE: peptide

    (xi) SEQUENCE DESCRIPTION: SEQ ID NO: 3:

Arg Glu Lys Glu Gln Phe Arg Lys Leu Phe Ile
  1               5                  10
```

(2) INFORMATION FOR SEQ ID NO: 4:

(i) SEQUENCE CHARACTERISTICS:
(A) LENGTH: 15
(B) TYPE: Amino Acid
(C) STRANDEDNESS: Unknown
(D) TOPOLOGY: Linear (ii) MOLECULE TYPE: peptide (xi) SEQUENCE DESCRIPTION: SEQ ID NO: 4:

```
Glu Lys Thr Lys Glu Thr Val Pro Leu Glu Arg Lys
  1               5                  10

Lys Arg Glu
         15
```

(2) INFORMATION FOR SEQ ID NO: 5:

(i) SEQUENCE CHARACTERISTICS:
(A) LENGTH: 10
(B) TYPE: Amino Acid
(C) STRANDEDNESS: Unknown
(D) TOPOLOGY: Linear (ii) MOLECULE TYPE: peptide (xi) SEQUENCE DESCRIPTION: SEQ ID NO: 5:

```
Ala Ala Arg Pro Ser Asp Gly Arg Val Val
  1               5                  10
```

(2) INFORMATION FOR SEQ ID NO: 6:

(i) SEQUENCE CHARACTERISTICS:
(A) LENGTH: 12
(B) TYPE: Amino Acid
(C) STRANDEDNESS: Unknown
(D) TOPOLOGY: Linear (ii) MOLECULE TYPE: peptide (xi) SEQUENCE DESCRIPTION: SEQ ID NO: 6:

```
Glu Arg Glu Lys Glu Gln Phe Arg Lys Leu Phe Ile
  1               5                  10
```

(2) INFORMATION FOR SEQ ID NO: 7:

(i) SEQUENCE CHARACTERISTICS:
(A) LENGTH: 353
(B) TYPE: Amino Acid
(C) STRANDEDNESS: Unknown
(D) TOPOLOGY: Linear (ii) MOLECULE TYPE: peptide (xi) SEQUENCE DESCRIPTION: SEQ ID NO: 7:

```
Met Glu Lys Thr Leu Glu Thr Val Pro Leu Glu Arg
  1               5                  10

Lys Lys Arg Glu Lys Glu Gln Phe Arg Lys Leu Phe
         15                  20

Ile Gly Gly Leu Ser Phe Glu Thr Thr Glu Glu Ser
 25                  30                  35

Leu Arg Asn Tyr Tyr Glu Gln Trp Gly Lys Leu Thr
             40                  45

Asp Cys Val Val Met Arg Asp Pro Ala Ser Lys Arg
     50                  55                  60
```

-continued

```
Ser Arg Gly Phe Gly Phe Val Thr Phe Ser Ser Met
                 65                  70

Ala Glu Val Asp Ala Ala Met Ala Ala Arg Pro His
        75                  80

Ser Ile Asp Gly Arg Val Val Glu Pro Lys Arg Ala
 85                  90                  95

Val Ala Arg Glu Glu Ser Gly Lys Pro Gly Ala His
            100                 105

Val Thr Val Lys Lys Leu Phe Val Gly Gly Ile Lys
    110                 115                 120

Glu Asp Thr Glu Glu His His Leu Arg Asp Tyr Phe
                125                 130

Glu Glu Tyr Gly Lys Ile Asp Thr Ile Glu Ile Ile
        135                 140

Thr Asp Arg Gln Ser Gly Lys Lys Arg Gly Phe Gly
145                 150                 155

Phe Val Thr Phe Asp Asp His Asp Pro Val Asp Lys
            160                 165

Ile Val Leu Gln Lys Tyr His Thr Ile Asn Gly His
    170                 175                 180

Asn Ala Glu Val Arg Lys Ala Leu Ser Arg Gln Glu
                185                 190

Met Gln Glu Val Gln Ser Ser Arg Ser Gly Arg Gly
        195                 200

Gly Asn Phe Gly Phe Gly Asp Ser Arg Gly Gly Gly
205                 210                 215

Gly Asn Phe Gly Pro Gly Pro Gly Ser Asn Phe Arg
            220                 225

Gly Gly Ser Asp Gly Tyr Gly Ser Gly Arg Gly Phe
    230                 235                 240

Gly Asp Gly Tyr Asn Gly Tyr Gly Gly Gly Pro Gly
                245                 250

Gly Gly Asn Phe Gly Gly Ser Pro Gly Tyr Gly Gly
        255                 260

Gly Arg Gly Gly Tyr Gly Gly Gly Gly Pro Gly Tyr
265                 270                 275

Gly Asn Gln Gly Gly Gly Tyr Gly Gly Gly Tyr Asp
            280                 285

Asn Tyr Gly Gly Gly Asn Tyr Gly Ser Gly Asn Tyr
    290                 295                 300

Asn Asp Phe Gly Asn Tyr Asn Gln Gln Pro Ser Asn
                305                 310

Tyr Gly Pro Met Lys Ser Gly Asn Phe Gly Gly Ser
        315                 320

Arg Asn Met Gly Gly Pro Tyr Gly Gly Gly Asn Tyr
325                 330                 335

Gly Pro Gly Gly Ser Gly Gly Ser Gly Gly Tyr Gly
            340                 345

Gly Arg Ser Arg Tyr
    350
```

(2) INFORMATION FOR SEQ ID NO: 8:

-continued (i) SEQUENCE CHARACTERISTICS:
(A) LENGTH: 341
(B) TYPE: Amino Acid
(C) STRANDEDNESS: Unknown
(D) TOPOLOGY: Linear (ii) MOLECULE TYPE: peptide (xi) SEQUENCE DESCRIPTION: SEQ ID NO: 8:

```
Met Glu Arg Glu Lys Glu Gln Phe Arg Lys Leu Phe
  1             5                  10

Ile Gly Gly Leu Ser Phe Glu Thr Thr Glu Glu Ser
        15                  20

Leu Arg Asn Tyr Tyr Glu Gln Trp Gly Lys Leu Thr
 25                 30                  35

Asp Cys Val Val Met Arg Asp Pro Ala Ser Lys Arg
            40                  45

Ser Arg Gly Phe Gly Phe Val Thr Phe Ser Ser Met
     50                 55                  60

Ala Glu Val Asp Ala Ala Met Ala Ala Arg Pro His
                65                  70

Ser Ile Asp Gly Arg Val Val Glu Pro Lys Arg Ala
        75                  80

Val Ala Arg Glu Glu Ser Gly Lys Pro Gly Ala His
 85                 90                  95

Val Thr Val Lys Lys Leu Phe Val Gly Gly Ile Lys
            100                 105

Glu Asp Thr Glu Glu His His Leu Arg Asp Tyr Phe
    110                 115                 120

Glu Glu Tyr Gly Lys Ile Asp Thr Ile Glu Ile Ile
                125                 130

Thr Asp Arg Gln Ser Gly Lys Lys Arg Gly Phe Gly
        135                 140

Phe Val Thr Phe Asp Asp His Asp Pro Val Asp Lys
145                 150                 155

Ile Val Leu Gln Lys Tyr His Thr Ile Asn Gly His
            160                 165

Asn Ala Glu Val Arg Lys Ala Leu Ser Arg Gln Glu
    170                 175                 180

Met Gln Glu Val Gln Ser Ser Arg Ser Gly Arg Gly
                185                 190

Gly Asn Phe Gly Phe Gly Asp Ser Arg Gly Gly Gly
        195                 200

Gly Asn Phe Gly Pro Gly Pro Gly Ser Asn Phe Arg
205                 210                 215

Gly Gly Ser Asp Gly Tyr Gly Ser Gly Arg Gly Phe
            220                 225

Gly Asp Gly Tyr Asn Gly Tyr Gly Gly Gly Pro Gly
    230                 235                 240

Gly Gly Asn Phe Gly Gly Ser Pro Gly Tyr Gly Gly
                245                 250

Gly Arg Gly Gly Tyr Gly Gly Gly Gly Pro Gly Tyr
        255                 260

Gly Asn Gln Gly Gly Gly Tyr Gly Gly Gly Tyr Asp
265                 270                 275
```

-continued

Asn Tyr Gly Gly Gly Asn Tyr Gly Ser Gly Asn Tyr
280 285

Asn Asp Phe Gly Asn Tyr Asn Gln Gln Pro Ser Asn
290 295 300

Tyr Gly Pro Met Lys Ser Gly Asn Phe Gly Gly Ser
305 310

Arg Asn Met Gly Gly Pro Tyr Gly Gly Gly Asn Tyr
315 320

Gly Pro Gly Gly Ser Gly Gly Ser Gly Gly Tyr Gly
325 330 335

Gly Arg Ser Arg Tyr
340

(2) INFORMATION FOR SEQ ID NO:9:

(i) SEQUENCE CHARACTERISTICS:
(A) LENGTH: 769 base pairs
(B) TYPE: nucleic acid
(C) STRANDEDNESS: unknown
(D) TOPOLOGY: linear (ii) MOLECULE TYPE: cDNA (xi) SEQUENCE DESCRIPTION: SEQ ID NO:9:

ATGTCTAAGT CAGAGTCTCC TAAAGAGCCC GAACAGCTGA GGAAGCTCTT 50

CATTGGAGGG TTGAGCTTTG AAACAACTGA TGAGAGCCTG AGGAGCCATT 100

TTGAGCAATG GGGAACGCTC ACGGACTGTG TGGTAATGAG AGATCCAAAC 150

ACCAAGCGCT CTAGGGGCTT TGGGTTTGTC ACATATGCCA CTGTGGAGGA 200

GGTGGATGCA GCTATGAATG CAAGGCCACA CAAGGTGGAT GGAAGAGTTG 250

TGGAACCAAA GAGAGCTGTC TCCAGAGAAG ATTCTCAAAG ACCAGGTGCC 300

CACTTAACTG TGAAAAAGAT ATTTGTTGGT GGCATTAAAG AAGACACTGA 350

AGAACATCAC CTAAGAGATT ATTTTGAACA GTTTGGAAAA ATTGAAGTGA 400

TTGAAATCAT GACTGACCGA GGCAGTGGCA AGAAAAAGGG CTTTGCCTTT 450

GTAACCTTTG ACGACCATGA CTCCGTGGAT AAGATTGTCA TTCAGAAATA 500

CCATACTGTG AATGGCCACA ACTGTGAAGT TAGAAAAGCC CTGTCAAAGC 550

AAGAGATGGC TAGTGCTTCA TCCAGCCAAA GAGGTCGAAG TGGTTCTGGA 600

AACTTTGGTG GTGGTCGTGG AGGTGGTTTC GGTGGGAATG ACAACTTCGG 650

TCGTGGAGGA AACTTCAGTG GTCGTGGTGG CTTTGGTGGC AGCCGTGGTG 700

GTGGTGGATA TGGTGGCAGT GGGGATGGCT ATAATGGATT TGGCAATGAT 750

GGAAGCAATT TTGGAGGTG 769

(2) INFORMATION FOR SEQ ID NO:10:

(i) SEQUENCE CHARACTERISTICS:
(A) LENGTH: 764 base pairs
(B) TYPE: nucleic acid
(C) STRANDEDNESS: unknown
(D) TOPOLOGY: linear (ii) MOLECULE TYPE: cDNA (xi) SEQUENCE DESCRIPTION: SEQ ID NO:10:

ATGGAGAGAG AAAAGGAACA GTTCCGTAAG CTCTTTATTG GTGGCTTAAG 50

CTTTGAAACC ACAGAAGAAA GTTTGAGGAA CTACTACGAA CAATGGGGAA 100

-continued

```
AGCTTACAGA CTGTGTGGTA ATGAGGGATC CTGCAAGCAA AAGATCAAGA                150

GGATTTGGTT TTGTAACTTT TTCATCCATG GCTGAGGTTG ATGCTGCCAT                200

GGCTGCAAGA CCTCATTCAA TTGATGGGAG AGTAGTTGAG CCAAAACGTG                250

CTGTAGCAAG AGAGGAATCT GGAAAACCAG GGCTCATGT AACTGTGAAG                 300

AAGCTGTTTG TTGGCGGAAT TAAAGAAGAT ACTGAGGAAC ATCACCTTAG                350

AGATTACTTT GAGGAATATG GAAAAATTGA TACCATTGAG ATAATTACTG                400

ATAGGCAGTC TGGAAAGAAA AGAGGCTTTG GCTTTGTTAC TTTTGATGAC                450

CATGATCCTG TGGATAAAAT CGTATTGCAG AAATACCATA CCATCAATGG                500

TCATAATGCA GAAGTAAGAA AGGCTTTGTC TAGACAAGAA ATGCAGGAAG                550

TTCAGAGTTC TAGGAGTGGA AGAGGAGGCA ACTTTGGCTT TGGGGATTCA                600

CGTGGTGGCG GTGGAAATTT CGGACCAGGA CCAGGAAGTA ACTTTAGAGG                650

AGGATCTGAT GGATATGGCA GTGGACGTGG ATTTGGGGAT GGCTATAATG                700

GGTATGGAGG AGGACCTGGA GGTGGCAATT TTGGAGGTAG CCCCGGTTAT                750

GGAGGAGGAA GAGG                                                       764
```

(2) INFORMATION FOR SEQ ID NO: 11:

(i) SEQUENCE CHARACTERISTICS:
(A) LENGTH: 20
(B) TYPE: nucleic acid
(C) STRANDEDNESS: Unknown
(D) TOPOLOGY: Linear (ii) MOLECULE TYPE: other nucleic acid (xi) SEQUENCE DESCRIPTION: SEQ ID NO: 11:

```
GAGTCCGGTT CGTGTTCGTC                                                  20
```

(2) INFORMATION FOR SEQ ID NO: 12:

(i) SEQUENCE CHARACTERISTICS:
(A) LENGTH: 23
(B) TYPE: nucleic acid
(C) STRANDEDNESS: Unknown
(D) TOPOLOGY: Linear (ii) MOLECULE TYPE: other nucleic acid (xi) SEQUENCE DESCRIPTION: SEQ ID NO: 12:

```
TGGGCTCTCA TCCTCTCCTA TTA                                              23
```

(2) INFORMATION FOR SEQ ID NO: 13:

(i) SEQUENCE CHARACTERISTICS:
(A) LENGTH: 19
(B) TYPE: nucleic acid
(C) STRANDEDNESS: Unknown
(D) TOPOLOGY: Linear (ii) MOLECULE TYPE: other nucleic acid (xi) SEQUENCE DESCRIPTION: SEQ ID NO: 13:

```
CTACAGCGCC AGGACGAGT                                                   19
```

(2) INFORMATION FOR SEQ ID NO: 14:

(i) SEQUENCE CHARACTERISTICS:
(A) LENGTH: 19

-continued (B) TYPE: nucleic acid
(C) STRANDEDNESS: Unknown
(D) TOPOLOGY: Linear (ii) MOLECULE TYPE: other nucleic acid (xi) SEQUENCE DESCRIPTION: SEQ ID NO: 14:

CCCATGGCAA TAGGAACAA 19

(2) INFORMATION FOR SEQ ID NO: 15:

(i) SEQUENCE CHARACTERISTICS:
(A) LENGTH: 24
(B) TYPE: nucleic acid
(C) STRANDEDNESS: Unknown
(D) TOPOLOGY: Linear (ii) MOLECULE TYPE: other nucleic acid (xi) SEQUENCE DESCRIPTION: SEQ ID NO: 15:

TGTTCTGTTA CCTCTGGGCT CTCA 24

(2) INFORMATION FOR SEQ ID NO: 16:

(i) SEQUENCE CHARACTERISTICS:
(A) LENGTH: 29
(B) TYPE: Amino Acid
(C) STRANDEDNESS: Unknown
(D) TOPOLOGY: Linear (ii) MOLECULE TYPE: peptide (xi) SEQUENCE DESCRIPTION: SEQ ID NO: 16:

```
Ala Thr Val Glu Glu Val Asp Ala Ala Met Asn Ala
  1               5                  10

Arg Pro His Lys Val Asp Gly Arg Val Val Glu Pro
         15                  20

Lys Arg Ala Val Ser
 25
```

(2) INFORMATION FOR SEQ ID NO: 17:

(i) SEQUENCE CHARACTERISTICS:
(A) LENGTH: 29
(B) TYPE: Amino Acid
(C) STRANDEDNESS: Unknown
(D) TOPOLOGY: Linear (ii) MOLECULE TYPE: peptide (xi) SEQUENCE DESCRIPTION: SEQ ID NO: 17:

```
Asp Asp His Asp Ser Val Asp Lys Ile Val Ile Gln
  1               5                  10

Lys Tyr His Thr Val Asn Gly His Asn Cys Glu Val
         15                  20

Arg Lys Ala Leu Ser
 25
```

(2) INFORMATION FOR SEQ ID NO: 18:

(i) SEQUENCE CHARACTERISTICS:
(A) LENGTH: 19
(B) TYPE: nucleic acid
(C) STRANDEDNESS: Unknown
(D) TOPOLOGY: Linear (ii) MOLECULE TYPE: other nucleic acid -continued (xi) SEQUENCE DESCRIPTION: SEQ ID NO: 18:

TGGCAGCATC AACCTCAGC 19

(2) INFORMATION FOR SEQ ID NO: 19:

(i) SEQUENCE CHARACTERISTICS:
(A) LENGTH: 22
(B) TYPE: nucleic acid
(C) STRANDEDNESS: Unknown
(D) TOPOLOGY: Linear (ii) MOLECULE TYPE: other nucleic acid (iv) ANTI-SENSE: YES (xi) SEQUENCE DESCRIPTION: SEQ ID NO: 19:

GAGAGAGAAA AGGAACAGTT CC 22

(2) INFORMATION FOR SEQ ID NO: 20:

(i) SEQUENCE CHARACTERISTICS:
(A) LENGTH: 24
(B) TYPE: nucleic acid
(C) STRANDEDNESS: Unknown
(D) TOPOLOGY: Linear (ii) MOLECULE TYPE: other nucleic acid (iv) ANTI-SENSE: YES (xi) SEQUENCE DESCRIPTION: SEQ ID NO: 20:

TAAGCTTTCC CCATTGTTCG TAGT 24

(2) INFORMATION FOR SEQ ID NO: 21:

(i) SEQUENCE CHARACTERISTICS:
(A) LENGTH: 19
(B) TYPE: nucleic acid
(C) STRANDEDNESS: Unknown
(D) TOPOLOGY: Linear (ii) MOLECULE TYPE: Nucleic Acid (iv) ANTI-SENSE: NO (xi) SEQUENCE DESCRIPTION: SEQ ID NO: 21:

CTACAGCGCC AGGACGAGT 19

(2) INFORMATION FOR SEQ ID NO: 22:

(i) SEQUENCE CHARACTERISTICS:
(A) LENGTH: 20
(B) TYPE: nucleic acid
(C) STRANDEDNESS: Unknown
(D) TOPOLOGY: Linear (ii) MOLECULE TYPE: other nucleic acid (iv) ANTI-SENSE: YES (xi) SEQUENCE DESCRIPTION: SEQ ID NO: 22:

CCCATGGCAA ATAGGAAGAA 20

(2) INFORMATION FOR SEQ ID NO: 23:

(i) SEQUENCE CHARACTERISTICS:
(A) LENGTH: 18
(B) TYPE: nucleic acid

-continued

```
        (C) STRANDEDNESS:  Unknown
        (D) TOPOLOGY:  Linear

    (ii) MOLECULE TYPE: other nucleic acid

    (iv) ANTI-SENSE:  NO

    (xi) SEQUENCE DESCRIPTION: SEQ ID NO: 23:

GCTCGGCTGC GGGAAATC                                        18
```